United States Patent
Besidski et al.

(10) Patent No.: US 9,439,904 B2
(45) Date of Patent: Sep. 13, 2016

(54) PYRIMIDINE COMPOUNDS AND THEIR USE AS GAMMA SECRETASE MODULATORS

(71) Applicant: Acturum Life Science AB, Sodertalje (SE)

(72) Inventors: Yevgeni Besidski, Tumba (SE); Ulrika Yngve, Uppsala (SE); Kim Paulsen, Huddinge (SE); Christian Erik Linde, Stockholm (SE); Istvan Macsari, Sodertalje (SE); Jonas Malmborg, Linkoping (SE); Alexander Paptchikhine, Uppsala (SE); Per Arvidsson, Jarna (SE)

(73) Assignee: Acturum Life Science AB, Sodertaje (SE)

( * ) Notice: Subject to any disclaimer, the term of this patent is extended or adjusted under 35 U.S.C. 154(b) by 0 days.

(21) Appl. No.: 14/895,528

(22) PCT Filed: Jun. 3, 2014

(86) PCT No.: PCT/EP2014/061503
§ 371 (c)(1),
(2) Date: Dec. 3, 2015

(87) PCT Pub. No.: WO2014/195323
PCT Pub. Date: Dec. 11, 2014

(65) Prior Publication Data
US 2016/0129002 A1    May 12, 2016

(30) Foreign Application Priority Data
Jun. 4, 2013 (SE) ...................................... 1350685

(51) Int. Cl.
A61K 31/506 (2006.01)
C07D 403/12 (2006.01)
C07D 403/14 (2006.01)
C07D 405/14 (2006.01)
A61K 45/06 (2006.01)

(52) U.S. Cl.
CPC ............ *A61K 31/506* (2013.01); *A61K 45/06* (2013.01); *C07D 403/12* (2013.01); *C07D 403/14* (2013.01); *C07D 405/14* (2013.01)

(58) Field of Classification Search
CPC ............... A61K 31/506; C07D 233/60; C07D 239/28; C07D 403/10; C07D 403/12; C07D 403/14; C07D 405/14
See application file for complete search history.

(56) References Cited

U.S. PATENT DOCUMENTS

2009/0215759 A1    8/2009    Baumann et al.

FOREIGN PATENT DOCUMENTS

| | | |
|---|---|---|
| WO | WO 2004/073705 | 9/2004 |
| WO | WO 2005/013985 | 2/2005 |
| WO | WO 2005/054193 | 6/2005 |
| WO | WO 2005/115990 | 12/2005 |
| WO | WO 2007/125364 | 11/2007 |
| WO | WO 2007/135969 | 11/2007 |
| WO | WO 2007/139149 | 12/2007 |
| WO | WO 2008/097538 | 8/2008 |
| WO | WO 2008/099210 | 8/2008 |
| WO | WO 2008/100412 | 8/2008 |
| WO | WO 2008/156580 | 12/2008 |
| WO | WO 2009/020580 | 2/2009 |
| WO | WO 2009/087127 | 7/2009 |
| WO | WO 2009/103652 | 8/2009 |
| WO | WO 2010/052199 | 5/2010 |
| WO | WO 2010/053438 | 5/2010 |
| WO | WO 2010/083141 | 7/2010 |
| WO | WO 2010/132015 | 11/2010 |
| WO | WO 2011/006903 | 1/2011 |
| WO | WO 2011/014535 | 2/2011 |
| WO | WO 2011/086098 | 7/2011 |
| WO | WO 2011/086099 | 7/2011 |
| WO | WO 2011/092272 | 8/2011 |
| WO | WO 2012/009309 | 1/2012 |

OTHER PUBLICATIONS

Beher D, Curr "Secrease Modulation and it's Promise for Alzheimer's Disease: a Rationale for Drug Discovery" *Top Med Chem*; 8(1):34-7; 2008.
Weggen et al. "A Subset of NSAIDs Lower Amyloidogenic Aβ42 Independently of Cyclooxygenase Activity" Nature 414(6860), 212-216 (2003).
Kounnas et al."*Modulation of Secretase Reduces B-Amyloid Deposition in a Transgenic Mouse Model of Alzheimer's Disease*" Neuron 67, 769-780 (2010).
Zettl et al. "*Exploring the Chemical Space of γ-Secretase Modulators*" Trends Pharmacol. Sci. 31, 402-410 (2010).
Jarowicki, K.; et al. "Protecting Groups". Perkin Trans.1, issue 18, p. 2109, 2001.

Primary Examiner — Sarah Pihonak
(74) Attorney, Agent, or Firm — Baker & Hostetler LLP

(57) ABSTRACT

The present invention relates to compounds of formula (I) and pharmaceutically acceptable salts thereof. The invention also relates to pharmaceutical compositions comprising these compounds, to processes for making these compounds, and to their use as medicaments for treatment and/or prevention of Aβ-related diseases.

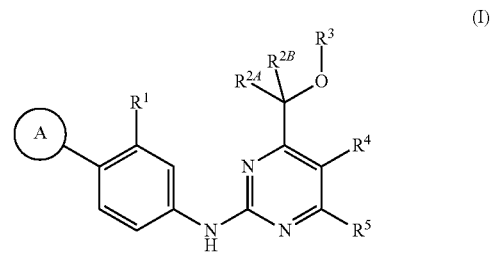

(I)

13 Claims, No Drawings

PYRIMIDINE COMPOUNDS AND THEIR USE AS GAMMA SECRETASE MODULATORS

CROSS-REFERENCE TO RELATED APPLICATIONS

This application is the National Stage of International Application No. PCT/EP2014/061503, filed Jun. 3, 2014, which claims the benefit of SE application number 1350685-2, filed Jun. 4, 2013, the disclosures of which are incorporated herein by reference in their entireties.

The present invention relates to pyrimidine compounds and pharmaceutically acceptable salts thereof. The present invention also relates to pharmaceutical compositions comprising these compounds, to processes for making these compounds, and to their use as medicaments for the treatment and/or prevention of various Aβ-related diseases.

BACKGROUND

The prime neuropathological event distinguishing Alzheimer's disease (AD) is deposition of the amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Aβ can be found in both plasma, cerebrospinal fluid (CSF), and in the medium from cultured cells, and is generated as a result of APP proteolysis. There are two main cleavages of APP that results in Aβ production, the so-called β-, and γ-cleavages. The β-cleavage, which generates the N terminus of Aβ, is catalyzed by the transmembrane aspartyl protease BACE1. The γ-cleavage, generating the Aβ C termini and subsequent release of the peptide, is affected by a multi-subunit aspartyl protease named γ-secretase. Both BACE1 and γ-secretase process APP at different sites, resulting in Aβ peptides of different lengths and heterologous N- and C-termini. The invention described herein covers all N-terminal variants of Aβ. Therefore, for the sake of simplicity, all N-terminal variants will be covered by the denotation Aβ.

The activity of γ-secretase causes the liberation of many Aβ peptides, such as Aβ37, Aβ38, Aβ39, Aβ40, Aβ42 and Aβ43, of which Aβ40 is the most common. These peptides show a different propensity to aggregate, and in particular Aβ42 is prone to form oligomers and fibrillar deposits. Intriguingly, human genetics strongly support a key role for Aβ42 as a key mediator of Alzheimer pathogenesis. Indeed, more than 150 different mutations causing familial Alzheimer's disease either result in an increase in the ratio of Aβ 42/40 peptides produced or affect the intrinsic aggregation behaviour of Aβ. Based on this knowledge, Aβ42 has become a prime target for therapeutic intervention in AD (Beher D, *Curr Top Med Chem* 2008; 8(1):34-7). Targeting Aβ42 at the level of γ-secretase activity must, however, be conducted with caution since γ-secretase catalyses proteolysis of many proteins, which have important physiological functions. Among its many substrates is the Notch receptor family, which signaling is essential for many different cell fate determination processes e.g. during embryogenesis and in the adult. As such, Aβ42 lowering strategies at the level of γ-secretase must be compatible with maintained Notch signaling.

It has been suggested that it is possible to combine γ-secretase interference and lowered Aβ42 production without obtaining toxic side effects due to impaired Notch signaling. There have, for instance, been reports which postulate that allosteric modulation of γ-secretase combines lowered Aβ42 production with maintained Notch signaling (Weggen et al. Nature 414(6860), 212-216 (2003); Kounnas et al. Neuron 67, 769-780 (2010); Zettl et al. Trends Pharmacol. Sci. 31, 402-410 (2010)). In addition, a number of compounds interfering with γ-secretase and Aβ production have been suggested in, e.g., WO2005/054193, WO2005/013985, WO2004/073705, WO2007/135969, WO2007/139149, WO2005/115990, WO2008/097538, WO2008/099210, WO2008/100412, WO2007/125364, WO2009/020580, WO2009/087127, WO2009/103652, WO2010/053438, WO2010/132015, WO2010/083141, WO2010/052199, WO2011/014535, WO2011/092272, WO2011/086098, WO2011/086099 and WO2012/009309.

The present invention relates to novel compounds which inhibit the Aβ40 and Aβ42 production, increase Aβ37 and Aβ38 levels and maintain Notch signaling. These compounds are therefore useful in the prevention and/or treatment of, e.g., Alzheimer's Disease (AD). The compounds have preferably an improved pharmacokinetic and pharmacodynamic profile compared to known compounds, such as improved selectivity, an improved absorbtion after oral administration, improved first passage and faster onset of action, as well as reduced side effects, such as no or a minimized impairment on Notch signaling. Passage of the blood-brain barrier is preferably improved as well.

DISCLOSURE OF THE INVENTION

The present invention is directed to compounds according to formula (I)

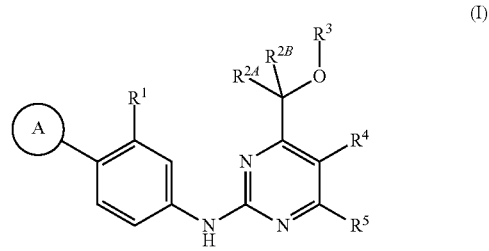

(I)

wherein:
A is 5- or 6-membered heteroaryl group comprising at least one nitrogen atom, wherein the 5- or 6-membered heteroaryl group is optionally substituted with one substituent selected from the group consisting of $C_{1-3}$-alkyl, $C_{1-3}$-alkoxy and halo;

$R^1$ is hydrogen, $C_{1-3}$-alkoxy, $C_{1-3}$-alkyl, cyano or halo;

$R^{2A}$ and $R^{2B}$ are each independently selected from the group consisting of hydrogen, $C_{1-3}$-alkyl and fluoro-$C_{1-3}$-alkyl;

or $R^{2A}$ and $R^{2B}$, together with the carbon atom to which they are attached, form a 3- to 6-membered saturated carbocyclic ring, which is optionally substituted with one or more fluoro substituents;

$R^3$ is $C_{1-3}$-alkyl, fluoro-$C_{1-3}$-alkyl or $C_{3-6}$-cycloalkyl-$C_{1-3}$-alkyl, wherein $C_{3-6}$-cycloalkyl is optionally substituted with one or more fluoro substituents;

$R^4$ is hydrogen, $C_{1-3}$-alkyl, fluoro or chloro;

$R^5$ is —$NR^{6A}R^{6B}$, —$OR^7$, —$CH_2OR^7$, —$C(R^{8A})(R^{8B})OH$, —$C(R^{9A})(R^{9B})$—$NR^{6A}R^{6B}$ or cyano-$C_{1-6}$-alkyl;

$R^{6A}$ is hydrogen, $C_{1-6}$-alkyl, fluoro-$C_{1-6}$-alkyl, hydroxy-$C_{1-6}$-alkyl; $C_{1-6}$-alkoxy-$C_{1-6}$-alkyl, cyano-$C_{1-6}$-alkyl, $C_{3-7}$-cycloalkyl, $C_{3-7}$-cycloalkyl-$C_{1-6}$-alkyl, heterocyclyl, heterocyclyl-$C_{1-6}$-alkyl, phenyl or phenyl-$C_{1-6}$-alkyl;

or when $R^5$ is —$NR^{6A}R^{6B}$, $R^{6A}$ together with $R^4$ is —$CH_2$—, —$CH_2$—$CH_2$— or —$CH_2$—$CH_2$—$CH_2$—, thereby forming a 4- to 6-membered ring containing one nitrogen atom;

$R^{6B}$ is hydrogen or $C_{1-6}$-alkyl;

or $R^{6A}$ and $R^{6B}$, together with the nitrogen atom to which they are attached, form a 4- to 6-membered saturated heterocyclic ring, which is optionally substituted with one or more substituents independently selected from the group consisting of fluoro and $C_{1-3}$-alkyl;

$R^7$ is $C_{1-6}$-alkyl, fluoro-$C_{1-6}$-alkyl or $C_{3-7}$-cycloalkyl-$C_{1-6}$-alkyl;

or when $R^5$ is $OR^7$, $R^7$ together with $R^4$ is —$CH_2$—, —$CH_2$—$CH_2$— or —$CH_2$—$CH_2$—$CH_2$—, thereby forming a 4- to 6-membered ring containing one oxygen atom;

$R^{8A}$ is hydrogen, $C_{1-6}$-alkyl, fluoro-$C_{1-6}$-alkyl, $C_{3-7}$-cycloalkyl, $C_{3-7}$-cycloalkyl-$C_{1-6}$-alkyl, phenyl or phenyl-$C_{1-6}$-alkyl; and $R^{8B}$, $R^{9A}$ and $R^{9B}$ are each independently selected from the group consisting of hydrogen and $C_{1-3}$-alkyl;

or a pharmaceutically acceptable salt thereof.

It has surprisingly been found that these compounds, especially when the $R^3$, $R^4$ and $R^5$ substituents are relative short, such as substituents containing 2 to 10, or 2 to 7 atoms, show excellent pIC50 values. It is believed that the $R^4$-group improved selectivity for Aβ42 and can be used to reduce the ratio Aβ 42/40 peptides. The compounds are expected to have improved blood-brain passage and thus an improved pharmacokinetic and dynamic profile, such as a faster onset of action and reduced side effects.

In one embodiment of the invention, A is the group consisting of pyridazinyl, imidazolyl and oxazolyl, and is optionally substituted with one substituent selected from the group consisting of $C_{1-3}$-alkyl, $C_{1-3}$-alkoxy and halo;

$R^1$ is hydrogen or $C_{1-2}$-alkoxy;

$R^{2A}$ and $R^{2B}$ are each independently selected from the group consisting of hydrogen and $C_{1-3}$-alkyl, or $R^{2A}$ and $R^{2B}$, together with the carbon atom to which they are attached, form a 3- to 6-membered saturated carbocyclic ring, which is optionally substituted with one or more fluoro substituents;

$R^3$ is $C_{1-3}$-alkyl, fluoro-$C_{1-3}$-alkyl or $C_{3-6}$-cycloalkyl-$C_{1-3}$-alkyl, wherein $C_{3-6}$-cycloalkyl is optionally substituted with one or more fluoro substituents;

$R^4$ is hydrogen or $C_{1-3}$-alkyl;

$R^5$ is —$NR^{6A}R^{6B}$, —$OR^7$, —$CH_2OR^7$, —$C(R^{8A})(R^{8B})OH$, —$C(R^{9A})(R^{9B})$—$NR^{6A}R^{6B}$ or cyano-$C_{1-6}$-alkyl;

$R^{6A}$ is hydrogen, $C_{1-6}$-alkyl, hydroxy-$C_{1-6}$-alkyl; $C_{1-6}$-alkoxy-$C_{1-6}$-alkyl, cyano-$C_{1-6}$-alkyl, $C_{3-7}$-cycloalkyl, $C_{3-7}$-cycloalkyl-$C_{1-6}$-alkyl, heterocyclyl or phenyl-$C_{1-6}$-alkyl;

$R^{6B}$ is hydrogen or $C_{1-6}$-alkyl;

or $R^{6A}$ and $R^{6B}$, together with the nitrogen atom to which they are attached, form a 4- to 6-membered saturated heterocyclic ring;

$R^7$ is $C_{1-6}$-alkyl, fluoro-$C_{1-6}$-alkyl or $C_{3-7}$-cycloalkyl-$C_{1-6}$-alkyl;

$R^{8A}$ is hydrogen, $C_{1-6}$-alkyl, fluoro-$C_{1-6}$-alkyl, $C_{3-7}$-cycloalkyl or $C_{3-7}$-cycloalkyl-$C_{1-6}$-alkyl; and $R^{8B}$, $R^{9A}$ and $R^{9B}$ are each independently selected from the group consisting of hydrogen and $C_{1-3}$-alkyl;

or a pharmaceutically acceptable salt thereof.

In one embodiment of the invention, A is a 5- or 6-membered heteroaryl ring selected from the group consisting of pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl, wherein the ring is optionally substituted with one $C_{1-3}$-alkyl substituent.

In another embodiment, A is selected from the group consisting of pyridinyl, pyridazinyl, pyrimidinyl, imidazolyl, thiazolyl, oxazolyl, pyrazolyl and triazolyl, and is substituted with one methyl substituent.

In another embodiment, A is selected from the group consisting of pyridazinyl, imidazolyl and oxazolyl, and is substituted with one methyl substituent.

In yet another embodiment, A is imidazolyl substituted with methyl.

In yet another embodiment, A is 4-methyl-1H-imidazol-1-yl.

In one embodiment of the invention, $R^1$ is hydrogen, methoxy or cyano.

In another embodiment, $R^1$ is methoxy.

In one embodiment of the invention, $R^{2A}$ and $R^{2B}$ are each independently hydrogen or $C_{1-3}$-alkyl; or $R^{2A}$ and $R^{2B}$, together with the carbon atom to which they are attached, form a cyclopropyl ring, which is optionally substituted with one or more fluoro substituents.

In another embodiment, $R^{2A}$ and $R^{2B}$ are each independently hydrogen or methyl.

In one embodiment of the invention, $R^3$ is $C_{1-2}$-alkyl, fluoro-$C_{2-3}$-alkyl or $C_{3-4}$-cycloalkyl-$C_{1-3}$-alkyl, wherein $C_{3-4}$-cycloalkyl is optionally substituted with one or more fluoro substituents.

In another embodiment, $R^3$ is methyl, ethyl, 2,2-difluoroethyl, 2,2,2-trifluoroethyl, 1,3-difluoro-propan-2-yl, 3,3,3-trifluoropropyl, cyclopropylmethyl or (3,3-difluorocyclobutyl)methyl.

In another embodiment, $R^3$ is 2,2,2-trifluoroethyl or cyclopropylmethyl.

In one embodiment of the invention, $R^4$ is hydrogen or $C_{1-3}$-alkyl.

In another embodiment, $R^4$ is hydrogen or methyl.

In another embodiment, $R^5$ is —$NR^{6A}R^{6B}$ wherein $R^{6A}$ is methyl or 2-propyl and $R^{6B}$ is hydrogen, or wherein $R^{6A}$ and $R^{6B}$, together with the nitrogen atom to which they are attached, form an azetidine ring.

In another embodiment, $R^5$ is —$OR^7$, wherein $R^7$ is methyl.

In another embodiment, $R^5$ is —$C(R^{8A})(R^{8B})OH$ wherein $R^{8A}$ is hydrogen, methyl, trifluoromethyl or cyclopropylmethyl and $R^{8B}$ is hydrogen or methyl.

In another embodiment, $R^5$ is cyanomethyl.

In a preferred embodiment of the invention, A is selected from the group consisting of pyridazinyl, imidazolyl and oxazolyl, and is substituted with one methyl substituent;
$R^1$ is hydrogen, methoxy or cyano;
$R^{2A}$ and $R^{2B}$ are each independently hydrogen or methyl;
$R^3$ is 2,2,2-trifluoroethyl or cyclopropylmethyl;
$R^4$ is hydrogen or methyl; and
$R^5$ is —$NR^{6A}R^{6B}$ wherein $R^{6A}$ is methyl or 2-propyl and $R^{6B}$ is hydrogen, or wherein $R^{6A}$ and $R^{6B}$, together with the nitrogen atom to which they are attached, form an azetidine ring; or
$R^5$ is —$OR^7$ wherein $R^7$ is methyl; or
$R^5$ is —$C(R^{8A})(R^{8B})OH$ wherein $R^{8A}$ is hydrogen, methyl, trifluoromethyl or cyclopropylmethyl and
$R^{8B}$ is hydrogen or methyl; or
$R^5$ is cyanomethyl.

In another preferred embodiment of the invention, A is 4-methyl-1H-imidazol-1-yl and $R^1$ is methoxy.

In another embodiment, the invention relates to compounds according to formula (Ia)

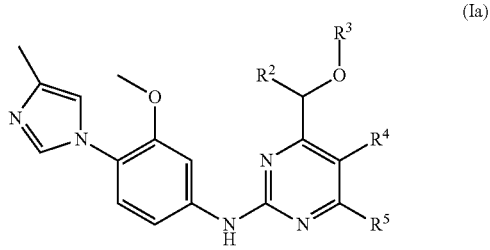

(Ia)

wherein:
$R^2$ is hydrogen or $C_{1-3}$-alkyl;
$R^3$ is fluoro-$C_{1-3}$-alkyl or $C_{3-6}$-cycloalkyl-$C_{1-3}$-alkyl, wherein $C_{3-6}$-cycloalkyl is optionally substituted with one or more fluoro substituents;
$R^4$ is hydrogen or $C_{1-3}$-alkyl;
$R^5$ is —$NR^{6A}R^{6B}$, —$OR^7$, —$CH_2OR^2$, —$C(R^{8A})(R^{8B})OH$, —$C(R^{9A})(R^{9B})$—$NR^{6A}R^{6B}$ or cyano-$C_{1-6}$-alkyl;
$R^{6A}$ is hydrogen, $C_{1-6}$-alkyl, fluoro-$C_{1-6}$-alkyl, hydroxy-$C_{1-6}$-alkyl, $C_{1-6}$-alkoxy-$C_{1-6}$-alkyl, cyano-$C_{1-6}$-alkyl, $C_{3-7}$-cycloalkyl, $C_{3-7}$-cycloalkyl-$C_{1-6}$-alkyl, heterocyclyl, heterocyclyl-$C_{1-6}$-alkyl, phenyl or phenyl-$C_{1-6}$-alkyl;
or when $R^5$ is —$NR^{6A}R^{6B}$, $R^{6A}$ together with $R^4$ is —$CH_2$—, —$CH_2$—$CH_2$— or —$CH_2$—$CH_2$—$CH_2$—, thereby forming a 4- to 6-membered ring containing one nitrogen atom;
$R^{6B}$ is hydrogen or $C_{1-6}$-alkyl;
or $R^{6A}$ and $R^{6B}$, together with the nitrogen atom to which they are attached, form a 4- to 6-membered saturated heterocyclic ring, which is optionally substituted with one or more substituents independently selected from the group consisting of fluoro and $C_{1-3}$-alkyl;
$R^7$ is $C_{1-6}$-alkyl, fluoro-$C_{1-6}$-alkyl or $C_{3-7}$-cycloalkyl-$C_{1-6}$-alkyl;
or when $R^5$ is $OR^7$, $R^7$ together with $R^4$ is —$CH_2$—, —$CH_2$—$CH_2$— or —$CH_2$—$CH_2$—$CH_2$—, thereby forming a 4- to 6-membered ring containing one oxygen atom;
$R^{8A}$ is hydrogen, $C_{1-6}$-alkyl, fluoro-$C_{1-6}$-alkyl, $C_{3-7}$-cycloalkyl, $C_{3-7}$-cycloalkyl-$C_{1-6}$-alkyl, phenyl or phenyl-$C_{1-6}$-alkyl; and
$R^{8B}$, $R^{9A}$ and $R^{9B}$ are each independently selected from the group consisting of hydrogen and $C_{1-3}$-alkyl, or a pharmaceutically acceptable salt thereof.

In one embodiment, the invention relates to a compound of formula (Ia), wherein $R^2$ is hydrogen or methyl.

In one embodiment, the invention relates to a compound of formula (Ia), wherein $R^3$ is 2,2,2-trifluoroethyl or cyclopropylmethyl.

In another embodiment, the invention relates to a compound of formula (Ia), wherein $R^4$ is hydrogen or methyl.

In another embodiment, the invention relates to a compound of formula (Ia), wherein:
$R^5$ is —$NR^{6A}R^{6B}$ wherein $R^{6A}$ is methyl or 2-propyl and $R^{6B}$ is hydrogen, or wherein $R^{6A}$ and $R^{6B}$, together with the nitrogen atom to which they are attached, form an azetidine ring; or
$R^5$ is —$OR^7$ wherein $R^2$ is methyl; or
$R^5$ is —$C(R^{8A})(R^{8B})OH$ wherein $R^{8A}$ is hydrogen, methyl, trifluoromethyl or cyclopropylmethyl and
$R^{8B}$ is hydrogen or methyl; or
$R^5$ is cyanomethyl.

In a preferred embodiment, the invention relates to a compound of formula (Ia), wherein:
$R^2$ is hydrogen or methyl;
$R^3$ is 2,2,2-trifluoroethyl or cyclopropylmethyl;
$R^4$ is hydrogen or methyl; and
$R^5$ is —$NR^{6A}R^{6B}$ wherein $R^{6A}$ is methyl or 2-propyl and $R^{6B}$ is hydrogen, or wherein $R^{6A}$ and $R^{6B}$, together with the nitrogen atom to which they are attached, form an azetidine ring; or
$R^5$ is —$OR^7$ wherein $R^2$ is methyl; or
$R^5$ is —$C(R^{8A})(R^{8B})OH$ wherein $R^{8A}$ is hydrogen, methyl, trifluoromethyl or cyclopropylmethyl and
$R^{8B}$ is hydrogen or methyl; or
$R^5$ is cyanomethyl.

In another embodiment, the invention relates to a compound of formula (I), or a pharmaceutically acceptable salt thereof, selected from the group consisting of:
4-(Azetidin-1-yl)-6-((cyclopropylmethoxy)methyl)-N-(3-methoxy-4-(4-methyl-1H-imidazol-1-yl)phenyl)pyrimidin-2-amine;
$N^4$-Methyl-$N^2$-(4-(4-methyl-1H-imidazol-1-yl)phenyl)-6-((2,2,2-trifluoroethoxy)methyl)-pyrimidine-2,4-diamine;
2-[2-[3-Methoxy-4-(4-methylimidazol-1-yl)anilino]-6-(2,2,2-trifluoroethoxymethyl)pyrimidin-4-yl]acetonitrile;
$N^2$-(3-Methoxy-4-(4-methyl-1H-imidazol-1-yl)phenyl)-$N^4$,5-dimethyl-6-((2,2,2-trifluoroethoxy)methyl)pyrimidine-2,4-diamine;
2-(2-(3-Methoxy-4-(4-methyl-1H-imidazol-1-yl)phenylamino)-5-methyl-6-((2,2,2-trifluoroethoxy)methyl)pyrimidin-4-yl)propan-2-ol;
1-(2-(3-Methoxy-4-(4-methyl-1H-imidazol-1-yl)phenylamino)-5-methyl-6-((2,2,2-trifluoroethoxy)methyl)pyrimidin-4-yl)ethanol;
1-(2-(3-Methoxy-4-(4-methyl-1H-imidazol-1-yl)phenylamino)-6-(1-(2,2,2-trifluoroethoxy)-ethyl)pyrimidin-4-yl)ethanol;
$N^4$-Isopropyl-$N^2$-(3-methoxy-4-(4-methyl-1H-imidazol-1-yl)phenyl)-6-((2,2,2-trifluoroethoxy)methyl)pyrimidine-2,4-diamine;
$N^2$-(3-Methoxy-4-(4-methyl-1H-imidazol-1-yl)phenyl)-N4-methyl-6-((2,2,2-trifluoroethoxy)methyl)pyrimidine-2,4-diamine;
(2-(3-Methoxy-4-(4-methyl-1H-imidazol-1-yl)phenylamino)-6-((2,2,2-trifluoroethoxy)methyl)pyrimidin-4-yl)methanol;
2-(2-(3-Methoxy-4-(4-methyl-1H-imidazol-1-yl)phenylamino)-6-(1-(2,2,2-trifluoroethoxy)ethyl)pyrimidin-4-yl)propan-2-ol;

2,2,2-Trifluoro-1-(2-(3-methoxy-4-(4-methyl-1H-imidazol-1-yl)phenylamino)-6-((2,2,2-trifluoroethoxy)methyl)pyrimidin-4-yl)ethanol;

2-Cyclopropyl-1-(2-(3-methoxy-4-(4-methyl-1H-imidazol-1-yl)phenylamino)-6-((2,2,2-trifluoroethoxy)methyl)pyrimidin-4-yl)ethanol;

1-(2-(3-Methoxy-4-(4-methyl-1H-imidazol-1-yl)phenylamino)-6-((2,2,2-trifluoroethoxy)methyl)pyrimidin-4-yl)-2-methylpropan-1-ol;

2-(2-(3-Methoxy-4-(4-methyl-1H-imidazol-1-yl)phenylamino)-6-((2,2,2-trifluoroethoxy)-methyl)pyrimidin-4-yl)propan-2-ol;

4-((Cyclopropylmethoxy)methyl)-N-(3-methoxy-4-(4-methyl-1H-imidazol-1-yl)phenyl)-6-((2,2,2-trifluoroethoxy)methyl)pyrimidin-2-amine;

2-(6-(((3,3-Difluorocyclobutyl)methoxy)methyl)-2-(3-methoxy-4-(4-methyl-1H-imidazol-1-yl)phenylamino)pyrimidin-4-yl)propan-2-ol;

2-(2-(3-Methoxy-4-(4-methyl-1H-imidazol-1-yl)phenylamino)-6-((3,3,3-trifluoropropoxy)-methyl)pyrimidin-4-yl)propan-2-ol;

2-(6-(((3,3-Difluorocyclobutyl)methoxy)methyl)-2-(3-methoxy-4-(6-methylpyridazin-4-yl)phenylamino)pyrimidin-4-yl)propan-2-ol;

4-(Azetidin-1-yl)-N-(3-methoxy-4-(4-methyl-1H-imidazol-1-yl)phenyl)-6-((2,2,2-trifluoroethoxy)methyl)pyrimidin-2-amine;

4-(Azetidin-1-yl)-N-(3-methoxy-4-(6-methylpyridazin-4-yl)phenyl)-6-((2,2,2-trifluoroethoxy)methyl)pyrimidin-2-amine;

4-(4,4-Difluoropiperidin-1-yl)-N-(3-methoxy-4-(6-methylpyridazin-4-yl)phenyl)-6-((2,2,2-trifluoroethoxy)methyl)pyrimidin-2-amine;

$N^4$-Isopropyl-$N^2$-(3-methoxy-4-(6-methylpyridazin-4-yl)phenyl)-6-((2,2,2-trifluoroethoxy)-methyl)pyrimidine-2,4-diamine;

$N^2$-(3-Methoxy-4-(6-methylpyridazin-4-yl)phenyl)-$N^4$-methyl-6-((2,2,2-trifluoroethoxy)-methyl)pyrimidine-2,4-diamine;

$N^4$-Benzyl-$N^2$-(3-methoxy-4-(4-methyl-1H-imidazol-1-yl)phenyl)-$N^4$-methyl-6-((2,2,2-trifluoroethoxy)methyl)pyrimidine-2,4-diamine;

4-(4,4-Difluoropiperidin-1-yl)-N-(3-methoxy-4-(4-methyl-1H-imidazol-1-yl)phenyl)-6-((2,2,2-trifluoroethoxy)methyl)pyrimidin-2-amine;

2-(2-(3-Methoxy-4-(4-methyl-1H-imidazol-1-yl)phenylamino)-6-(methoxymethyl)pyrimidin-4-yl)propan-2-ol;

Cyclopropyl(2-(3-methoxy-4-(4-methyl-1H-imidazol-1-yl)phenylamino)-6-((2,2,2-trifluoroethoxy)methyl)pyrimidin-4-yl)methanol;

2-(6-((Cyclopropylmethoxy)methyl)-2-(3-methoxy-4-(4-methyl-1H-imidazol-1-yl)phenylamino)pyrimidin-4-yl)propan-2-ol;

6-((Cyclopropylmethoxy)methyl)-N2-(3-methoxy-4-(4-methyl-1H-imidazol-1-yl)phenyl)-N4-methylpyrimidine-2,4-diamine;

1-(2-(3-Methoxy-4-(4-methoxy-1H-imidazol-1-yl)phenylamino)-6-((2,2,2-trifluoroethoxy)-methyl)pyrimidin-4-yl)ethanol;

2-(2-(3-Methoxy-4-(4-methoxy-1H-imidazol-1-yl)phenylamino)-6-((2,2,2-trifluoroethoxy)-methyl)pyrimidin-4-yl)propan-2-ol;

$N^4$-(Cyclopropylmethyl)-$N^2$-(3-methoxy-4-(4-methyl-1H-imidazol-1-yl)phenyl)-6-((2,2,2-trifluoroethoxy)methyl)pyrimidine-2,4-diamine;

$N^4$-Cyclopropyl-$N^2$-(3-methoxy-4-(4-methyl-1H-imidazol-1-yl)phenyl)-6-((2,2,2-trifluoroethoxy)methyl)pyrimidine-2,4-diamine;

$N^2$-(3-Methoxy-4-(4-methyl-1H-imidazol-1-yl)phenyl)-$N^4$-(oxetan-3-yl)-6-((2,2,2-trifluoroethoxy)methyl)pyrimidine-2,4-diamine;

1-(2-(3-Methoxy-4-(4-methyl-1H-imidazol-1-yl)phenylamino)-6-((2,2,2-trifluoroethoxy)-methyl)pyrimidin-4-ylamino)-2-methylpropan-2-ol;

N2-(3-Methoxy-4-(4-methyl-1H-imidazol-1-yl)phenyl)-N4-(2-methoxyethyl)-6-((2,2,2-trifluoroethoxy)methyl)pyrimidine-2,4-diamine;

3-(2-(3-Methoxy-4-(4-methyl-1H-imidazol-1-yl)phenylamino)-6-((2,2,2-trifluoroethoxy)-methyl)pyrimidin-4-ylamino)propanenitrile;

4-((Benzylamino)methyl)-N-(3-methoxy-4-(6-methylpyridazin-4-yl)phenyl)-6-((2,2,2-trifluoroethoxy)methyl)pyrimidin-2-amine;

4-((3-Fluoroazetidin-1-yl)methyl)-N-(3-methoxy-4-(4-methyl-1H-imidazol-1-yl)phenyl)-6-((2,2,2-trifluoroethoxy)methyl)pyrimidin-2-amine;

4-((Dimethylamino)methyl)-N-(3-methoxy-4-(4-methyl-1H-imidazol-1-yl)phenyl)-6-((2,2,2-trifluoroethoxy)methyl)pyrimidin-2-amine;

4-((3-Fluoroazetidin-1-yl)methyl)-N-(3-methoxy-4-(6-methylpyridazin-4-yl)phenyl)-6-((2,2,2-trifluoroethoxy)methyl)pyrimidin-2-amine;

4-(1-(3-Fluoroazetidin-1-yl)ethyl)-N-(3-methoxy-4-(4-methyl-1H-imidazol-1-yl)phenyl)-6-((2,2,2-trifluoroethoxy)methyl)pyrimidin-2-amine;

1-(2-(3-Methoxy-4-(4-methyl-1H-imidazol-1-yl)phenylamino)-6-((2,2,2-trifluoroethoxy)-methyl)pyrimidin-4-yl)ethanol;

2-(2-(3-Methoxy-4-(4-methyl-1H-imidazol-1-yl)phenylamino)-6-((2,2,2-trifluoroethoxy)-methyl)pyrimidin-4-yl)butan-2-ol;

2-(2-(3-Methoxy-4-(2-methyloxazol-5-yl)phenylamino)-6-((2,2,2-trifluoroethoxy)methyl)-pyrimidin-4-yl)propan-2-ol;

2-(2-(3-Methoxy-4-(6-methylpyridazin-4-yl)phenylamino)-6-((2,2,2-trifluoroethoxy)-methyl)pyrimidin-4-yl)propan-2-ol;

2-(2-(3-Methoxy-4-(2-methyloxazol-5-yl)phenylamino)-6-((2,2,2-trifluoroethoxy)methyl)-pyrimidin-4-yl)-3-methylbutan-2-ol;

(2-(3-Methoxy-4-(4-methyl-1H-imidazol-1-yl)phenylamino)-6-((2,2,2-trifluoroethoxy)-methyl)pyrimidin-4-yl)(phenyl)methanol;

2-(6-((1,3-Difluoropropan-2-yloxy)methyl)-2-(3-methoxy-4-(4-methyl-1H-imidazol-1-yl)phenylamino)pyrimidin-4-yl)propan-2-ol;

4-(Cyclopropylmethoxy)-N-[3-methoxy-4-(4-methyl-1H-imidazol-1-yl)phenyl]-6-[(2,2,2-trifluoroethoxy)methyl]pyrimidin-2-amine; and 2-(6-(1-Ethoxy-2,2-difluorocyclopropyl)-2-(3-methoxy-4-(4-methyl-1H-imidazol-1-yl)phenylamino)pyrimidin-4-yl)propan-2-ol.

In another aspect, the invention relates to a compound of formula (I), or a pharmaceutically acceptable salt thereof, for use in therapy.

In another aspect, the invention relates to a compound of formula (I), or a pharmaceutically acceptable salt thereof, for use in the treatment and/or prevention of an Aβ-related pathology.

In one embodiment, the invention relates to a compound of formula (I), or a pharmaceutically acceptable salt thereof, for use in the treatment and/or prevention of an Aβ-related pathology selected from the group consisting of Down's syndrome, a β-amyloid angiopathy, cerebral amyloid angiopathy, hereditary cerebral hemorrhage, a disorder associated with cognitive impairment, MCI ("mild cognitive impairment"), Alzheimer's disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy and cortical basal degeneration.

In another embodiment, the invention relates to a compound of formula (I), or a pharmaceutically acceptable salt thereof, for use in the treatment and/or prevention of Alzheimer's disease.

In another aspect, the invention relates to the use of a compound of formula (I), or a pharmaceutically acceptable salt thereof, in the manufacture of a medicament for the treatment and/or prevention of an Aβ-related pathology.

In another aspect, the invention relates to a method of treating and/or preventing an Aβ-related pathology in a mammal, comprising administering to said mammal a therapeutically effective amount of the compound of formula (I), or a pharmaceutically acceptable salt thereof.

In another aspect, the invention relates to a pharmaceutical composition comprising a therapeutically effective amount of a compound of formula (I), or a pharmaceutically acceptable salt thereof, in association with a pharmaceutically acceptable excipient, carrier or diluent. In one aspect, the invention relates to the pharmaceutical composition for use in therapy.

The treatment of Aβ-related pathology defined herein may be applied as a sole therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents, or atypical antipsychotic agents. Cognitive enhancing agents, memory enhancing agents and acetyl choline esterase inhibitors include onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX).

Such conjoint treatment may be achieved by way of the simultaneous, sequential or separate dosing of the individual components of the treatment. Such combination products employ the compounds, or pharmaceutically acceptable salts thereof, of the invention.

In another aspect, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) a pharmaceutically acceptable excipient, carrier or diluent.

In another aspect, the invention relates to a pharmaceutical composition comprising (i) a compound of formula (I), or a pharmaceutically acceptable salt thereof, (ii) at least one agent selected from the group consisting of acetyl cholinesterase inhibitors, anti-inflammatory agents, cognitive enhancing agents, memory enhancing agents, and atypical antipsychotic agents, and (iii) a pharmaceutically acceptable excipient, carrier or diluent.

In one aspect, the invention relates to a pharmaceutical composition comprising (i) a compound of formula (Ia), or a pharmaceutically acceptable salt thereof, (ii) at least one agent selected from the group consisting of onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX), and (iii) a pharmaceutically acceptable excipient, carrier or diluent.

Additional conventional chemotherapy or therapy may include one or more of the following categories of agents:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine and venlafaxine.

(ii) atypical antipsychotics such as quetiapine.

(iii) antipsychotics such as amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine and ziprasidone.

(iv) anxiolytics such as alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam and zolazepam.

(v) anticonvulsants such as carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine and zonisamide.

(vi) Alzheimer's therapies such as donepezil, memantine, rivastigmine, galantamine and tacrine.

(vii) Parkinson's therapies such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase.

(viii) migraine therapies such as almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan and zomitriptan.

(ix) stroke therapies such as abciximab, activase, NXY-059, citicoline, crobenetine, desmoteplase, repinotan, clopidogrel, eptifibatide, minocycline and traxoprodil.

(x) urinary incontinence therapies such as darafenacin, falvoxate, oxybutynin, propiverine, robalzotan, solifenacin and tolterodine.

(xi) neuropathic pain therapies including for example lidocain and capsaicin, and anticonvulsants such as gabapentin and pregabalin, and antidepressants such as duloxetine, venlafaxine, amitriptyline and klomipramine.

(xii) nociceptive pain therapies such as paracetamol; NSAIDS such as diclofenac, loxoprofen, naproxen, ketoprofen, ibuprofen, nabumeton, meloxicam and piroxicam; coxibs such as celecoxib, etoricoxib, lumiracoxib, rofecoxib, valdecoxib and parecoxib; and opioids such as morphine, oxycodone, buprenorfin and tramadol.

(xiii) insomnia therapies such as agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon and zolpidem.

(xiv) mood stabilizers such as carbamazepine, divalproex, gabapentin, lamotrigine, lithium, olanzapine, quetiapine, valproate, valproic acid and verapamil.

Such combination products employ the compounds of this invention within the dosage range described herein and the other pharmaceutically active compound or compounds within approved dosage ranges and/or the dosage described in the publication reference.

DEFINITIONS

The definitions set forth in this application are intended to clarify terms used throughout this application. The term "herein" means the entire application.

As used herein, the term "$C_{1-6}$-alkyl", used alone or as a suffix or prefix, is intended to include both branched and straight chain saturated aliphatic hydrocarbon groups having from 1 to 6 carbon atoms. Examples of $C_{1-6}$-alkyl include, but are not limited to, methyl, ethyl, n-propyl, i-propyl, n-butyl, i-butyl, sec-butyl, tert-butyl, n-pentyl and n-hexyl. Similarly, the term "$C_{1-3}$-alkyl" denotes alkyl having 1, 2 or 3 carbon atoms.

As used herein, the term "fluoro-$C_{1-6}$-alkyl", used alone or as a suffix or prefix, is intended to include both branched and straight chain saturated aliphatic hydrocarbon groups, having at least one fluoro substituent and having from 1 to 6 carbon atoms. Examples of fluoro-$C_{1-6}$-alkyl include, but are not limited to, fluoromethyl, difluoromethyl, trifluoromethyl, 1-fluoroethyl and 3-fluoropropyl.

As used herein, the term "cyano-$C_{1-6}$-alkyl", used alone or as a prefix, refers to a $C_{1-6}$-alkyl radical, as defined above, substituted with a cyano group. Exemplary cyano-$C_{1-6}$-alkyl groups include 2-cyanoethyl and 3-cyanopropyl.

As used herein, the term "hydroxy-$C_{1-6}$-alkyl", used alone or as a prefix, refers to a $C_{1-6}$-alkyl radical, as defined above, which is substituted with at least one hydroxy group. Exemplary hydroxy-$C_{1-6}$-alkyl groups include hydroxymethyl, 2-hydroxyethyl, 2-hydroxypropyl and 1-hydroxy-1-methylethyl.

As used herein, the term "$C_{1-6}$-alkoxy", used alone or as a suffix och prefix, refers to a $C_{1-6}$-alkyl radical which is attached to the remainder of the molecule through an oxygen atom. Examples of $C_{1-6}$-alkoxy include methoxy, ethoxy, n-propoxy, isopropoxy, n-butoxy, tert-butoxy, n-pentoxy and n-hexoxy. Similarly, the term "$C_{1-3}$-alkoxy" denotes alkoxy having 1, 2 or 3 carbon atoms.

As used herein, the term "$C_{1-6}$-alkoxy-$C_{1-6}$-alkyl" refers to a $C_{1-6}$-alkoxy group, as defined above, attached to a $C_{1-6}$-alkyl radical, as defined above. Examples of $C_{1-6}$-alkoxy-$C_{1-6}$-alkyl include methoxyethyl and ethoxypropyl.

As used herein, "halo" or "halogen" refers to fluoro, chloro, bromo, and iodo.

As used herein, the term "heteroaryl" refers to a monocyclic heteroaromatic ring having 5 or 6 ring members and wherein at least one ring member is nitrogen. Examples include pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl.

As used herein, the term "$C_{3-7}$-cycloalkyl", used alone or as suffix or prefix, denotes a cyclic saturated alkyl group having a ring size from 3 to 7 carbon atoms and includes cyclopropyl, cyclobutyl, cyclopentyl, cyclohexyl and cycloheptyl.

As used herein, the term "$C_{3-7}$-cycloalkyl-$C_{1-6}$-alkyl" refers to a $C_{3-7}$-cycloalkyl group that is attached through a $C_{1-6}$-alkyl radical. Examples of $C_{3-7}$-cycloalkyl-$C_{1-6}$-alkyl include cyclopropylmethyl, 2-cyclopropylethyl and 2-cyclohexylethyl.

As used herein, the term "heterocyclyl" denotes a saturated monocyclic ring containing 3 to 7 ring atoms wherein 1 or 2 ring atoms are indepently selected from nitrogen, sulphur and oxygen, and the remaining ring atoms are carbon. When present, the sulphur atom may be in an oxidized form (i.e., S=O or O=S=O). Examples of heterocyclyl include, but are not limited to, piperidinyl, piperazinyl, homopiperazinyl, azetidinyl, oxetanyl, morpholinyl, pyrrolidinyl, tetrahydropyranyl, tetrahydrofuranyl, tetrahydrothiopyranyl, tetrahydro-thiopyran 1-oxide and tetrahydro-thiopyran 1,1-dioxide.

As used herein, the term "heterocyclyl-$C_{1-6}$-alkyl" refers to a heterocyclyl group that is attached through a $C_{1-6}$-alkyl radical. Examples of heterocyclyl-$C_{1-6}$-alkyl include tetrahydropyran-4-ylmethyl, piperidin-4-ylmethyl, tetrahydrofuran-2-ylmethyl, oxetan-3-ylmethyl, 2-(4-morpholinyl) methyl and 2-(piperazin-1-yl)ethyl.

As used herein, the term "phenyl-$C_{1-6}$-alkyl" refers to a phenyl group that is attached through a $C_{1-3}$-alkyl radical. Examples of phenyl-$C_{1-3}$-alkyl include phenylmethyl (benzyl), 1-phenylethyl and 2-phenylethyl.

When $R^{2A}$ and $R^{2B}$, together with the carbon atom to which they are attached, form a 3- to 6-membered saturated carbocyclic ring, this ring is a cyclopropyl, cyclobutyl, cyclopentyl or cyclohexyl ring.

As used herein, the term "optional" or "optionally" means that the subsequently described event or circumstance may but need not occur, and that the description includes instances where the event or circumstance occurs and instances where it does not.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "protecting group" means temporary substituents protecting a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been extensively reviewed (see, e.g. Jarowicki, K.; Kocienski, P. Perkin Trans. 1, 2001, issue 18, p. 2109).

As used herein, "pharmaceutically acceptable salts" refer to forms of the disclosed compounds, wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

A variety of compounds in the present invention may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. All chiral, diastereomeric and racemic forms are intended, unless the specific stereochemistry or isomeric form is specifically indicated.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol.

Compounds and pharmaceutically acceptable salts of the invention further include hydrates and solvates thereof.

Compounds and salts described in this specification may be isotopically-labelled compounds (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^2$H (also written as "D" for deuterium), $^3$H (also written as "T" for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is used will depend on the specific application of that radio-labelled derivative. For example, for in vitro receptor labelling and competition assays, compounds that incorporate $^3$H or $^{14}$C are often useful. For radio-imaging applications $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The optimum dosage and frequency of administration will depend on the particular condition being treated and its severity; the age, sex, size and weight, diet, and general physical condition of the particular patient; other medication the patient may be taking; the route of administration; the formulation; and various other factors known to physicians and others skilled in the art.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

Preparation of Compounds

The compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3rd Edition, Wiley-Interscience, New York, 1999. Where necessary, the order of reaction process steps such as introduction of substituents can be altered.

Compounds of the present invention can be synthesized according to schemes 1-8.

Scheme 1. Synthesis of dichloropyrimidine intermediates

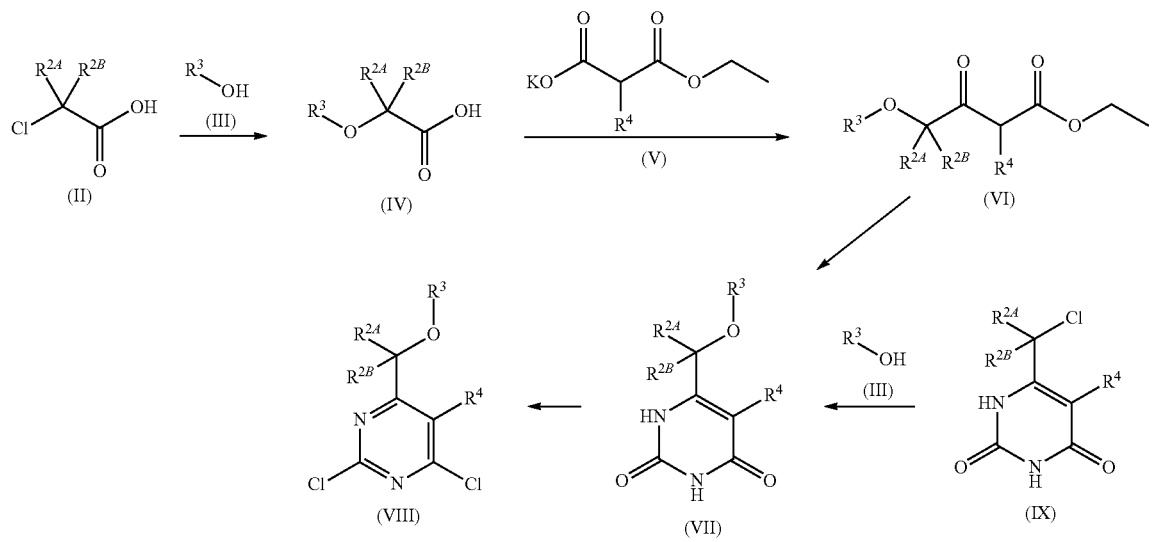

A compound of formula (II) is reacted with an alcohol of formula (III) in the presence of a base, such as sodium hydride, in a solvent, such as THF, to give a compound of formula (IV). The reaction is run at temperatures between 20° C. and 100° C. The compound of formula (IV) is reacted with a compound of formula (V) in the presence of for example di(1H-imidazol-1-yl)methanone, magnesium chloride and triethylamine in a solvent such as acetonitrile to give a compound of formula (VI). Compound (VI) is then cyclised in the presence of urea alternatively thiourea followed by treatment with for example bromoacetic acid to give a compound of formula (VII). The cyclisation reaction is run at temperatures in the range of 100° C. to 170° C. A compound of formula (VII) is consequently treated with a chlorinating agent such as phosphorus oxychloride, optionally in the presence of 4-dimethylaniline, at temperatures in the range of 50° C. to 150° C. to give a compound of formula (VIII).

Alternatively, when $R^{2A}$ and $R^{2B}$ are each H, a compound of formula (IX) can be treated with an alcohol of formula (III) in the presence of a base, such as cesium carbonate, in a solvent, such as DMF, at temperatures in the range of 50° C. to 150° C. to give a compound of formula (VII).

Scheme 2. Synthesis of dichloropyrimidine intermediates (alternate route; $R^{2A} = R^{2B} = H$)

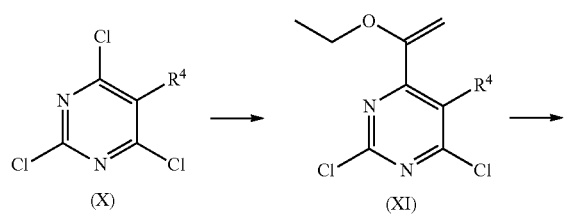

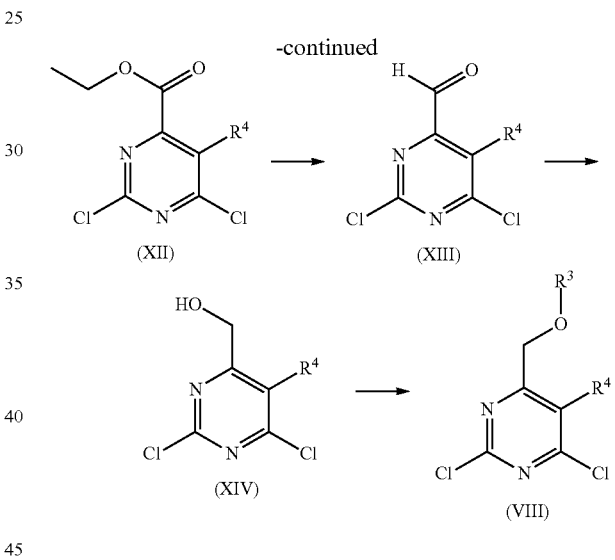

When $R^{2A}$ and $R^{2B}$ are each H, compounds of formula (I) can also be prepared as shown in Scheme 2. A compound of formula (X) is reacted with an organometallic ethoxyvinyl compound such as ethoxyvinyltributylstannane under Stille conditions in the presence of a catalyst such as dichloro[bis(triphenylphosphane)]palladium(II) to give a compound of formula (XI). The compound of formula (XI) is then oxidatively cleaved to a compound of formula (XII) using for example sodium metaperiodate and potassium permanganate in a solvent mixture such as dioxane and water, and then reduced in two steps via a compound of formula (XIII) to a compound of formula (XIV). Examples of conditions used in the first step are DIBAL-H, in a solvent mixture such as hexane and DCM, at temperatures in the range of −80° C. to 0° C., and in the second step sodium borohydride in a solvent such as ethanol, optionally in the presence of an acid such as acetic acid, at temperatures in the range of 0° C. to 50° C. The compound of formula (XIV) is then reacted with an alcohol $R^3OH$ under Mitsunobu conditions using for example tributyl phosphine and (azodicarbonyl)dipiperidine in a solvent such as DCM at temperatures in the range of 0°

C. to −50° C., or with an alkylhalide of formula R³X in the presence of a base such as sodium hydride, to give a compound of formula (VIII) where R²ᴬ and R²ᴮ are each hydrogen. Alternatively, a compound of formula (XIV) can be transformed into the corresponding sulfonyloxy compound for example by reaction with methylsulfonylchloride in the presence of a base such as diisopropylethylamine at temperatures between −50° C. and rt, and then reacted with an alcohol R³OH, in the presence of a base such as sodium hydroxide, optionally in the presence of a phase transfer catalyst such as tetrabutylammonium sulphate, and in a solvent such as benzene, to give a compound of formula (VIII).

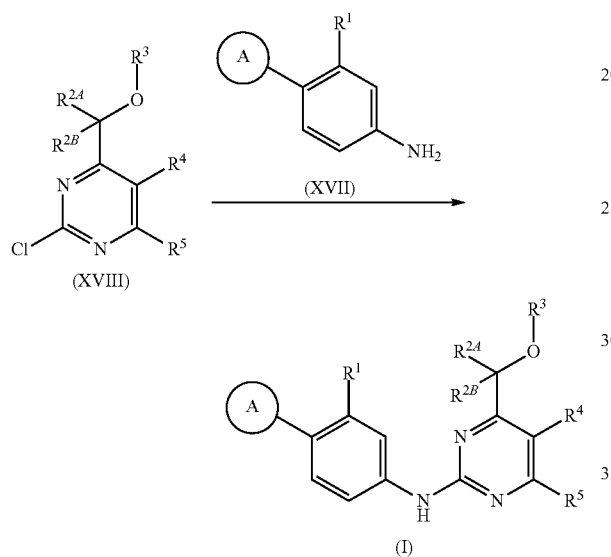

Scheme 3. Synthesis of compounds of formula (I).

A compound of formula (XVIII), wherein an appropriate R⁵ group is present, can be reacted with a compound of formula (XVII) under Buchwald-Hartwig conditions to give a compound of formula (I). Examples of reagents used in this reaction are palladium(II) acetate as catalyst, 2-(dicyclohexylphosphino)biphenyl as ligand, cesium carbonate as base and dioxane as solvent.

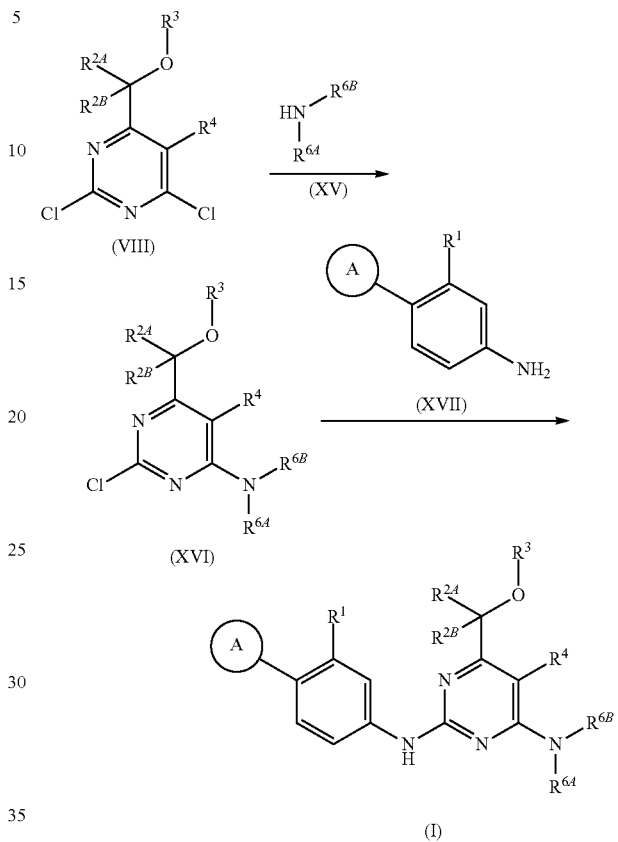

Scheme 4. Synthesis of compounds of formula (I) wherein R⁵ is —NR⁶ᴬR⁶ᴮ.

A compound of formula (VIII) is reacted with an amine of formula (XV), optionally in the presence of a base such as sodium methoxide or triethylamine, to give a compound of formula (XVI). This reaction is performed in a solvent such as acetonitrile or DMF at temperatures in the range of −10° C. to 100° C. The compound of formula (XVI is then reacted with a compound of formula (XVII) under Buchwald-Hartwig conditions to give a compound of formula (I) where R⁵ is —NR⁶ᴬR⁶ᴮ. Examples of reagents used in the Buchwald-Hartwig reaction are palladium(II) acetate as catalyst, 2-(dicyclohexylphosphino)biphenyl as ligand, cesium carbonate as base and dioxane as solvent.

Scheme 5. Synthesis of compounds of formula (I), wherein R⁵ is —C(R⁸ᴬ)(R⁸ᴮ)OH or —CH(R⁹ᴬ)—NR⁶ᴬR⁶ᴮ.

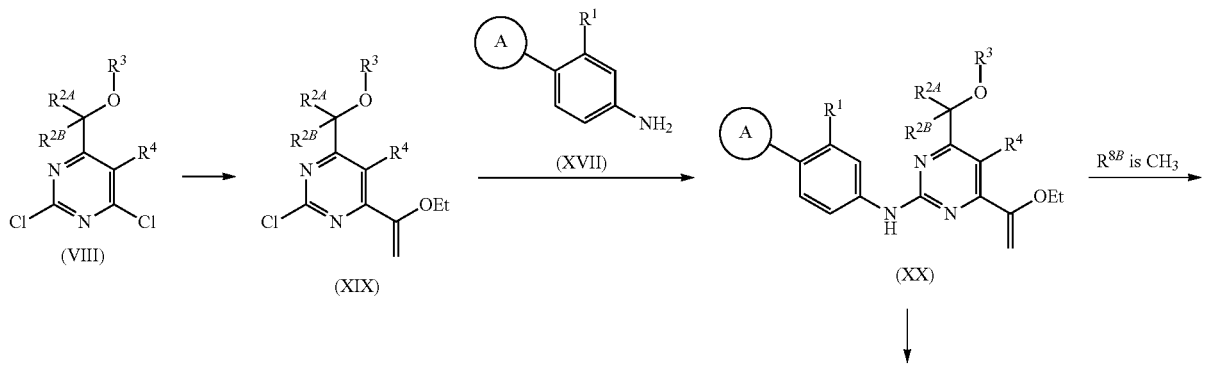

-continued

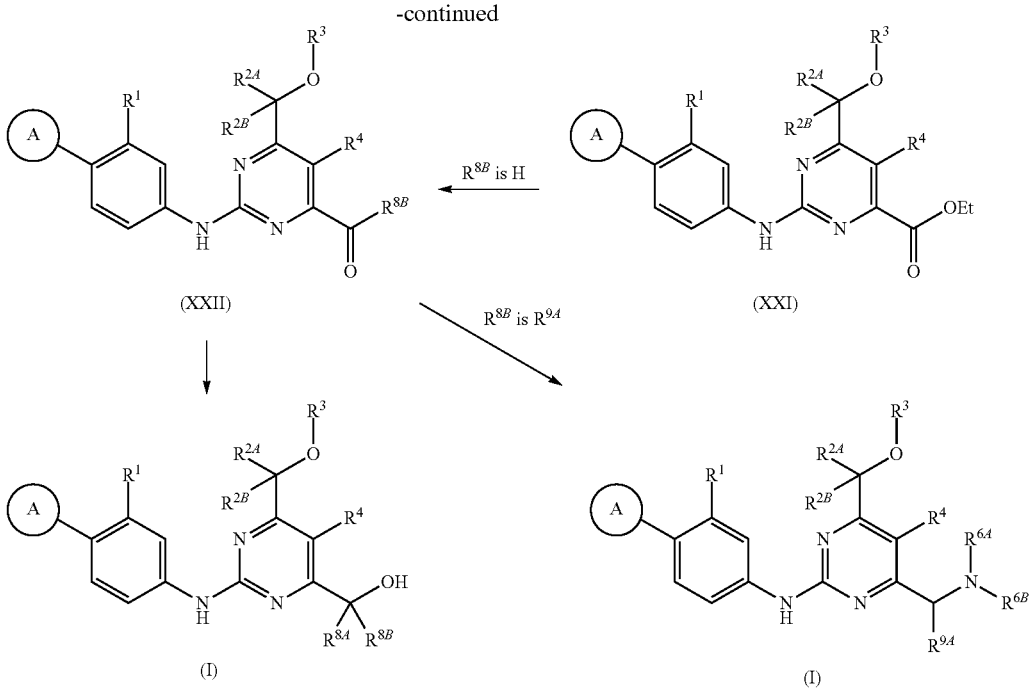

A compound of formula (VIII) is reacted with an organometallic ethoxyvinyl compound such as ethoxyvinyltributylstannane under Stille conditions to give a compound of formula (XIX). The compound of formula (XIX) is then reacted with a compound of formula (XVII) under Buchwald-Hartwig conditions to give a compound of formula (XX). The compound of formula (XX) can be hydrolysed under acidic conditions to a compound of formula (XXII) where $R^{8B}$ is methyl, in the presence of an acid such as hydrochloric acid, in solvents such as water and dioxane, and at temperatures in the range of 20° C. to 100° C. Alternatively, a compound of formula (XX) can be oxidatively cleaved, in the presence of for example sodium metaperiodate and potassium permanganate in solvents such as water and dioxane, to give a compound of formula (XXI). The compound of formula (XXI) is then transformed into a compound of formula (XXII) where $R^{8B}$ is hydrogen in the presence of a suitable reducing agent such as DIBAL-H in solvents such as hexane and dichloromethane at temperatures in the range of −78° C. to 20° C.

A compound of formula (XXII) is transformed into a compound of formula (I) where $R^5$ is —C($R^{8A}$)($R^{8B}$)OH via reaction with an organometallic reagent such as a Grignard reagent $R^{8A}$MgCl or $R^{8A}$MgBr, optionally in the presence of an additive such as lithium chloride, in an etheral solvent such as THF, dioxane or diethyl ether, and at temperatures in the range of −78° C. to 30° C.

Alternatively, a compound of formula (XXII) is transformed into a compound of formula (I) where $R^{8A}$ is hydrogen in the presence of a suitable reducing agent such as DIBAL-H in solvents such as hexane and dichloromethane at temperatures in the range of −78° C. to 20° C.

A compound of formula (XXII) is converted into a compound of formula (I) where $R^5$ is —CH($R^{9A}$)—N($R^{6A}$)($R^{6B}$) by reductive amination using a suitable amine ($R^{6A}$)($R^{6B}$)NH and a reducing agent such as sodium triacetoxy borohydride or sodium cyanoborohydride, optionally in the presence of an acid such as citric acid or acetic acid.

Scheme 6. Synthesis of compounds of formula (I), wherein $R^5$ is cyanomethyl.

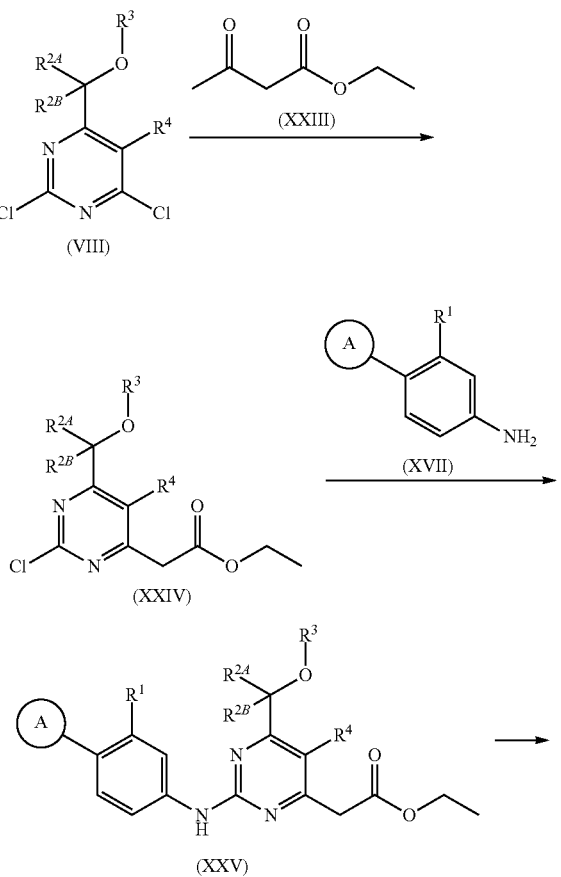

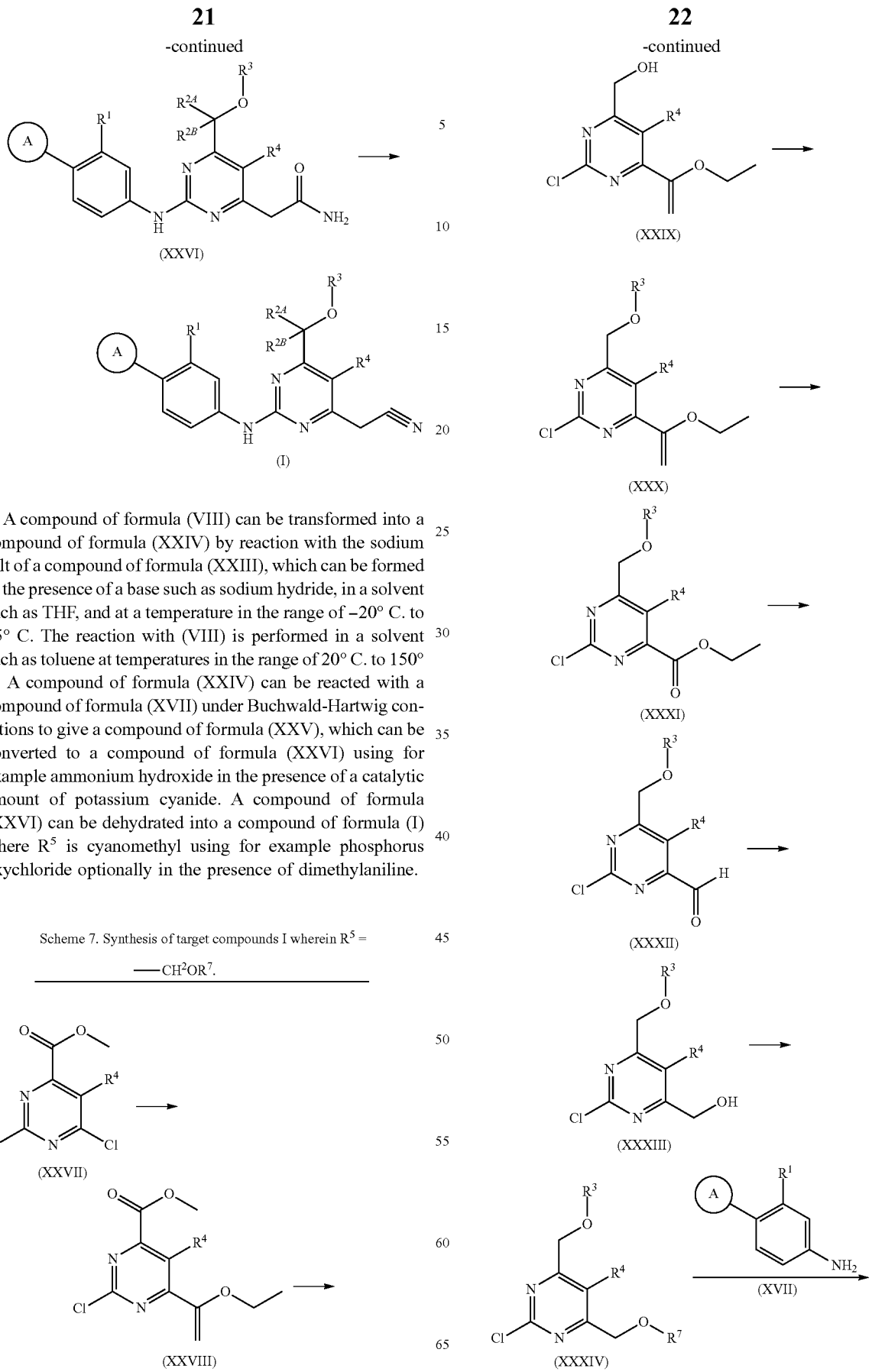

A compound of formula (VIII) can be transformed into a compound of formula (XXIV) by reaction with the sodium salt of a compound of formula (XXIII), which can be formed in the presence of a base such as sodium hydride, in a solvent such as THF, and at a temperature in the range of −20° C. to 25° C. The reaction with (VIII) is performed in a solvent such as toluene at temperatures in the range of 20° C. to 150° C. A compound of formula (XXIV) can be reacted with a compound of formula (XVII) under Buchwald-Hartwig conditions to give a compound of formula (XXV), which can be converted to a compound of formula (XXVI) using for example ammonium hydroxide in the presence of a catalytic amount of potassium cyanide. A compound of formula (XXVI) can be dehydrated into a compound of formula (I) where $R^5$ is cyanomethyl using for example phosphorus oxychloride optionally in the presence of dimethylaniline.

Scheme 7. Synthesis of target compounds I wherein $R^5$ = —CH$^2$OR$^7$.

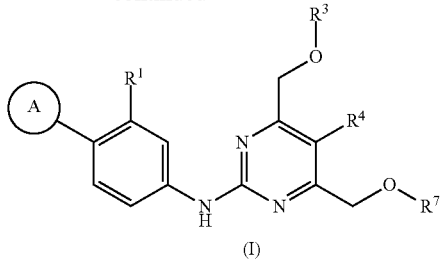

A compound of formula (XXVII) can be transformed into a compound of formula (XXVIII) using the same method as for transforming a compound of formula (X) into a compound of formula (XI) (scheme 2). The compound of formula (XXVIII) can then be transformed into a compound of formula (XXIX) using a reducing agent such as DIBAL-H in solvents such as hexane and dichloromethane at temperatures in the range of −78° C. and 20° C. The compound of formula (XXIX) can be transformed into a compound of formula (XXX) using the methods described above for transforming a compound of formula (XIV) into a compound of formula (VIII). The further transformation of a compound of formula (XXX) into a compound (XXXII) via compounds of formula (XXXI) and (XXXII) can be done using the method described for transformation of a compound of formula (XI) into a compound of formula (XIV), via compounds of formula (XII) and (XIII). A compound of formula (XXXIII) can be transformed into a compound of formula (XXXIV) by reaction with a compound $R^7OH$ or $R^7X$ where X is a leaving group such as chloro, bromo, iodo or sulfonyloxy, using the conditions described for the transformation of a compound of formula (XIV) into a compound of formula (VIII). A compound of formula (XXXIV) is reacted with a compound of formula (XVII), using Buchwald-Hartwig conditions, to give a compound of formula (I) where $R^5$ is —$CH_2OR^7$.

Scheme 8. Synthesis of intermediate compounds of formula (XVII).

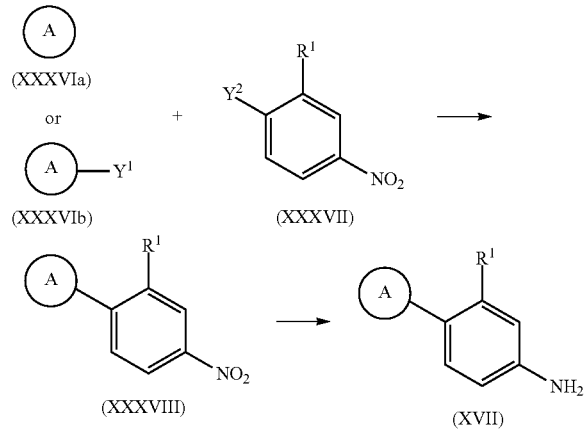

If ring A is attached to the phenyl ring through a nitrogen atom, a heteroaryl compound of formula (XXXVIa) is reacted with a compound of formula (XXXVII) wherein $Y^2$ is fluoro, chloro or bromo, to give a compound of formula (XXXVIII). The reaction is performed in the presence of a base such as potassium carbonate or sodium hydroxide in a solvent such as acetonitrile, DMSO or DMF at temperatures in the range of about 20° C. and 150° C. Alternatively, the reaction can be catalysed by for example Cu(I)iodide.

If ring A is attached to the phenyl ring though a carbon atom, a heteroaryl compound of formula (XXXVIb) wherein $Y^1$ is for example trialkylstannane, boronic acid or boronic ester, is reacted with a compound of formula (XXXVII) wherein $Y^2$ is chlorine, bromine, iodine or triflate, to give a compound of formula (XXXVIII). This reaction is performed under Stille or Suzuki conditions in the presence of for example a palladium catalyst, a ligand and a base.

Alternatively, the heterocyclic ring A can also be formed onto the phenyl ring. For example, a compound of formula (XXXVII) wherein $Y^2$ is —$C(O)CH_2Br$ can be transformed in several steps to form an appropriately substituted oxazole ring.

A compound of formula (XXXVIII) can be transformed into a compound of formula (XVII) using standard conditions, for example catalytic hydrogenation with palladium on charcoal.

General Methods

NMR spectra were recorded on a 400 MHz or 500 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used: TMS δ 0.00, or the residual solvent signal of DMSO-$d_6$ δ 2.50, $CD_3OD$ δ 3.30, acetone-$d_6$ 2.04 or $CDCl_3$ δ 7.27 (unless otherwise indicated). Resonance multiplicities are denoted s, d, t, q, m, br and app for singlet, doublet, triplet, quartet, multiplet, broad and apparent, respectively.

Preparative or analytical High pressure liquid chromatography (HPLC) was performed on a reversed phase (RP) column. A linear gradient was applied using for example mobile phase A (0.1% Formic Acid in MilliQ $H_2O$ or 0.1% $NH_3$ in MilliQ $H_2O$ or 10 mM $NH_4OAc$ and 5% $CH_3CN$ in MilliQ $H_2O$.) and B ($CH_3OH$ or $CH_3CN$). Mass spectrometer (MS) analyses were performed in positive and/or negative ion mode using electrospray ionization (ESI+/−), atmospheric pressure photo ionization (APPI+/−) and/or atmospheric pressure chemical ionization (APCI+/−).

Gas chromatography (GC) was performed on a GC equipped with a mass spectrometer (MS) or flame ionization detector (FID). The MS ion source was either an electron impact (EI) or a chemical ionization (CI, reactant gas methane).

Supercritical Fluid Chromatography (SFC) was performed on a straight phase column. A isocratic flow was applied using mobile phase A ($CO_2$) and for example mobile phase B (MeOH, EtOH or IPA optionally containing DEA).

The compounds have been named using CambridgeSoft MedChem ELN v2.1, the naming tool in reaxys (reaxys.com) or are according to IUPAC convention.

Abbreviations
Aq. aqueous
DCE dichloroethane
DCM dichloromethane
DMA dimethylacetamide
DMF dimethylformamide
EtOAc ethyl acetate
MeOH methanol
MTBE methyl tert-butyl ether
rt room temperature
Sat. saturated
(s) solid
TFA trifluoroacetic acid
THF tetra hydrofuran
TMS tetramethylsilane Preparation of Starting Materials The starting materials for the syntheses of the Examples are either commercially available or prepared by standard methods described in the literature.

EXAMPLES

The compounds described in this specification are further illustrated in the following Examples. These Examples are given by way of illustration only and are non-limiting.

Intermediate 1

6-((2,2,2-Trifluoroethoxy)methyl)pyrimidine-2,4(1H,3H)-dione

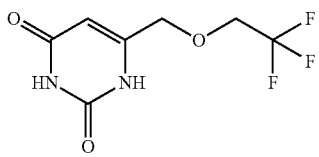 [SMILES: O=c1cc(COCC(F)(F)F)[nH]c(=O)[nH]1]

A mixture of 6-(chloromethyl)pyrimidine-2,4(1H,3H)-dione (1 g, 6.23 mmol), 2,2,2-trifluoroethanol (2.235 mL, 31.14 mmol) and cesium carbonate (6.09 g, 18.68 mmol) in dimethylformamide (10 mL) was heated in a microwave oven at 100° C. for 30 min. The mixture was filtered and the volatiles were removed in vacuum. The residue was treated with diluted HCl (pH 4.5) and cooled to 0° C. The resulting crystals were collected by filtration and dried in vacuum cabinet to yield the title compound, 0.92 g (66%).

MS (APCI−) m/z 223 (M−H)−. $^1$H NMR (500 MHz, DMSO-$d_6$) ⊠ ppm 4.18 (q, 2H) 4.36 (s, 2H) 5.49 (s, 1H) 10.93 (br. s, 1H) 11.03 (br. s, 1H).

Intermediate 2

2,4-dichloro-6-((2,2,2-trifluoroethoxy)methyl)pyrimidine

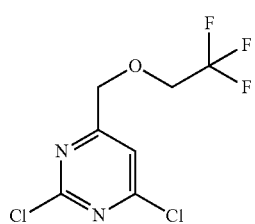 [SMILES: FC(F)(F)COCc1cc(Cl)nc(Cl)n1]

(Dimethylamino)benzene (0.990 mL, 7.81 mmol) was added to phosphorus oxychloride (10.40 mL, 111.54 mmol) under nitrogen while stirring. 6-((2,2,2-trifluoroethoxy)methyl)pyrimidine-2,4(1H,3H)-dione (2.5 g, 11.15 mmol) was added and the mixture was heated at 110° C. until it became homogeneuos (approximately 10-15 min). The solution was cooled to ambient temperature and poured cautiously into ice-cold water. After the exothermic reaction was over, the mixture was extracted twice with dichloromethane. The organic phase was separated, dried over sodium sulfate, then filtered through a pad of silica gel and concentrated in vacuum to yield the title product, 2.67 g (92%).

MS (APCI+) m/z 261 (M+H)+. $^1$H NMR (400 MHz, CHLOROFORM-d) ⊠ ppm 4.03 (q, 2H) 4.77 (s, 2H) 7.51 (t, 1H).

Intermediate 3

2-Chloro-N-methyl-6-((2,2,2-trifluoroethoxy)methyl)pyrimidin-4-amine

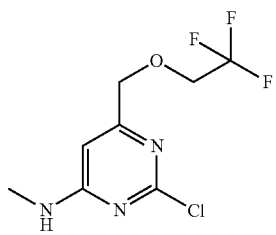 [SMILES: CNc1cc(COCC(F)(F)F)nc(Cl)n1]

A solution of methylamine (0.382 mL of 33% solution in absolute ethanol, 3.06 mmol) was added to a solution of 2,4-dichloro-6-((2,2,2-trifluoroethoxy)methyl)pyrimidine (200 mg, 0.77 mmol) in acetonitrile (3 mL). The mixture was stirred at ambient temperature for 30 minutes. The solvents was removed in vacuum, and the residue was purified by preparative HPLC to yield the title compound, 135 mg, (69%).

MS (ES+) m/z 256 (M+H)+. $^1$H NMR (500 MHz, CHLOROFORM-d) ⊠ ppm 3.01 (br. s, 3H) 3.97 (q, 2H) 4.59 (br. s, 2H) 6.43 (s, 1H).

Intermediate 4

Ethyl 2,6-dichloro-5-methylpyrimidine-4-carboxylate

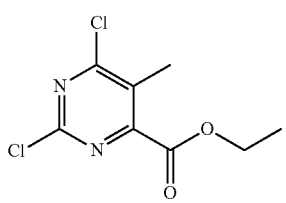

Sodium metaperiodate (2.111 g, 9.87 mmol) was suspended in water (20 mL) and sonicated until a clear solution was obtained. 2,4-Dichloro-6-(1-ethoxyvinyl)-5-methylpyrimidine (1.15 g, 4.93 mmol) dissolved in 1,4-dioxane (40 mL) was added followed by potassium permanganate (0.117 g, 0.74 mmol). The mixture was stirred at rt for 2 h. The mixture was filtered. The filtrate was diluted with saturated solutions of sodium bicarbonate and sodium chloride and extracted twice with ethyl acetate. The organic phase was dried over sodium sulfate, filtered through a pad of silica gel and concentrated in vacuum. Column chromatography on silica gel using a 0-30% gradient of ethyl acetate in heptane yielded the title product, 0.67 g (58%).

MS (APCI⁺) m/z 235 (M+H)⁺. ¹H NMR (500 MHz, CHLOROFORM-d): δ ppm 4.47 (q, 2H), 2.49 (s, 3H), 1.43 (t, 3H).

Intermediate 5

(2,6-Dichloro-5-methylpyrimidin-4-yl)methanol

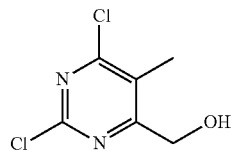

To a solution of 2,6-dichloro-5-methylpyrimidine-4-carbaldehyde (0.325 g, 1.70 mmol) in ethanol (10 mL) sodium borohydride (0.032 g, 0.85 mmol) was added at 0° C. The mixture was stirred for 10 minutes. Acetic acid (4 drops) was added and the volatiles were removed in vacuum. The residue was treated with 10% solution of methanol in chloroform (10 mL). The slurry was filtered through a pad of silica gel. The filtrate was concentrated and purified by column chromatography on silica using a gradient 0-4% of methanol in dichloromethane as eluent to yield the title product, 0.23 g (71%).

MS (APCI⁺) m/z 193 (M+H)⁺. ¹H NMR (500 MHz, CHLOROFORM-d): δ ppm 2.25 (s, 3H), 3.86 (br. s, 1H), 4.72 (s, 2H).

Intermediate 6

1-(2-(3-Methoxy-4-(4-methyl-1H-imidazol-1-yl)phenylamino)-5-methyl-6-((2,2,2-trifluoroethoxy)methyl)pyrimidin-4-yl)ethanone

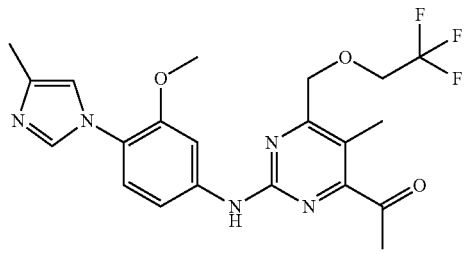 [SMILES: COc1cc(Nc2nc(COCC(F)(F)F)c(C)c(C(C)=O)n2)ccc1-n1cnc(C)c1]

A solution of 4-(1-ethoxyvinyl)-N-(3-methoxy-4-(4-methyl-1H-imidazol-1-yl)phenyl)-5-methyl-6-((2,2,2-trifluoroethoxy)methyl)pyrimidin-2-amine (52 mg, 0.11 mmol) in dioxane (4 mL), water (0.5 mL) and concentrated hydrochloric acid (0.028 mL, 0.33 mmol) was heated at 40° C. for 35 min. Sodium bicarbonate (40 mg) and water (2 mL) were added. The volatiles were removed in vacuum, the residue was coevaporated with dioxane to give the title compound.

MS (APCI⁺) m/z 450 (M+H)⁺.

Intermediate 7

6-(1-(2,2,2-Trifluoroethoxy)ethyl)pyrimidine-2,4(1H,3H)-dione

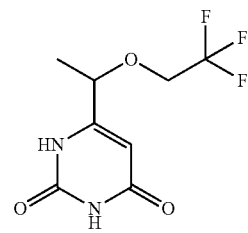 [SMILES: CC(OCC(F)(F)F)c1cc(=O)[nH]c(=O)[nH]1]

A mixture of ethyl 3-oxo-4-(2,2,2-trifluoroethoxy)pentanoate (3.29 g, 13.58 mmol) and urea (0.816 g, 13.58 mmol) was heated at 160° C. under nitrogen for 10 h. A solution of potassium carbonate (3.8 g) in water (30 mL) was added and the mixture was extracted with MTBE (20 mL). The aqueous phase was acidified to pH 2 and extracted with MTBE (20 mL). The organic phase was dried over sodium sulfate and concentrated in vacuum to yield the title product, 1.35 g (42%).

MS (APCI⁺) m/z 239 (M+H)⁺. ¹H NMR (500 MHz, DMSO-d₆) δ ppm 1.37 (d, 3H) 4.10 (q, 2H) 4.32 (q, 1H) 5.45 (s, 1H).

Intermediate 8

2,4-Dichloro-6-(1-(2,2,2-trifluoroethoxy)ethyl)pyrimidine

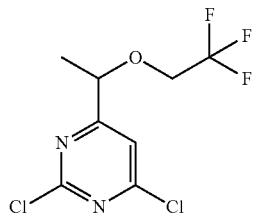 [SMILES: CC(OCC(F)(F)F)c1cc(Cl)nc(Cl)n1]

(Dimethylamino)benzene (0.503 mL, 3.97 mmol) was added under nitrogen to stirred phosphorus oxychloride (5.28 mL, 56.68 mmol), followed by addition of 6-(1-(2,2,2-trifluoroethoxy)ethyl)pyrimidine-2,4(1H,3H)-dione (1.35 g, 5.67 mmol). The mixture was heated at 110° C. for 30 min. The mixture was cooled and poured to ice and the water phase was extracted twice with dichloromethane. The organic phase was dried over sodium sulphate, filtered through a short pad of silica gel and concentrated in vacuum to yield the title compound, 0.5 g (32%).

MS (APCI⁺) m/z 275 (M+H)⁺. ¹H NMR (500 MHz, CHLOROFORM-d) δ ppm 1.56 (d, 3H) 3.83-3.98 (m, 2H) 4.63 (q, 1H) 7.50 (s, 1H).

Intermediate 9

2-Chloro-4-(1-ethoxyvinyl)-6-(1-(2,2,2-trifluoroethoxy)ethyl)pyrimidine

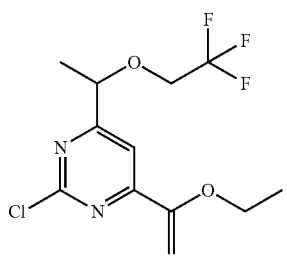 [SMILES: C=C(OCC)c1cc(C(C)OCC(F)(F)F)nc(Cl)n1]

Tributyl(1-ethoxyvinyl)stannane (0.466 mL, 1.38 mmol) was added to a degased solution of 2,4-dichloro-6-(1-(2,2,2-trifluoroethoxy)ethyl)pyrimidine (0.379 g, 1.38 mmol) and bis(triphenylphosphine)palladium chloride (0.019 g, 0.03 mmol) in dimethylformamide (8 mL) under nitrogen. The mixture was heated at 80° C. for 1.5 h, then cooled and poured into solution of potassium fluoride (2 g) in water (40 mL). The mixture was extracted with MTBE (2×50 mL), the organic phase was washed with water (30 mL), dried over sodium sulfate and concentrated in vacuum. The residue was purified by column chromatography on silica eluting with dichloromethane to yield the title product, 350 mg (82%).

MS (APCI$^+$) m/z 311 (M+H)$^+$. $^1$H NMR (500 MHz, CHLOROFORM-d) ⊡ ppm 1.45 (t, 3H) 1.55 (d, 3H) 3.86 (q, 2H) 3.98 (q, 2H) 4.59 (d, 1H) 4.63 (q, 1H) 5.74 (d, 1H) 7.73 (s, 1H).

Intermediate 10

4-(1-Ethoxyvinyl)-N-(3-methoxy-4-(4-methyl-1H-imidazol-1-yl)phenyl)-6-(1-(2,2,2-trifluoroethoxy)ethyl)pyrimidin-2-amine

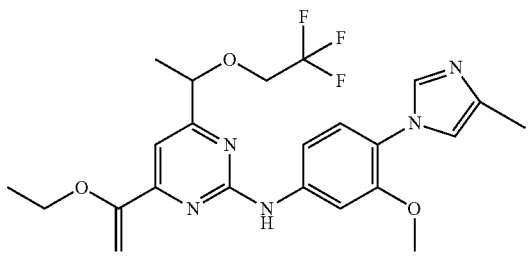 [SMILES: C=C(OCC)c1cc(C(C)OCC(F)(F)F)nc(Nc2ccc(-n3cnc(C)c3)c(OC)c2)n1]

2-Chloro-4-(1-ethoxyvinyl)-6-(1-(2,2,2-trifluoroethoxy)ethyl)pyrimidine (0.35 g, 1.13 mmol), 3-methoxy-4-(4-methyl-1H-imidazol-1-yl)aniline (0.275 g, 1.35 mmol), palladium(II) acetate (0.038 g, 0.17 mmol), 2-(dicyclohexylphosphino)biphenyl (0.059 g, 0.17 mmol), cesium carbonate (0.734 g, 2.25 mmol) and dioxane (4 mL) were mixed in a vial. The vial was capped, evacuated and flushed with nitrogen. The reaction mixture was heated by microwave irradiation at 120° C. for 2.5 h, cooled and filtered through a pad of silica gel. The pad was eluted with 10% methanol in ethyl acetate. The solvents were evaporated and the residue was purified by column chromatography on silica gel using a gradient of 0-10% methanol in dichloromethane as eluent to yield the title product, 0.38 mg (70%).

MS (APCI$^+$) m/z 478.4 (M+H)$^+$. $^1$H NMR (500 MHz, CHLOROFORM-d) ⊡ ppm 1.47 (t, 3H) 1.57 (d, 3H) 2.32 (s, 3H) 3.83 (m, 1H) 3.89 (s, 1H) 3.91 (m, 1H) 3.98 (q, 2H) 4.50 (d, 1H) 4.55 (q, 1H) 5.60 (d, 1H) 6.90 (s, 1H) 7.04 (dd, 1H) 7.18 (d, 1H) 7.28 (d, 1H) 7.44 (s, 1H) 7.66 (d, 1H) 7.90 (d, 1H).

Intermediate 11

1-(2-(3-Methoxy-4-(4-methyl-1H-imidazol-1-yl)phenylamino)-6-(1-(2,2,2-trifluoroethoxy)ethyl)pyrimidin-4-yl)ethanone

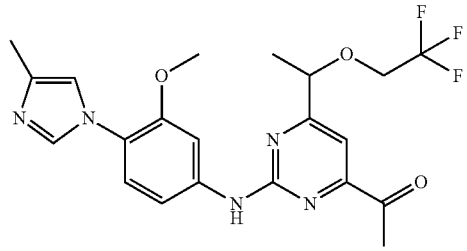 [SMILES: COc1cc(Nc2nc(C(C)=O)cc(C(C)OCC(F)(F)F)n2)ccc1-n1cnc(C)c1]

Concentrated hydrochloric acid (0.202 mL, 2.39 mmol) was added to a solution of 4-(1-ethoxy-vinyl)-N-(3-methoxy-4-(4-methyl-1H-imidazol-1-yl)phenyl)-6-(1-(2,2,2-trifluoroethoxy)ethyl)-pyrimidin-2-amine (0.38 g, 0.80 mmol) in dioxane (30 mL) and water (3 mL). The solution was heated at 40° C. for 0.5 h, cooled and neutralised with sodium bicarbonate (1 g). Brine was added (5 mL) and the water phase was extracted with ethyl acetate (2×10 mL). The organic phase was dried over sodium sulfate and concentrated. The residue was purified on silica gel column using a gradient 0-4% methanol in dichloromethane as eluent to give the title compound, 330 mg (92%).

MS (APCI$^+$) m/z 450 (M+H)$^+$. $^1$H NMR (500 MHz, CHLOROFORM-d) ⊡ ppm 1.57 (d, 3H) 2.31 (s, 3H) 2.71 (s, 3H) 3.87-3.95 (m, 2H) 3.90 (s, 3H) 4.60 (q, 1H) 6.90 (s, 1H) 7.13 (dd, 1H) 7.22 (d, 1H) 7.47 (s, 1H) 7.54 (s, 1H) 7.67 (d, 1H) 7.79 (d, 1H).

Intermediate 12

2-Chloro-N-isopropyl-6-((2,2,2-trifluoroethoxy)methyl)pyrimidin-4-amine

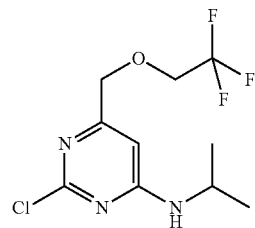 [SMILES: CC(C)Nc1cc(COCC(F)(F)F)nc(Cl)n1]

A solution of isopropylamine (0.102 mL, 1.20 mmol) in methanol (2 mL) was added dropwise to an ice-cold solution of 2,4-dichloro-6-((2,2,2-trifluoroethoxy)methyl)pyrimidine (104 mg, 0.40 mmol) in acetonitrile (2.0 mL). The reaction mixture was stirred overnight at rt. The mixture was purified by preparative HPLC yielding the title compound 63 mg (56%).

MS (ES⁺) m/z 284 (M+H)⁺. ¹H NMR (500 MHz, CHLOROFORM-d) ⏰ 1.21-1.34 (m, 7H), 3.98 (q, 2H), 4.62 (s, 2H), 6.42 (br. s, 1H).

Intermediate 13

2-Chloro-4-(1-ethoxyvinyl)-6-((2,2,2-trifluoroethoxy)methyl)pyrimidine

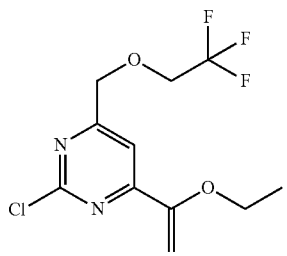 [SMILES: C=C(OCC)c1cc(COCC(F)(F)F)nc(Cl)n1]

A degased solution of 2,4-dichloro-6-((2,2,2-trifluoroethoxy)methyl)pyrimidine (7 g, 26.82 mmol), tributyl(1-ethoxyvinyl)stannane (9.51 mL, 28.16 mmol) and bis(triphenylphosphine)-palladium chloride (0.376 g, 0.54 mmol) in dimethylformamide (200 mL) was heated under argon at 100° C. for 1.5 h. The mixture was poured into a solution of potassium fluoride (20 g) in water 250 mL, and the mixture was extracted with MTBE (300 mL). The organic phase was washed with water, dried over sodium sulfate, and filtered through a pad of silica gel. The residue was crystallised from heptane (50 mL) to yield the title compound (4.0 g). The mother liquor was concentrated in vacuum and purified by column chromatography on silica gel, using a gradient of 0-15% ethyl acetate in heptane as eluent to yield additional amount of the title compound (2.9 g), total yield being 6.45 g (81%).

MS (APCI+) m/z 297.2 (M+H)⁺. ¹H NMR (400 MHz, CHLOROFORM-d) N ppm 1.45 (t, 3H) 3.98 (q, 2H) 4.01 (q, 2H) 4.60 (d, 1H) 4.76 (s, 2H) 5.73 (d, 1H) 7.73 (s, 1H).

Intermediate 14

4-(1-Ethoxyvinyl)-N-(3-methoxy-4-(4-methyl-1H-imidazol-1-yl)phenyl)-6-((2,2,2-trifluoroethoxy)methyl)pyrimidin-2-amine

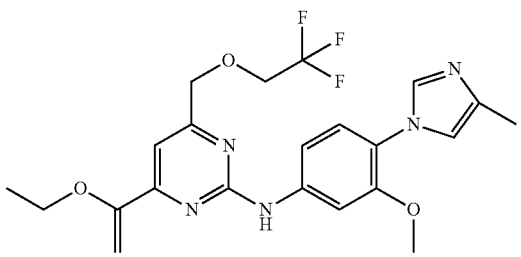 [SMILES: C=C(OCC)c1cc(COCC(F)(F)F)nc(Nc2ccc(-n3cnc(C)c3)c(OC)c2)n1]

A vial containing 2-chloro-4-(1-ethoxyvinyl)-6-((2,2,2-trifluoroethoxy)methyl)pyrimidine (0.29 g, 0.98 mmol), 3-methoxy-4-(4-methyl-1H-imidazol-1-yl)aniline (0.397 g, 1.96 mmol), cesium carbonate (0.637 g, 1.96 mmol), palladium(II) acetate (0.033 g, 0.15 mmol), 2-(dicyclohexylphosphino)biphenyl (0.051 g, 0.15 mmol) and dioxane (14 mL) was capped, evacuated and flushed with nitrogen. The mixture was heated by microwave irradiation at 120° C. for 1.5 h. The volatiles were removed in vacuum and the residue was extracted with ethyl acetate (20 mL). The solution was filtered through a short pad of silica gel, the pad was washed with ethyl acetate and 10% solution of methanol in ethyl acetate. The solvents were removed in vacuum and the residue was purified by column chromatography using a 0-5% gradient of methanol in dichloromethane to yield the title compound, 418 mg (92%).

MS (APCI⁺) m/z 464 (M+H)⁺. ¹H NMR (500 MHz, CHLOROFORM-d) δ ppm: 1.46 (t, 3H) 2.31 (d, 3H) 3.88 (s, 3H) 3.99 (m, 4H) 4.50 (d, 1H) 4.69 (s, 2H) 5.59 (d, 1H) 6.88 (d, 1H) 7.03 (dd, 1H) 7.17 (d, 1H) 7.31 (s, 1H) 7.64 (d, 1H) 7.82 (d, 1H).

Intermediate 15

Ethyl 2-(3-methoxy-4-(4-methyl-1H-imidazol-1-yl) phenylamino)-6-((2,2,2-trifluoroethoxy)methyl)pyrimidine-4-carboxylate

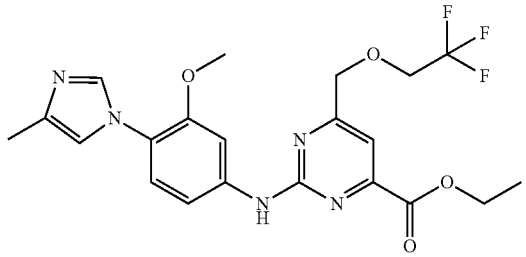 [SMILES: CCOC(=O)c1cc(COCC(F)(F)F)nc(Nc2ccc(-n3cnc(C)c3)c(OC)c2)n1]

To a solution of sodium metaperiodate (1.200 g, 5.61 mmol) and 4-(1-ethoxyvinyl)-N-(3-methoxy-4-(4-methyl-1H-imidazol-1-yl)phenyl)-6-((2,2,2-trifluoroethoxy) methyl)pyrimidin-2-amine (1.3 g, 2.81 mmol) in a mixture of water (30 mL) and 1,4-dioxane (60 mL) potassium permanganate (0.066 g, 0.42 mmol) was added in portions of 10-15 mg in intervals of 5-8 min at ambient temperature. The mixture was filtered, the precipitate was washed with dioxane and ethyl acetate. Sodium bicarbonate and sodium chloride were added to the filtrate, the organic phase was separated, and the water phase was additionally extracted with ethyl acetate. The combined organic phase was dried over sodium sulfate and concentrated in vacuum. The residue was separated on a silica gel column using a gradient of 0-5% methanol in dichloromethane as eluent to yield the title product, 0.96 g (74%).

MS (APCI⁺) m/z 466 (M+H)⁺. ¹H NMR (500 MHz, CHLOROFORM-d) ⏰ ppm 1.45 (t, 3H) 2.31 (s, 3H) 3.91 (s, 3H) 4.03 (q, 2H) 4.49 (q, 2H) 4.75 (s, 2H) 6.89 (s, 1H) 7.03 (dd, 1H) 7.19 (d, 1H) 7.57 (s, 1H) 7.58 (s, 1H) 7.66 (d, 1H) 7.92 (br. s, 1H).

Intermediate 16

2-(3-Methoxy-4-(4-methyl-1H-imidazol-1-yl)phenylamino)-6-((2,2,2-trifluoroethoxy)methyl)pyrimidine-4-carbaldehyde

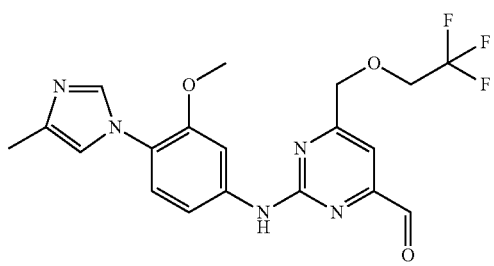 [SMILES: COc1cc(Nc2nc(C=O)cc(COCC(F)(F)F)n2)ccc1-n1cnc(C)c1]

To a solution of ethyl 2-(3-methoxy-4-(4-methyl-1H-imidazol-1-yl)phenylamino)-6-((2,2,2-trifluoroethoxy)methyl)pyrimidine-4-carboxylate (0.49 g, 1.05 mmol) in dry dichloromethane (25 mL) diisobutyl aluminum hydride (2.63 mL, 1M solution in hexane, 2.63 mmol), was added under nitrogen during 10 min at −78° C. The mixture was stirred at −78° C. for 1 h. Diisobutyl aluminum hydride solution (2.8 mL) was added and the mixture was stirred for 10 min. The mixture was quenched with methanol and allowed to warm to ambient temperature. Water (5 mL) was added, the slurry was stirred for 20 min and filtered through a pad of diatomeous earth. The pad was washed with 10% solution of methanol in dichloromethane. The organic phase was separated and the water phase was extracted with 10% solution of methanol in dichloromethane. The combined organic extracts was dried over sodium sulfate and concentrated in vacuum. The residue was purified by column chromatography on silica eluting with 0-5% gradient of methanol in dichloromethane to yield the title compounds, 318 mg (72%).

MS (APCI+) m/z 422 (M+H)$^+$. $^1$H NMR (500 MHz, CHLOROFORM-d) ? ppm 2.32 (s, 3H) 3.90 (s, 3H) 4.03 (q, 2H) 4.76 (s, 2H) 6.90 (s, 1H) 7.18 (dd, 1H) 7.23 (d, 1H) 7.44 (s, 1H) 7.51 (s, 1H) 7.68 (s, 1H) 7.74 (d, 1H) 9.95 (s, 1H).

Intermediate 17

2-Chloro-6-((2,2,2-trifluoroethoxy)methyl)pyrimidine-4-carbaldehyde

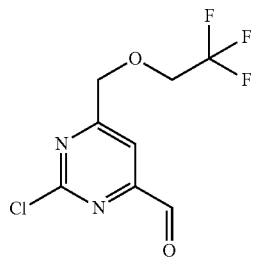 [SMILES: O=Cc1cc(COCC(F)(F)F)nc(Cl)n1]

Diisobutyl aluminum hydride (1.21 mL, 1M solution in hexane, 1.22 mmol), was added dropwise to a solution of ethyl 2-chloro-6-((2,2,2-trifluoroethoxy)methyl)pyrimidine-4-carboxylate (242 mg, 0.81 mmol) in dry dichloromethane (10 mL) under nitrogen at −78° C. The mixture was stirred at −78° C. for 1 h. Diisobutyl aluminum hydride solution (1 mL) was added and the mixture was stirred for 15 minutes. The mixture was quenched with methanol and allowed to reach ambient temperature. Water (10 mL) and dichloromethane were added, the pH of the water phase was adjusted to 6 by addition of acetic acid. The mixture was filtered through a pad of silica gel and sodium bicarbonate. The water phase was extracted with 5% solution of methanol in dichloromethane (3×10 mL). The combined organic phase was dried over sodium sulfate and concentrated in vacuum to yield the title product, 216 mg (100%).

MS (APCI$^+$) m/z 255 (M+H)$^+$.

Intermediate 18

1-(2-Chloro-6-((2,2,2-trifluoroethoxy)methyl)pyrimidin-4-yl)-2-methylpropan-1-ol

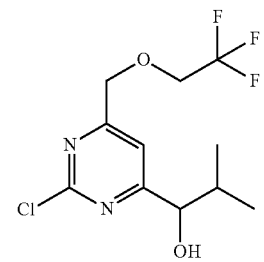 [SMILES: CC(C)C(O)c1cc(COCC(F)(F)F)nc(Cl)n1]

Isopropyl magnesium chloride (0.601 mL, 2M solution, 1.20 mmol) was added dropwise to a solution of 2-chloro-6-((2,2,2-trifluoroethoxy)methyl)pyrimidine-4-carbaldehyde (180 mg, 0.71 mmol) in diethyl ether (10 mL) at −30° C. The mixture was quenched with a saturated aqueous solution of ammonium chloride and then extracted with ethyl acetate (×2). The combined organic phase was dried over sodium sulfate and concentrate. The residue was purified by column chromatography on silica to yield the title compound, 25 mg (12%).

MS (APCI$^+$) m/z 299 (M+H)$^+$. $^1$H NMR (500 MHz, CHLOROFORM-d) ? ppm 0.82 (d, 3H) 1.05 (d, 3H) 2.14 (m, 1H) 3.08 (d, 1H) 4.02 (q, 2H) 4.57 (t, 1H) 4.77 (s, 2H) 7.46 (s, 1H).

Intermediate 19

1-(2-(3-Methoxy-4-(4-methyl-1H-imidazol-1-yl)phenylamino)-6-((2,2,2-trifluoroethoxy)methyl)pyrimidin-4-yl)ethanone

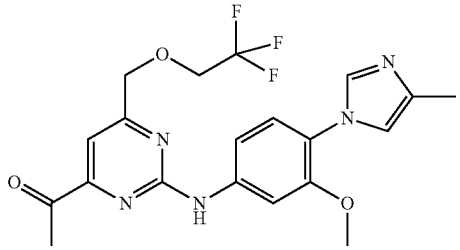 [SMILES: COc1cc(Nc2nc(COCC(F)(F)F)cc(C(C)=O)n2)ccc1-n1cnc(C)c1]

To a solution of 4-(1-ethoxyvinyl)-N-(3-methoxy-4-(4-methyl-1H-imidazol-1-yl)phenyl)-6-((2,2,2-trifluoroethoxy)methyl)pyrimidin-2-amine (0.418 g, 0.90 mmol) dioxane (60 mL) water 3 mL) and concentrated hydrochloric acid (0.228 mL, 2.71 mmol) were added. The solution was heated at 60° C. for 15 min. The mixture was treated with an excess of sodium bicarbonate and extracted twice with ethyl acetate. The combined organic phase was dried over sodium sulfate and concentrated to yield the title product as a solid 390 mg (99%).

MS (ES$^+$) m/z 436 [M+H]$^+$. $^1$H NMR (500 MHz, CHLOROFORM-d) δ ppm 2.36 (s, 3H) 2.72 (s, 3H) 3.91 (s, 3H) 4.03 (q, 2H) 4.75 (s, 2H) 6.92 (s, 1H) 7.15 (d, 1H) 7.24 (d, 1H) 7.38 (s, 1H) 7.51 (s, 1H) 7.76 (s, 1H) 7.78-7.82 (m, 1H).

Intermediate 20

(2-Chloro-6-(1-ethoxyvinyl)pyrimidin-4-yl)methanol

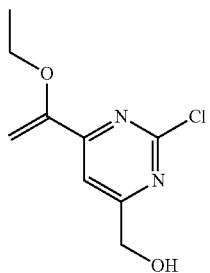

Methyl 2-chloro-6-(1-ethoxyvinyl)pyrimidine-4-carboxylate (3.5 g, 14.4 mmol) was dissolved in MeOH (35 mL), DMF (24.50 mL) and water (3.5 mL) by careful heating. The mixture was cooled on an ice-bath and sodium borohydride (1.47 g, 38.9 mmol) was added in small portions (about 50 mg every 5 min) keeping the temperature below 5° C. After 3.5 h acetic acid (3.96 mL, 69.23 mmol) was added. MeOH was evaporated and water was added. The mixture was extracted with diisopropyl ether (3×50 mL). The organic layer was washed with brine, dried over anhydrous sodium sulfate, filtered and concentrated. The product was purified by column chromatography on silica eluting with a gradient of EtOAc in heptane to give the title compound as a solid 1.8 g (58%).

MS (ES$^+$) m/z 215 [M+H]$^+$. $^1$H NMR (500 MHz, CHLOROFORM-d) δ ppm 1.45 (t, 3H) 3.98 (q, 2H) 4.59 (d, 1H) 4.79 (s, 2H) 5.74 (d, 1H) 7.60 (s, 1H).

Intermediate 21

(2-Chloro-6-(1-ethoxyvinyl)pyrimidin-4-yl)methyl methanesulfonate

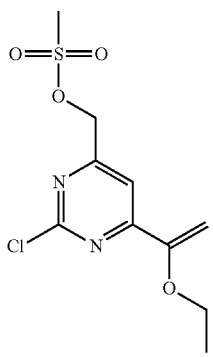 [SMILES: C=C(OCC)c1cc(COS(C)(=O)=O)nc(Cl)n1]

Methanesulfonyl chloride (0.369 mL, 4.73 mmol) was added to an ice-cold solution of (2-chloro-6-(1-ethoxyvinyl)pyrimidin-4-yl)methanol (846 mg, 3.94 mmol) in DCM (8 mL) containing N,N-diisopropylethylamine (1.0 mL, 5.91 mmol). The mixture was stirred at 0° C. for 10 min. DCM (30 mL) was added and the mixture was washed with water (5 mL). The organic phase was dried over sodium sulfate, filtered and the solvent was evaporated to give the title compound (2-chloro-6-(1-ethoxyvinyl)pyrimidin-4-yl)methyl methanesulfonate (1249 mg, quant.).

MS (ES$^+$) m/z 293 [M+H]$^+$.

Intermediate 22

2-Chloro-4-(((3,3-difluorocyclobutyl)methoxy)methyl)-6-(1-ethoxyvinyl)pyrimidine

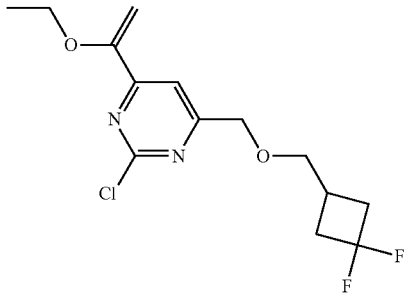 [SMILES: C=C(OCC)c1cc(COCC2CC(F)(F)C2)nc(Cl)n1]

To a solution of (2-chloro-6-(1-ethoxyvinyl)pyrimidin-4-yl)methyl methanesulfonate (0.5 g, 1.71 mmol) in benzene (8 mL) were added (3,3-difluorocyclobutyl)methanol (0.313 g, 2.56 mmol), sodium hydroxide (aq, 5 M, 0.512 mL, 2.56 mmol) and tetrabutylammonium hydrogen sulfate (0.058 g, 0.17 mmol). The mixture was stirred vigorously at rt for 72 h. The mixture was extracted with diethylether. The organic phase was washed with 50% brine, dried over magnesium sulfate and the solvent was evaporated to give 484 mg crude product. 123 mg material from a different batch synthesized using the same method was added. The residue was purified by column chromatography on silica eluting with a gradient of EtOAc in heptane to give the title compound as a gum (0.110 g, 20%).

MS (ES$^+$) m/z 215 [M+H]$^+$. $^1$H NMR (500 MHz, CHLOROFORM-d) δ ppm 1.45 (t, 3H) 2.41-2.55 (m, 3H) 2.64-2.76 (m, 2H) 3.63 (d, 2H) 3.94-4.01 (m, 2H) 4.59 (d, 1H) 4.61 (s, 2H) 5.73 (d, 1H) 7.72 (s, 1H).

Intermediate 23

4-(((3,3-Difluorocyclobutyl)methoxy)methyl)-6-(1-ethoxyvinyl)-N-(3-methoxy-4-(4-methyl-1H-imidazol-1-yl)phenyl)pyrimidin-2-amine

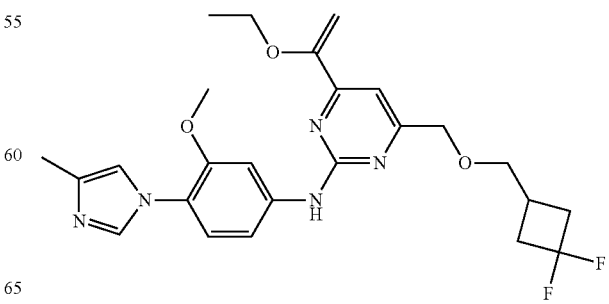

A mixture of 2-chloro-4-(((3,3-difluorocyclobutyl)methoxy)methyl)-6-(1-ethoxyvinyl)pyrimidine (0.048 g, 0.15 mmol), 3-methoxy-4-(4-methyl-1H-imidazol-1-yl)aniline (0.031 g, 0.15 mmol), cesium carbonate (0.098 g, 0.30 mmol), palladium (II) acetate (5 mg, 0.02 mmol) and (2-biphenylyl)dicyclohexylphosphine (8 mg, 0.02 mmol) in dioxane (2 mL) was heated under argon at 120° C. for 90 minutes in micro wave reactor. The mixture was filtered through a short silica and was eluted with EtOAc. The residue was purified by preparative HPLC to give the title compound (0.019 g, 26.0%).

MS (ES$^+$) m/z 215 [M+H]$^+$.

Intermediate 24

1-(6-(((3,3-Difluorocyclobutyl)methoxy)methyl)-2-(3-methoxy-4-(4-methyl-1H-imidazol-1-yl)phenylamino)pyrimidin-4-yl)ethanone

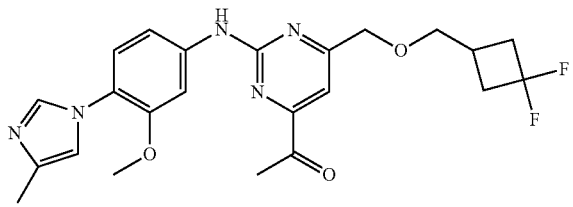 [SMILES: COc1cc(Nc2nc(COCC3CC(F)(F)C3)cc(C(C)=O)n2)ccc1-n1cnc(C)c1]

To a solution of 4-(((3,3-difluorocyclobutyl)methoxy)methyl)-6-(1-ethoxyvinyl)-N-(3-methoxy-4-(4-methyl-1H-imidazol-1-yl)phenyl)pyrimidin-2-amine (17 mg, 0.04 mmol) in dioxane (3 mL) was added water (0.2 mL) and HCl (9 μL, 0.11 mmol). The mixture was stirred at 50° C. for 20 minutes. The solvents were evaporate and the residue was partitioned between aqueous sodium bicarbonate and DCM. The organic phase was evaporated to give the title compound (16 mg, 100%).

MS (ES$^+$) m/z 458 [M+H]$^+$.

Intermediate 25

4-(((3,3-Difluorocyclobutyl)methoxy)methyl)-6-(1-ethoxyvinyl)-N-(3-methoxy-4-(6-methylpyridazin-4-yl)phenyl)pyrimidin-2-amine

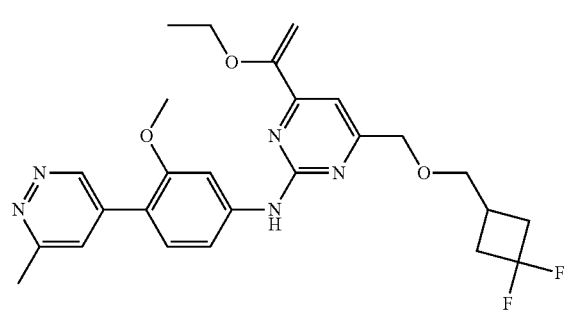 [SMILES: C=C(OCC)c1cc(COCC2CC(F)(F)C2)nc(Nc2ccc(-c3cnnc(C)c3)c(OC)c2)n1]

A mixture of 2-chloro-4-(((3,3-difluorocyclobutyl)methoxy)methyl)-6-(1-ethoxyvinyl)pyrimidine (0.068 g, 0.21 mmol), 3-methoxy-4-(6-methylpyridazin-4-yl)aniline (0.046 g, 0.21 mmol), cesium carbonate (0.139 g, 0.43 mmol), palladium (II) acetate (7 mg, 0.03 mmol) and (2-biphenylyl)dicyclohexylphosphine (0.011 g, 0.03 mmol) in dioxane (2 mL) was heated under argon at 120° C. for 90 min in microwave reactor. The mixture was filtered through a short silica plug and was eluted with 10% MeOH in EtOAc. The solvents were evaporated to give the title compound (0.109 g, quant).

MS (ES$^+$) m/z 498 [M+H]$^+$.

Intermediate 26

1-(6-(((3,3-Difluorocyclobutyl)methoxy)methyl)-2-(3-methoxy-4-(6-methylpyridazin-4-yl)phenylamino)pyrimidin-4-yl)ethanone

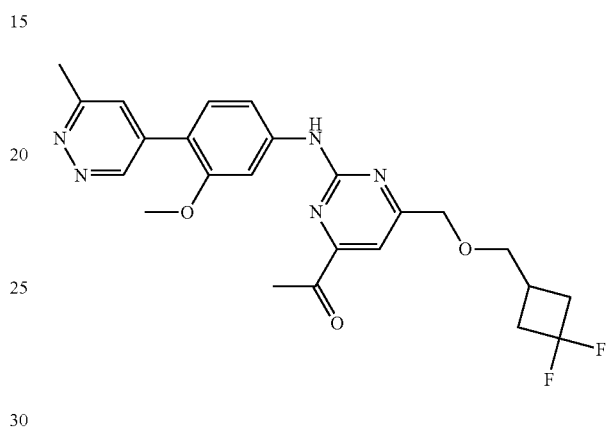

To a solution of 4-(((3,3-difluorocyclobutyl)methoxy)methyl)-6-(1-ethoxyvinyl)-N-(3-methoxy-4-(6-methylpyridazin-4-yl)phenyl)pyrimidin-2-amine (104 mg, 0.21 mmol) in dioxane (15 mL) were added water (1 mL) and HCl (conc. 0.052 mL, 0.63 mmol). The mixture was stirred at 50° C. for 20 minutes. The solvent was evaporate and 50% saturated aqueous sodium bicarbonate solution was added. The mixture was extracted with DCM. The organic phase was separated on phase separator and evaporated to give the title compound (94 mg, 95%).

MS (ES$^+$) m/z 470 [M+H]$^+$.

Intermediate 27

2-Chloro-4-((1,3-difluoropropan-2-yloxy)methyl)-6-(1-ethoxyvinyl)pyrimidine

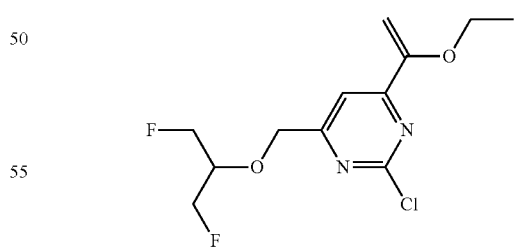

To a solution of (2-chloro-6-(1-ethoxyvinyl)pyrimidin-4-yl)methyl methanesulfonate (0.50 g, 1.71 mmol) in benzene (10 mL), was added 1,3-difluoro-2-propanol (0.246 g, 2.56 mmol). Sodium hydroxide (5M (aq), 0.512 mL, 2.56 mmol) and tetrabutylammonium hydrogen sulfate (0.058 g, 0.17 mmol) were added. The mixture was stirred vigorously at rt over night. The mixture was filtered through a short silica plug with magnesium sulfate. The filter plug was eluted with EtOAc and the solvents were evaporated. The residue was purified by preparative HPLC to give the title compound as a solid (0.054 g, 11%).

MS (ES+) m/z 293 [M+H]+. 1H NMR (400 MHz, CHLOROFORM-d) δ ppm 1.45 (t, 3H) 3.91-4.05 (m, 3H) 4.54-4.59 (m, 3H) 4.66-4.70 (m, 2H) 4.80 (s, 2H) 5.72 (d, 1H) 7.78 (s, 1H).

Intermediate 28

1-(6-((1,3-Difluoropropan-2-yloxy)methyl)-2-(3-methoxy-4-(4-methyl-1H-imidazol-1-yl)phenylamino)pyrimidin-4-yl)ethanone

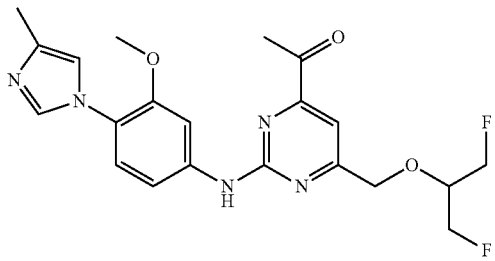 [SMILES: COc1cc(Nc2nc(COC(CF)CF)cc(C(C)=O)n2)ccc1-n1cnc(C)c1]

To a solution of 4-((1,3-difluoropropan-2-yloxy)methyl)-6-(1-ethoxyvinyl)-N-(3-methoxy-4-(4-methyl-1H-imidazol-1-yl)phenyl)pyrimidin-2-amine (47 mg, 0.10 mmol) in dioxane (7.5 mL) was added water (0.5 mL) and HCl (conc., 0.025 mL, 0.31 mmol). The mixture was stirred at 50° C. for 20 minutes. The solvents were evaporated. Sodium bicarbonate solution (50% saturated) was added and the mixture was extracted with DCM. The organic phase was separated on phase separator and evaporated to give the title compound (34 mg, 77%).

MS (ES+) m/z 432 [M+H]+.

Intermediate 29

N-Benzyl-2-chloro-N-methyl-6-((2,2,2-trifluoroethoxy)methyl)pyrimidin-4-amine

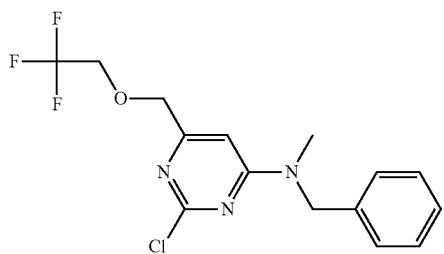 [SMILES: CN(Cc1ccccc1)c1cc(COCC(F)(F)F)nc(Cl)n1]

To a solution of 2,4-dichloro-6-((2,2,2-trifluoroethoxy)methyl)pyrimidine (200 mg, 0.77 mmol) in acetonitrile (3 mL) was benzylmethylamine (0.296 mL, 2.30 mmol) added. The reaction was stirred at ambient temperature for 30 minutes. The solvent was evaporated. The mixture was purified by preparative HPLC the title compound (194 mg, 73%).

MS (ES+) m/z 346 [M+H]+.

Intermediate 30

4-(Azetidin-1-yl)-2-chloro-6-((cyclopropylmethoxy)methyl)pyrimidine

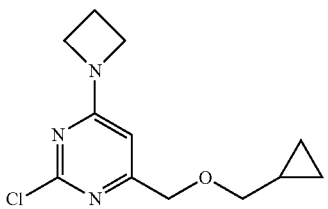 [SMILES: Clc1nc(COCC2CC2)cc(N2CCC2)n1]

To a mixture of azetidine (93 mg, 0.99 mmol) and sodium methoxide (30 wt % in methanol, 0.135 mL, 0.73 mmol) in acetonitrile (6 mL) was added 2,4-dichloro-6-((cyclopropylmethoxy)-methyl)pyrimidine (77 mg, 0.33 mmol). The reaction was stirred at rt for 30 minutes. The mixture was purified by preparative HPLC to give the title compound (44 mg, 53%).

MS (ES+) m/z 254 [M+H]+.

Intermediate 31

2-Chloro-4-(1-ethoxyvinyl)-6-((3,3,3-trifluoropropoxy)methyl)pyrimidine

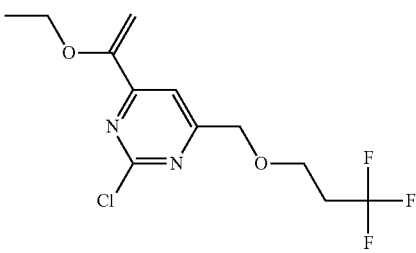 [SMILES: C=C(OCC)c1cc(COCCC(F)(F)F)nc(Cl)n1]

To a solution of (2-chloro-6-(1-ethoxyvinyl)pyrimidin-4-yl)methyl methanesulfonate (0.452 g, 1.54 mmol) in benzene (7 mL) were added 3,3,3-trifluoropropan-1-ol (0.264 g, 2.32 mmol), sodium hydroxide (5 M, 0.463 mL, 2.32 mmol) and tetrabutylammonium hydrogen sulfate (0.052 g, 0.15 mmol). The mixture was stirred vigourously over night at room temperature. The mixture was filtered through a short silica plug with magnesium sulfate on top. The filter was washed with EtOAc. The mixture was purified by preparative HPLC to give 2-chloro-4-(1-ethoxyvinyl)-6-((3,3,3-trifluoropropoxy)methyl)pyrimidine 0.055 g 11%).

MS (ES+) m/z 311 [M+H]+.

Intermediate 32

4-(1-ethoxyvinyl)-N-(3-methoxy-4-(4-methyl-1H-imidazol-1-yl)phenyl)-6-((3,3,3-trifluoropropoxy)methyl)pyrimidin-2-amine

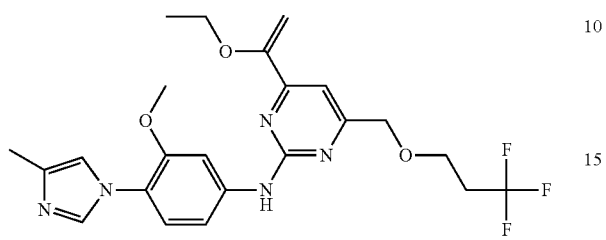

A mixture of 2-chloro-4-(1-ethoxyvinyl)-6-((3,3,3-trifluoropropoxy)methyl)pyrimidine (89 mg, 0.29 mmol), 3-methoxy-4-(4-methyl-1H-imidazol-1-yl)aniline (58 mg, 0.29 mmol), cesium carbonate (187 mg, 0.57 mmol), palladium (II) acetate (10 mg, 0.04 mmol) and (2-biphenylyl)dicyclohexylphosphine (15 mg, 0.04 mmol) in dioxane (3 mL) was heated at 120° C. under argon for 90 minutes in microwave reactor. The mixture was passed through a short silica plug which was eluted with EtOAc. The residue was purified by preparative HPLC to give the title compound as a dry film 93 mg (68%).

MS (ES$^+$) m/z 478 [M+H]$^+$.

Intermediate 33

1-(2-(3-Methoxy-4-(4-methyl-1H-imidazol-1-yl)phenylamino)-6-((3,3,3-trifluoropropoxy)methyl)pyrimidin-4-yl)ethanone

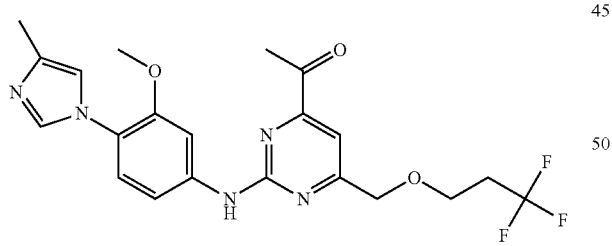

To a solution of 4-(1-ethoxyvinyl)-N-(3-methoxy-4-(4-methyl-1H-imidazol-1-yl)phenyl)-6-((3,3,3-trifluoropropoxy)methyl)pyrimidin-2-amine (93 mg, 0.19 mmol) in dioxane (13.5 mL) was added water (0.9 mL) and HCl (0.048 mL, 0.58 mmol). The mixture was stirred at 50° C. for 20 minutes. The solvents were evaporated. Sodium bicarbonate (aq, 50% saturated) was added and the mixture was extracted with DCM. The organic phase was separated on phase separator and evaporated to give the title compound as a gum, 85 mg (97%).

MS (ES$^+$) m/z 450 [M+H]$^+$.

Intermediate 34

2-Chloro-4-(4,4-difluoropiperidin-1-yl)-6-((2,2,2-trifluoroethoxy)methyl)pyrimidine

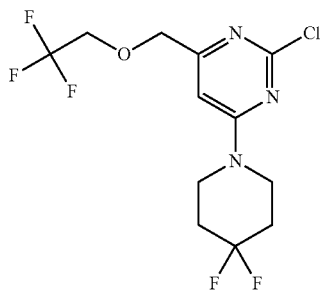 [SMILES: FC(F)(F)COCc1cc(N2CCC(F)(F)CC2)nc(Cl)n1]

To an ice-cold solution of 2,4-dichloro-6-((2,2,2-trifluoroethoxy)methyl)pyrimidine (0.120 g, 0.46 mmol) in acetonitrile (2 mL) was a solution of 4,4-difluoropiperidine (0.217 g, 1.38 mmol) and sodium methoxide (30 wt % in methanol, 0.188 mL, 1.01 mmol) in MeOH (2 mL) added. The reaction was stirred at 0° C. for 2 hours. Water and DMF was added and the residue was purified by preparative HPLC to give the title compound as a dry film (0.110 g, 69%).

MS (ES$^+$) m/z 346 [M+H]$^+$. $^1$H NMR (500 MHz, CHLOROFORM-d) δ ppm 2.01-2.12 (m, 4H) 3.84 (br. s, 4H) 3.98 (q, 2H) 4.60 (s, 2H) 6.65 (s, 1H).

Intermediate 35

2-Chloro-N-isopropyl-6-((2,2,2-trifluoroethoxy)methyl)pyrimidin-4-amine

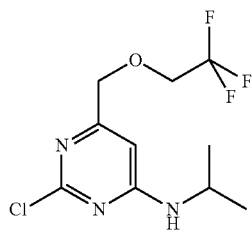 [SMILES: CC(C)Nc1cc(COCC(F)(F)F)nc(Cl)n1]

A solution of isopropylamine (0.10 mL, 1.20 mmol) in MeOH (2 mL) was added dropwise to a ice-cold solution of 2,4-dichloro-6-((2,2,2-trifluoroethoxy)methyl)pyrimidine (104 mg, 0.40 mmol) in acetonitrile (2 mL). The mixture was stirred at rt overnight. The residue was purified by preparative HPLC to give the title compound as a dry film, 63 mg (56%).

MS (ES$^+$) m/z 284 [M+H]$^+$. $^1$H NMR (500 MHz, CHLOROFORM-d) δ 1.21-1.34 (m, 7H), 3.98 (q, J=8.51 Hz, 2H), 4.62 (s, 2H), 6.42 (br. s, 1H).

Intermediate 36

2-Chloro-N-(2-methoxyethyl)-6-((2,2,2-trifluoroethoxy)methyl)pyrimidin-4-amine

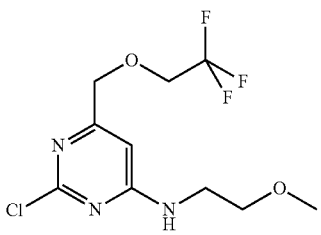 [SMILES: COCCNc1cc(COCC(F)(F)F)nc(Cl)n1]

A solution of 2-methoxyethanamine (59 μl, 0.69 mmol) in MeOH (2 mL) was added dropwise to an ice-cold solution of 2,4-dichloro-6-((2,2,2-trifluoroethoxy)methyl)pyrimidine (66 mg, 0.25 mmol) in acetonitrile (2 mL). The reaction was stirred at rt over night. The reaction mixture was concentrated in vacuo and the crude was purified by preparative HPLC to give the title compound as a solid, 43 mg (57%).

MS (ES$^+$) m/z 300 (M+H)$^+$. $^1$H NMR (500 MHz, CHLOROFORM-d) δ ppm 3.40 (s, 3H) 3.48-3.75 (m, 4H) 3.97 (q, 2H) 4.62 (s, 2H) 6.47 (br. s, 1H).

Intermediate 37

3-(2-Chloro-6-((2,2,2-trifluoroethoxy)methyl)pyrimidin-4-ylamino)propanenitrile

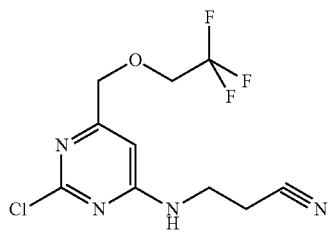 [SMILES: N#CCCNc1cc(COCC(F)(F)F)nc(Cl)n1]

A solution of 3-aminopropanenitrile fumarate (147 mg, 0.74 mmol) and sodium methoxide (1.1 mL, 0.54 mmol) in MeOH (2 mL) was added dropwise to an ice-cold solution of 2,4-dichloro-6-((2,2,2-trifluoroethoxy)methyl)pyrimidine (64 mg, 0.25 mmol) in acetonitrile (2 mL). The mixture stirred at rt over night. The mixture was heated to 50° C. for 20 h. The reaction mixture was concentrated in vacuo and the crude was partitioned between EtOAc and 1M NaOH. The organic layer was concentrated in vacuo and the residue was purified by preparative HPLC to give the title compound, 29 mg (40%).

MS (ES$^+$) m/z 295 (M+H)$^+$. NMR: $^1$H NMR (500 MHz, CHLOROFORM-d) δ ppm 2.78 (t, 2H) 3.78 (d, 2H) 3.98 (q, 2H) 4.60 (s, 2H) 5.44 (br. s, 1H) 6.53 (s, 1H).

Intermediate 38

Ethyl 2-(3-methoxy-4-(6-methylpyridazin-4-yl)phenylamino)-6-((2,2,2-trifluoroethoxy)-methyl)pyrimidine-4-carboxylate

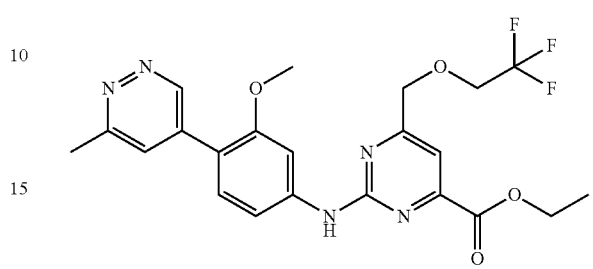

4-(1-Ethoxyvinyl)-N-(3-methoxy-4-(6-methylpyridazin-4-yl)phenyl)-6-((2,2,2-trifluoroethoxy)-methyl)pyrimidin-2-amine (0.7 g, 1.47 mmol) was dissolved in 1,4-dioxane (50 mL). Sodium metaperiodate (0.630 g, 2.94 mmol) was suspended in water (25 mL) and sonicated until a clear solution was obtained then added to the dioxane-solution. Potassium permanganate (0.035 g, 0.22 mmol) was added and the mixture was stirred at rt. Additional 10-15 mg of potassium permangante was added every 10 min. After 45 min the reaction mixture was filtered and the filter was washed with EtOAc. To the filtrate were sodium bicarbonate (s) and sodium chloride (s) added and the mixture was stirred for 5 min. The phases were separated and aqueous layer was extracted with ethyl acetate (×2). The combined organic layer was dried over sodium sulfate, filtrated and evaporated. The residue was purified by column chromatography on silica eluting with a gradient of methanol in DCM to give the title compound as a solid, 595 mg (85%).

MS (ES$^+$) m/z 478 [M+H]$^+$. $^1$H NMR (500 MHz, CHLOROFORM-d) δ ppm 1.46 (t, 3H) 2.78 (s, 3H) 3.95 (s, 3H) 4.04 (q, 2H) 4.50 (q, 2H) 4.78 (s, 2H) 7.10 (dd, 1H) 7.37 (d, 1H) 7.55 (s, 2H) 7.61 (s, 1H) 7.97 (br. s, 1H) 9.29 (d, 1H).

Intermediate 39

2-(3-Methoxy-4-(6-methylpyridazin-4-yl)phenylamino)-6-((2,2,2-trifluoroethoxy)methyl)-pyrimidine-4-carbaldehyde

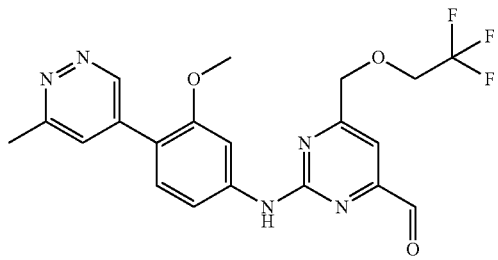 [SMILES: COc1cc(Nc2nc(C=O)cc(COCC(F)(F)F)n2)ccc1-c1cnnc(C)c1]

Ethyl 2-(3-methoxy-4-(6-methylpyridazin-4-yl)phenylamino)-6-((2,2,2-trifluoroethoxy)methyl)-pyrimidine-4-carboxylate (595 mg, 1.25 mmol) was dissolved in dichloromethane (25 mL) under nitrogen atmosphere and cooled at −78° C. Diisobutyl aluminum hydride (1 M in hexane, 4.36 mL, 4.36 mmol) was added over 10 min. After 1 h diisobutyl aluminum hydride (1 M in hexane, 1.4 mL) was added and the mixture was stirred for 2 h. MeOH (3 mL) was added and the mixture was let to rt. Water (5 mL) was added. The slurry was stirred for 20 min and filtrated through a plug of diatomeous earth. The filter plug was washed with 10% MeOH in DCM. The phases were separated and the aqueous phase was extracted with DCM. The combined organic layer was dried over sodium sulfate, filtered and concentrated onto silica. The residue was purified by column chromatography on silica eluting with a gradient of methanol in dichloromethane to give the title compound as a solid, 270 mg (50%).

MS (ES$^+$) m/z 466 [M+H]$^+$. $^1$H NMR (400 MHz, CHLOROFORM-d) δ ppm 2.84 (s, 3H) 3.96 (s, 3H) 4.00-4.09 (m, 2H) 4.78 (s, 2H) 7.10 (s, 1H) 7.41 (s, 1H) 7.48 (s, 1H) 7.54 (s, 1H) 7.66 (br. s, 1H) 7.82 (s, 1H) 9.33 (s, 1H) 9.98 (s, 1H).

Intermediate 40

4-(1-Ethoxyvinyl)-N-(3-methoxy-4-(6-methylpyridazin-4-yl)phenyl)-6-((2,2,2-trifluoroethoxy)methyl)pyrimidin-2-amine

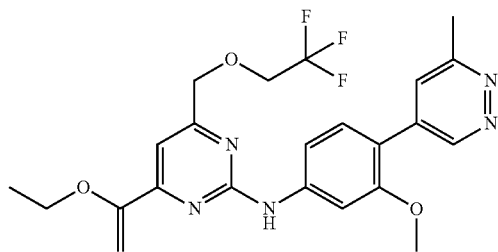 [SMILES: C=C(OCC)c1cc(COCC(F)(F)F)nc(Nc2ccc(-c3cnnc(C)c3)c(OC)c2)n1]

2-Chloro-4-(1-ethoxyvinyl)-6-((2,2,2-trifluoroethoxy)methyl)pyrimidine (0.70 g, 2.36 mmol), 3-methoxy-4-(6-methylpyridazin-4-yl)aniline (0.508 g, 2.36 mmol), cesium carbonate (1.538 g, 4.72 mmol), palladium(II) acetate (0.079 g, 0.35 mmol) and 2-(dicyclohexylphosphino)biphenyl (0.124 g, 0.35 mmol) were mixed in dioxane (16 mL). The vial was capped, evacuated and flushed with nitrogen. The reaction mixture was heated at 120° C. for 1.5 h. The mixture was filtered and the filter was washed with mixtures of methanol and DCM. The filtrate was concentrated. The residue was purified by column chromatography on silica column eluting with a gradient of methanol and DCM to give the title compound as a solid 702 mg (63%).

MS (ES$^+$) m/z 476 [M+H]$^+$. $^1$H NMR (500 MHz, CHLOROFORM-d) δ ppm 1.47 (t, 3H) 2.87 (s, 3H) 3.96 (s, 3H) 3.97-4.06 (m, 4H) 4.53 (d, 1H) 4.71 (s, 2H) 5.62 (d, 1H) 7.12-7.17 (m, 1H) 7.32 (s, 1H) 7.41 (d, 2H) 7.66-7.77 (m, 1H) 7.89-7.95 (m, 1H) 9.35 (d, 1H).

Intermediate 41

(2-Chloro-6-((2,2,2-trifluoroethoxy)methyl)pyrimidin-4-yl)methanol

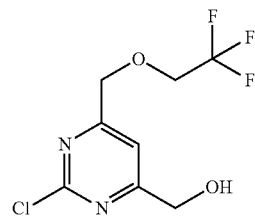 [SMILES: OCc1cc(COCC(F)(F)F)nc(Cl)n1]

2-Chloro-6-((2,2,2-trifluoroethoxy)methyl)pyrimidine-4-carbaldehyde (0.6 g, 2.36 mmol) was dissolved in ethanol (20 mL). Sodium borohydride (0.134 g, 3.54 mmol) was added and the mixture was stirred at rt for 10 min. Acetone (5 mL) was added and mixture was stirred for 10 min. Chloroform (20 mL) was added and the mixture was filtered through a pad of silica. The solvents were evaporated and the residue was purified by column chromatography on silica eluting with a gradient of methanol in DCM to give the title compound 0.35 g (58%).

MS (APCI$^+$) m/z 257 (M+H)$^+$. $^1$H NMR (400 MHz, CHLOROFORM-d) δ ppm 3.41 (br. s, 1H) 4.00 (q, 2H) 4.75 (s, 2H) 4.78 (s, 2H) 7.55 (s, 1H).

Intermediate 42

(2-Chloro-6-((2,2,2-trifluoroethoxy)methyl)pyrimidin-4-yl)methyl methanesulfonate

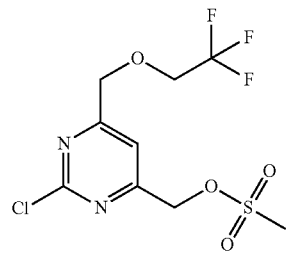 [SMILES: CS(=O)(=O)OCc1cc(COCC(F)(F)F)nc(Cl)n1]

A solution of methanesulfonyl chloride (0.13 mL, 1.64 mmol) in DCM (2 mL) was cooled at −30° C. (2-Chloro-6-((2,2,2-trifluoroethoxy)methyl)pyrimidin-4-yl)methanol (0.35 g, 1.36 mmol) and N,N-diisopropylethylamine (0.45 mL, 2.73 mmol) in DCM (15 mL) were added. The mixture was stirred for 10 min. Brine (50%, 50 mL) was added. The organic phase was isolated using a phase separator containing sodium sulfate. The solvents were evaporated to give the title compound 0.47 g (quant).

MS (APCI+) m/z 335 (M+H)$^+$.

Intermediate 43

4-(1-Ethoxyvinyl)-N-(3-methoxy-4-(4-methoxy-1H-imidazol-1-yl)phenyl)-6-((2,2,2-trifluoroethoxy)methyl)pyrimidin-2-amine

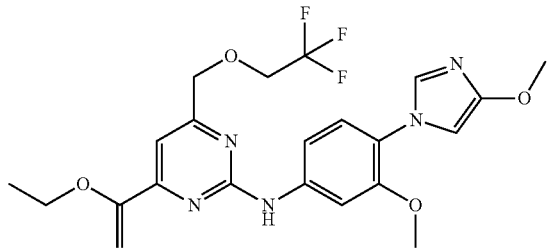 [SMILES: C=C(OCC)c1cc(COCC(F)(F)F)nc(Nc2ccc(-n3cnc(OC)c3)c(OC)c2)n1]

2-Chloro-4-(1-ethoxyvinyl)-6-((2,2,2-trifluoroethoxy)methyl)pyrimidine (0.230 g, 0.78 mmol), 3-methoxy-4-(4-methoxy-1H-imidazol-1-yl)aniline, palladium(II) acetate (0.026 g, 0.12 mmol), 2-(dicyclohexylphosphino)biphenyl (0.041 g, 0.12 mmol), cesium carbonate (0.505 g, 1.55 mmol) and dioxane (20 mL) were mixed in a vial. The vial was capped, evacuated and flushed with nitrogen. The mixture was heated by microwave irradiation at 120° C. for 1.5 h. The mixture was filtrated through pad of silica and silica was washed by EtOAc containing 10% of MeOH. The solvents were evaporated and the residue was purified by column chromatography eluting with gradient of MeOH and DCM to give the title compound as a dry film, 0.313 g (84%).

MS (APCI⁺) m/z 480.3 (M+H)⁺. ¹H NMR (400 MHz, CHLOROFORM-d): δ=7.83 (d, 1H), 7.41 (d, 1H), 7.33 (s, 1H), 7.27 (s, 1H), 7.19 (d, 1H), 7.04 (dd, 1H), 6.49 (d, 1H), 5.59 (d, 1H), 4.69 (s, 2H), 4.50 (d, 1H), 4.00 (q, 2H), 3.97 (q, 2H), 3.89 (s, 3H), 3.87 (s, 3H), 1.46 ppm (t, 4H).

Intermediate 44

1-(2-(3-Methoxy-4-(4-methoxy-1H-imidazol-1-yl)phenylamino)-6-((2,2,2-trifluoroethoxy)-methyl)pyrimidin-4-yl)ethanone

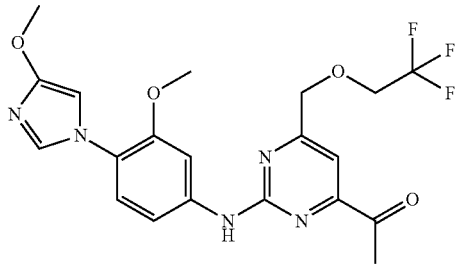 [SMILES: COc1cn(-c2ccc(Nc3nc(COCC(F)(F)F)cc(C(C)=O)n3)cc2OC)cn1]

4-(1-Ethoxyvinyl)-N-(3-methoxy-4-(4-methoxy-1H-imidazol-1-yl)phenyl)-6-((2,2,2-trifluoro-ethoxy)methyl)pyrimidin-2-amine (0.31 g, 0.65 mmol) was dissolved in dioxane (30 mL) and water (3 mL). Hydrochloric acid (conc., 0.164 mL, 1.94 mmol) was added. The mixture was heated at 40° C. for 35 min. Sodium bicarbonate (1 g) was added. Brine (5 mL) was added and the mixture was extracted with EtOAc (×2). The combined organic phases were dried over sodium sulfate and evaporated to give the title compound as a solid, 0.28 g (98%).

MS (APCI⁺) m/z 452 (M+H)⁺. ¹H NMR (400 MHz, CHLOROFORM-d): δ 2.72 ppm (s, 3H), 3.89 (s, 3H), 3.91 (s, 3H), 4.02 (q, 3H), 4.74 (s, 2H), 6.51 (d, 1H), 7.15 (dd, 2.3 Hz, 1H), 7.25 (d, 1H), 7.42 (br. s, 1H), 7.45 (d, 1H), 7.73 (d, 1H), 7.50 (s, 1H).

Intermediate 45

4-Methoxy-1H-imidazole

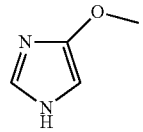

Sodium methoxide (30 wt % in methanol, 3.35 mL, 18.01 mmol) was added over 5 min to a solution of aminoacetonitrile hydrochloride (4.76 g, 51.44 mmol) in MeOH (20 mL). The mixture was stirred 20 for min. The solids were removed by filtration and the solvents were evaporated. Trimethoxymethane (55 g, 514 mmol) and sulfuric acid (4 drops) were added. The mixture was heated at reflux and the methanol was distilled off for 20 min. The mixture was cooled, filtrated and the solvents were evaporated. The residue was dissolved in MeOH (10 mL). Sodium methoxide (30 wt % in methanol, 3.35 mL, 18.0 mmol) was added and mixture was heated at reflux for 2 h. HCl (aq) was added to neutral pH. Potassium carbonate was added to basic pH. The mixture was filtered through a pad of silica. The solvents were evaporated and the residue was purified on a short silica column eluting with DCM/acetone/Et3N 50:50:1. The solvents were evaporated to give the title compound as a solid 0.47 g (9%).

¹H NMR (400 MHz, CHLOROFORM-d): δ 7.31 (d, 1H), 6.34 (d, 1H), 3.83 ppm (s, 4H).

Intermediate 46

4-Methoxy-1-(2-methoxy-4-nitrophenyl)-1H-imidazole

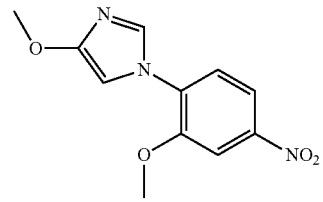 [SMILES: COc1cn(-c2ccc([N+](=O)[O-])cc2OC)cn1]

1-Fluoro-2-methoxy-4-nitrobenzene (0.785 g, 4.59 mmol), 4-methoxy-1H-imidazole (0.45 g, 4.59 mmol) and potassium carbonate (0.697 g, 5.05 mmol) were mixed in dry acetonitrile (10 mL) and heated at 90° C. for 4 days. DCM was added and the mixture was filtrated through a pad of silica eluting with 5% MeOH in DCM. The solvents were evaporated and mixture was purified by column chromatography in silica eluting with a gradient of MeOH and DCM to give the title compound as a gum 0.62 g (54%).

MS (APCI+) m/z 250 (M+H)+. ¹H NMR (500 MHz, CHLOROFORM-d): δ 3.89 ppm (s, 3H), 4.01 (s, 3H), 6.60 (d, 1H), 7.44 (d, 1H), 7.65 (d, 1H), 7.89-8.01 (m, 2H).

Intermediate 47

3-Methoxy-4-(4-methoxy-1H-imidazol-1-yl)aniline

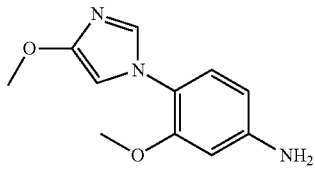 [SMILES: COc1cn(-c2ccc(N)cc2OC)cn1]

4-Methoxy-1-(2-methoxy-4-nitrophenyl)-1H-imidazole (0.62 g, 2.49 mmol) was dissolved in EtOH (20 mL). Palladium on carbon (10%, 0.106 g, 0.10 mmol) was added. The mixture was shaken for 2 hours under an atmosphere of hydrogen (g). The mixture was filtered, the filter was washed with warm EtOH. The filtrate was concentrated to give the title compound as an oil, 0.52 g (95%).

MS (APCI+) m/z 220 (M+H)+. ¹H NMR (500 MHz, CHLOROFORM-d): δ 3.77 (s, 3H), 3.85 (s, 3H), 6.28 (dd, 1H), 6.32 (d, 1H), 6.41 (d, 1H), 7.01 (d, 1H), 7.30 (d, 1H).

Intermediate 48

2-Chloro-N-(cyclopropylmethyl)-6-((2,2,2-trifluoroethoxy)methyl)pyrimidin-4-amine

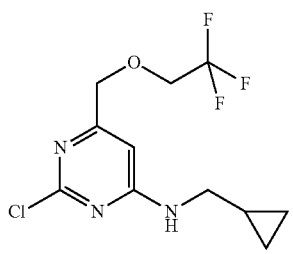 [SMILES: FC(F)(F)COCc1cc(NCC2CC2)nc(Cl)n1]

A solution of cyclopropylmethanamine (91 mg, 1.28 mmol) a in MeOH (2 mL) was added to an ice-cold solution of 2,4-dichloro-6-((2,2,2-trifluoroethoxy)methyl)pyrimidine (111 mg, 0.43 mmol) in acetonitrile (2 mL). The mixture was stirred at ambient temperature overnight. The solution was concentrated and purified by preparative HPLC to give the title compound as a solid, 72 mg (58%).

MS (ES+) m/z 296 (M+H)+. ¹H NMR (500 MHz, CHLOROFORM-d) δ ppm 0.30 (d, J=5.67 Hz, 2H), 0.62 (d, 2H), 1.01-1.14 (m, 1H), 1.26 (s, 1H), 3.98 (q, 2H), 4.62 (s, 2H), 6.44 (s, 1H).

Intermediate 49

2-Chloro-N-cyclopropyl-6-((2,2,2-trifluoroethoxy)methyl)pyrimidin-4-amine

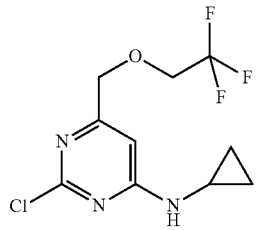 [SMILES: FC(F)(F)COCc1cc(NC2CC2)nc(Cl)n1]

A solution of cyclopropanamine (68 mg, 1.20 mmol) in MeOH (2 mL) was added dropwise to an ice-cold solution of 2,4-dichloro-6-((2,2,2-trifluoroethoxy)methyl)pyrimidine (104 mg, 0.40 mmol) in acetonitrile (2 mL). The mixture was stirred at rt overnight. The mixture was purified by preparative HPLC yielding to give the title compound (64 mg, 57%).

MS (ES+) m/z 282 (M+H)+. ¹H NMR (500 MHz, CHLOROFORM-d) ⊠ 0.54-0.69 (m, 2H), 0.92 (dd, 2H), 2.61 (br. s, 1H), 3.99 (d, 2H), 4.63 (s, 2H), 6.79 (br. s, 1H).

Intermediate 50

2-Chloro-N-(oxetan-3-yl)-6-((2,2,2-trifluoroethoxy)methyl)pyrimidin-4-amine

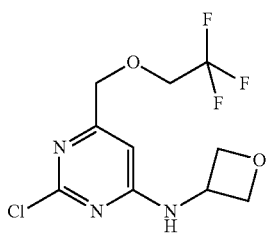 [SMILES: FC(F)(F)COCc1cc(NC2COC2)nc(Cl)n1]

A solution of oxetan-3-amine (77 mg, 1.06 mmol) in MeOH (2 mL) was added dropwise to an ice-cold solution of 2,4-dichloro-6-((2,2,2-trifluoroethoxy)methyl)pyrimidine (92 mg, 0.35 mmol) in acetonitrile (2 mL). The mixture stirred at rt overnight. The mixture was separated by preparative chromatography to give the title compound (58 mg, 55%).

MS (ES+) m/z 298 (M+H)+. ¹H NMR (500 MHz, CHLOROFORM-d) ⊠ 3.97 (q, 2H), 4.54-4.62 (m, 4H), 5.02 (t, 2H), 5.54 (br. s, 1H), 6.43 (br. s, 1H).

Intermediate 51

1-(2-Chloro-6-((2,2,2-trifluoroethoxy)methyl)pyrimidin-4-ylamino)-2-methylpropan-2-ol

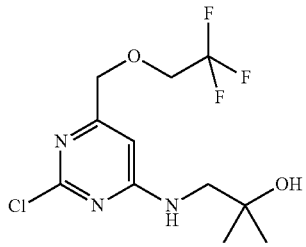 [SMILES: CC(C)(O)CNc1cc(COCC(F)(F)F)nc(Cl)n1]

1-Amino-2-methylpropan-2-ol hydrochloride (221 mg, 1.76 mmol) was suspended in MeOH (2 mL). Triethylamine (0.147 mL, 1.06 mmol) was added and the suspension was filtered. The filtrate was added to an ice-cold solution of 2,4-dichloro-6-((2,2,2-trifluoroethoxy)methyl)-pyrimidine (92 mg, 0.35 mmol) in acetonitrile (2 mL). The mixture was stirred for 1 h at rt. The mixture was purified by preparative HPLC to give the title compound (35 mg, 32%).

MS (ES$^+$) m/z 314 (M+H)$^+$. $^1$H NMR (500 MHz, CHLOROFORM-d) ⍰ 1.31 (s, 6H), 1.77 (br. s, 2H), 3.97 (q, 2H), 4.58 (s, 2H), 6.47 (s, 1H).

Intermediate 52

2-Chloro-4-((cyclopropylmethoxy)methyl)-6-((2,2,2-trifluoroethoxy)methyl)pyrimidine

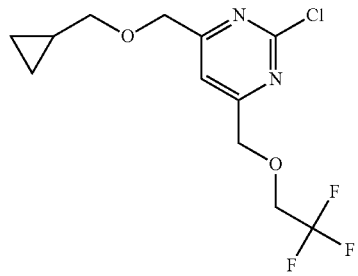 [SMILES: FC(F)(F)COCc1cc(COCC2CC2)nc(Cl)n1]

(2-Chloro-6-((2,2,2-trifluoroethoxy)methyl)pyrimidin-4-yl)methyl methanesulfonate (0.47 g, 1.40 mmol) was dissolved in benzene (8 mL). Cyclopropylmethanol (0.222 mL, 2.81 mmol), 5 M sodium hydroxide (0.421 mL, 2.11 mmol) and tetrabutylammonium hydrogen sulfate (48 mg, 0.14 mmol) were added. The mixture was stirred vigorously at ambient temperature for 3 h. Solid carbon dioxide was added followed by brine and water. The mixture was extracted twice with ethyl acetate, the organic phase was separated and dried over sodium sulfate. The solution was concentrated in vacuum, and the residue was purified by column chromatography on silica eluting with a gradient of 0-50% of ethyl acetate in heptane. The solvents were evaporated and the residue was purified by preparative HPLC to give the title compound, 33 mg (7.5%).

MS (APCI$^+$) 311 (M+H)$^+$. $^1$H NMR (500 MHz, CHLOROFORM-d): ⍰ ppm 0.22-0.30 (m, 2H), 0.56-0.64 (m, 2H), 1.05-1.18 (m, 1H), 3.44 (d, 2H), 4.01 (q, 2H), 4.63 (s, 2H), 4.76 (s, 2H), 7.67 (s, 1H).

Intermediate 53

2-Chloro-6-((cyclopropylmethoxy)methyl)-N-methylpyrimidin-4-amine

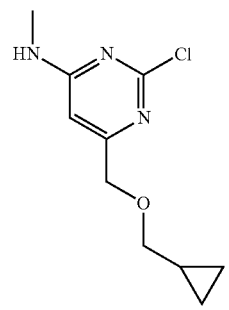

Methanamine (0.124 mL, 0.99 mmol) in EtOH was added to a solution of 2,4-dichloro-6-((cyclopropylmethoxy)methyl)pyrimidine (77 mg, 0.33 mmol) in acetonitrile (6 mL). The mixture was stirred at 0° C. for 30 minutes. The mixture was concentrated and the residue was purified by preparative HPLC give the title compound, 42 mg (56%).

MS (ES$^+$) m/z 229 (M+H)$^+$.

Intermediate 54 and 55

2-Chloro-5-methyl-4-(2,2,2-trifluoroethoxy)-6-((2,2,2-trifluoroethoxy)methyl)pyrimidine and 2,4-dichloro-5-methyl-6-((2,2,2-trifluoroethoxy)methyl)pyrimidine

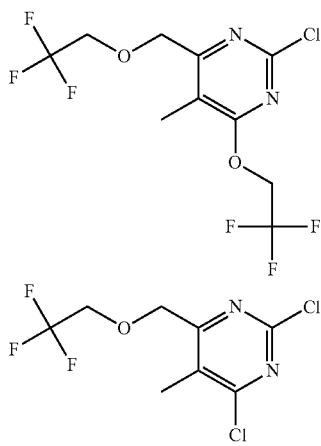

(2,6-Dichloro-5-methylpyrimidin-4-yl)methanol (0.23 g, 1.19 mmol) was coevaporated with dioxane and was dissolved in dichloromethane (5 mL) under nitrogen atmosphere. 2,2,2-Trifluoroethanol (0.86 mL, 11.92 mmol), tributyl phosphine (0.60 mL, 2.38 mmol) and 1,1'-(azodicarbonyl)dipiperidine (0.601 g, 2.38 mmol) were added. The mixture was stirred for 15 min at rt. The solvents were evaporated. Heptane/AcOEt 1:2 (5 mL) was added and the mixture was filtered through a plug of silica. The filter was washed with heptane/EtOAc. The solvents were evaporated and the residue was purified by column chromatography on silica eluting with DCM to give the title compounds:

Intermediate 54 2-chloro-5-methyl-4-(2,2,2-trifluoroethoxy)-6-((2,2,2-trifluoroethoxy)methyl)pyrimidine as a liquid, 120 mg (30%).

MS (APCI+) m/z 339 (M+H)+. 1H NMR (500 MHz, CHLOROFORM-d): δ 2.25 ppm (s, 3H) 3.94 (q, 2H) 4.73 (s, 2H) 4.82 (q, 3H); and Intermediate 54 2,4-dichloro-5-methyl-6-((2,2,2-trifluoroethoxy)methyl)pyrimidine as a liquid, 110 mg (34%).

MS (APCI+) m/z 275 (M+H)+. 1H NMR (500 MHz, CHLOROFORM-d): δ 2.41 ppm (s, 3H) 3.95 (q, 2H) 4.77 (s, 2H).

Intermediate 56

N-(3-Methoxy-4-(4-methyl-1H-imidazol-1-yl)phenyl)-5-methyl-4-(2,2,2-trifluoroethoxy)-6-((2,2,2-trifluoroethoxy)methyl)pyrimidin-2-amine

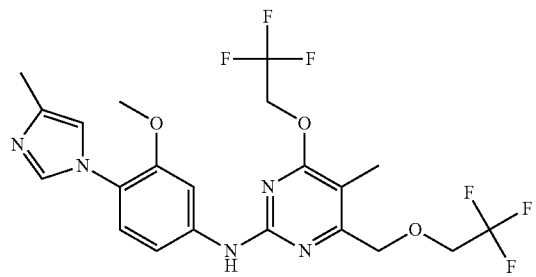 [SMILES: COc1cc(Nc2nc(COCC(F)(F)F)c(C)c(OCC(F)(F)F)n2)ccc1-n1cnc(C)c1]

3-Methoxy-4-(4-methyl-1H-imidazol-1-yl)aniline (0.066 g, 0.32 mmol), 2-chloro-5-methyl-4-(2,2,2-trifluoroethoxy)-6-((2,2,2-trifluoroethoxy)methyl)pyrimidine (0.11 g, 0.32 mmol), palladium(II) acetate (11 mg, 0.05 mmol), 2-(dicyclohexylphosphino)biphenyl (0.017 g, 0.05 mmol) and cesium carbonate (0.212 g, 0.65 mmol) were mixed in dioxane (3 mL). The vial was capped, evacuated and flushed with nitrogen. The mixture was heated by microwave irradiation at 120° C. for 1.5 h. The mixture was filtered and the residue was purified by column chromatography on silica eluting with a gradient of methanol in DCM to give the title compound 135 mg (82%).

MS (ES+) m/z 506 (M+H)+.

Intermediate 57

4-(1-Ethoxyvinyl)-N-(3-methoxy-4-(4-methyl-1H-imidazol-1-yl)phenyl)-5-methyl-6-((2,2,2-trifluoroethoxy)methyl)pyrimidin-2-amine

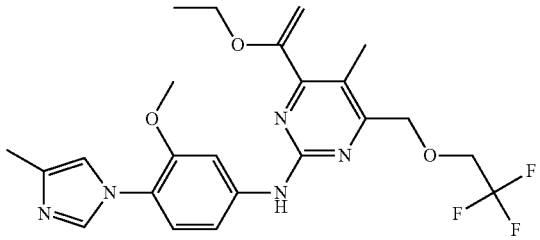 [SMILES: C=C(OCC)c1nc(Nc2ccc(-n3cnc(C)c3)c(OC)c2)nc(COCC(F)(F)F)c1C]

2-Chloro-4-(1-ethoxyvinyl)-5-methyl-6-((2,2,2-trifluoroethoxy)methyl)pyrimidine (70 mg, 0.23 mmol), 3-methoxy-4-(4-methyl-1H-imidazol-1-yl)aniline (46 mg, 0.23 mmol), palladium(II) acetate (8 mg, 0.03 mmol), 2-(dicyclohexylphosphino)biphenyl (12 mg, 0.03 mmol) and cesium carbonate (147 mg, 0.45 mmol) were mixed in dioxane (4 mL). The vial was capped, evacuated and flushed with nitrogen. The reaction mixture was heated by microwave irradiation at 120° C. for 1.5 h. The mixture was filtered through a pad of silica and the silica was washed by 5% of MeOH in DCM. The solvents were evaporated and the residue was purified by preparative HPLC to give the title compound 52 mg (48%).

MS (APCI+) m/z 478 (M+H)+. 1H NMR (500 MHz, CHLOROFORM-d): δ 1.41 (t, 3H) 2.27 (s, 3H) 2.31 (s, 3H) 3.86 (s, 3H) 3.96 (q, 2H) 3.98 (q, 2H) 4.50 (d, 1H) 4.65 (d, 1H) 4.75 (s, 2H) 6.87 (s, 1H) 6.99 (dd, 1H) 7.16 (d, 1H) 7.24 (s, 1H) 7.63 (s, 1H) 7.89 (d, 1H).

Intermediate 58

Ethyl 2-chloro-6-((2,2,2-trifluoroethoxy)methyl)pyrimidine-4-carboxylate

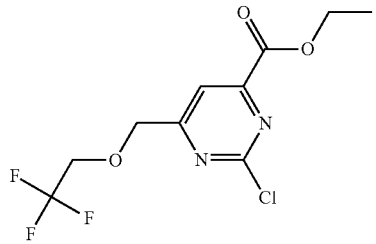 [SMILES: CCOC(=O)c1cc(COCC(F)(F)F)nc(Cl)n1]

Sodium metaperiodate (701 mg, 3.28 mmol) was suspended in water (10 mL) and sonicated until a clear solution was obtained. 2-Chloro-4-(1-ethoxyvinyl)-6-((2,2,2-trifluoroethoxy)methyl)pyrimidine (486 mg, 1.64 mmol) in 1,4-dioxane (20 mL) and potassium permanganate (39 mg, 0.25 mmol) were added and the mixture was stirred at rt for 30 min. The mixture was filtered, precipitate was washed by dioxane and DCM. DCM an solid sodium bicarbonate (s) were added to the filtrate. The mixture was extracted with DCM (×2). The organic phase was dried over sodium sulfate and concentrated. The residue was purified by column chromatography on silica eluting with DC ti give the title compound as a solid, 385 mg (79%).

MS (APCI+) m/z 299 (M+H)+. 1H NMR (500 MHz, CHLOROFORM-d) δ ppm 1.46 (t, 3H), 4.05 (q, 2H), 4.52 (q, 2H), 4.85 (s, 2H), 8.11 (s, 1H).

Intermediate 59

Methyl 2-chloro-6-(1-ethoxyvinyl)pyrimidine-4-carboxylate

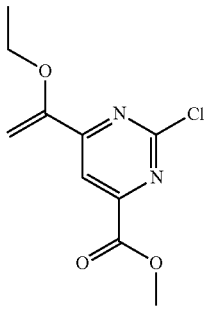 [SMILES: C=C(OCC)c1cc(C(=O)OC)nc(Cl)n1]

Methyl 2,6-dichloropyrimidine-4-carboxylate (8.44 g, 40.77 mmol) and bis(triphenylphosphine)-palladium(II) chloride (0.572 g, 0.82 mmol) in DMF (80 mL) was degased. Tributyl(1-ethoxy-vinyl)tin (14.46 mL, 42.81 mmol) was added under argon. The mixture was heated at 94° C. for 1 h. The mixture was poured into a solution of potassium fluoride (30 g) in water (400 mL). MTBE (300 mL) was added and the mixture was stirred for 10 min. The mixture was filtered and the filter was washed with 200 mL of MTBE. The filtrate was washed with brine (100 mL), dried over sodium sulfate and the solvents were evaporated. The residue purified by column chromatography on silica eluting with DCM to give the title compound as a solid (7.40 g, 75%).

MS (ES$^+$) m/z 243 (M+H)$^+$. $^1$H NMR (500 MHz, CHLOROFORM-d) δ ppm: 1.44 (t, 3H), 3.97 (q, 2H), 4.02 (s, 3H), 4.62 (d, 1H), 5.76 (d, 1H), 8.18 (s, 1H).

Intermediate 60

4-(Azetidin-1-yl)-2-chloro-6-((2,2,2-trifluoroethoxy)methyl)pyrimidine

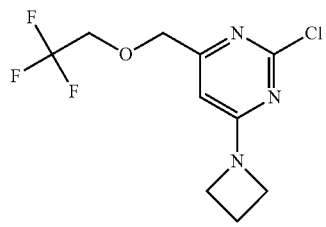 [SMILES: FC(F)(F)COCc1cc(N2CCC2)nc(Cl)n1]

A solution of azetidine (0.224 g, 2.39 mmol) and sodium methoxide (0.326 mL, 1.75 mmol) in MeOH (2 mL) was added to an ice-cold solution of 2,4-dichloro-6-((2,2,2-trifluoroethoxy)-methyl)pyrimidine (0.208 g, 0.80 mmol) in acetonitrile (2 mL). The mixture was stirred at 0° C. for 15 minutes. Water was added. The mixture was purified by preparative HPLC to give the title compound, 0.091 g (41%).

MS (ES$^+$) m/z 282 (M+H)$^+$.

Intermediate 61

2-Chloro-4-(1-ethoxyvinyl)-6-(methoxymethyl)pyrimidine

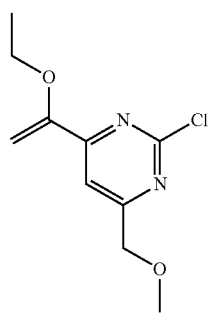

Methanol (1.06 g, 33.1 mmol) and sodium hydroxide (5 M (aq), 2.0 mL, 9.94 mmol) were added to a solution of (2-chloro-6-(1-ethoxyvinyl)pyrimidin-4-yl)methyl methanesulfonate (1.94 g, 6.63 mmol) in benzene (25 mL). Tetrabutylammonium hydrogen sulfate (0.225 g, 0.66 mmol) was added. The mixture was stirred vigorously at rt for 6 h. The phases were separated and the organic phase was filtered through a short silica plug which was washed with 10% MeOH in EtOAc (75 mL) and the solvent was evaporated. The residue was purified by preparative HPLC to give the title compound 0.287 g (19%).

MS (ES$^+$) m/z 228 (M+H)$^+$. $^1$H NMR (500 MHz, CDCl$_3$) δ 1.45 (t, 3H), 3.52 (s, 3H), 3.98 (q, 2H), 4.54 (s, 2H), 4.58 (d, 1H), 5.72 (d, 1H), 7.70 (s, 1H).

Intermediate 62

4-(1-Ethoxyvinyl)-N-(3-methoxy-4-(4-methyl-1H-imidazol-1-yl)phenyl)-6-(methoxymethyl)-pyrimidin-2-amine

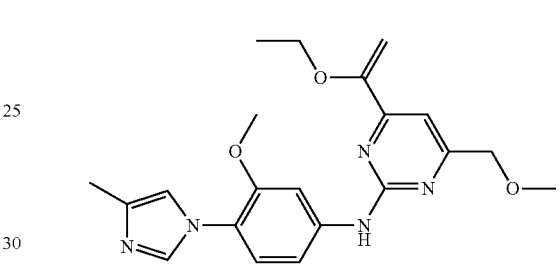

2-Chloro-4-(1-ethoxyvinyl)-6-(methoxymethyl)pyrimidine (167 mg, 0.73 mmol), 3-methoxy-4-(4-methyl-1H-imidazol-1-yl)aniline (178 mg, 0.88 mmol), cesium carbonate (476 mg, 1.46 mmol), palladium acetate (25 mg, 0.11 mmol) and 2-(dicyclohexylphosphino)biphenyl (38 mg, 0.11 mmol) in dioxane (4 mL) was heated under argon at 120° C. for 90 minutes in a microwave reactor. The mixture was filtered through a short silica plug which was washed with 10% MeOH in EtOAc (75 mL). The solvent was evaporated and the residue was purified by preparative HPLC to give the title compound 150 mg (52%).

MS (ES$^+$) m/z 396 (M+H)$^+$. $^1$H NMR (500 MHz, CHLOROFORM-d) δ ppm 1.46 (t, 3H) 2.31 (s, 3H) 3.52 (s, 3H) 3.89 (s, 3H) 3.98 (q, 2H) 4.47 (s, 2H) 4.50 (d, 1H) 5.59 (d, 1H) 6.87 (s, 1H) 7.05 (dd, 1H) 7.17 (d, 1H) 7.26 (s, 1H) 7.71-7.74 (m, 1H) 7.89-7.93 (m, 2H).

Intermediate 63

1-(2-(3-Methoxy-4-(4-methyl-1H-imidazol-1-yl)phenylamino)-6-(methoxymethyl)pyrimidin-4-yl)ethanone

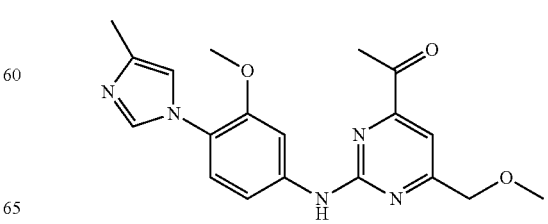

To a solution of 4-(1-ethoxyvinyl)-N-(3-methoxy-4-(4-methyl-1H-imidazol-1-yl)phenyl)-6-(methoxymethyl)pyrimidin-2-amine (172 mg, 0.43 mmol) in 1,4-dioxane (30 mL) were added water (2 mL) and hydrochloric acid (conc., 0.11 mL, 1.30 mmol). The mixture was stirred at 50° C. for 20 min. The solvents were evaporated. Sodium bicarbonate (aq, 50% saturated) was added and the mixture was extracted with DCM. The organic phase was separated on phase separator and the solvents were evaporated to give the title compound, 160 mg (100%).

MS (ES$^+$) m/z 368 (M+H)$^+$.

Intermediate 64

2-Chloro-4-((cyclopropylmethoxy)methyl)-6-(1-ethoxyvinyl)pyrimidine

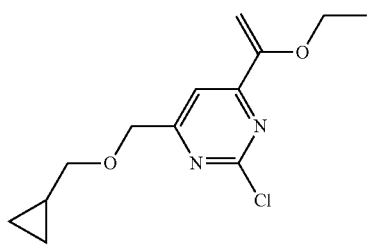 [SMILES: C=C(OCC)c1cc(COCC2CC2)nc(Cl)n1]

Cyclopropylmethanol (0.368 mL, 4.66 mmol) and sodium hydroxide (aq, 5M, 0.70 mL, 3.50 mmol) were added to a solution of (2-chloro-6-(1-ethoxyvinyl)pyrimidin-4-yl)methyl methanesulfonate (682 mg, 2.33 mmol) in benzene (8 mL). Tetrabutylammonium hydrogen sulfate was added (79 mg, 0.23 mmol). The mixture was stirred vigorously at rt over night. The organic phase was filtered through a short silica plug which was washed with 10% MeOH in EtOAc (75 mL) and the solvents were evaporated. The residue was purified by preparative HPLC to give the title compound 88 mg (14%).

MS (ES$^+$) m/z 269 (M+H)$^+$. $^1$H NMR δ 0.25-0.30 (m, 2H), 0.57-0.63 (m, 2H), 1.10-1.18 (m, 1H), 1.46 (t, 3H), 3.44 (d, 2H), 3.98 (q, 2H), 4.57 (d, 1H), 4.62-4.64 (m, 2H), 5.72 (d, 1H), 7.76 (s, 1H).

Intermediate 65

4-((Cyclopropylmethoxy)methyl)-6-(1-ethoxyvinyl)-N-(3-methoxy-4-(4-methyl-1H-imidazol-1-yl)phenyl)pyrimidin-2-amine

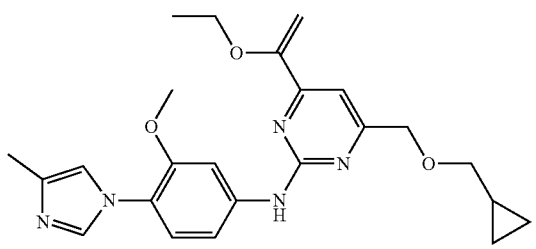 [SMILES: C=C(OCC)c1cc(COCC2CC2)nc(Nc2ccc(-n3cnc(C)c3)c(OC)c2)n1]

A mixture of 2-chloro-4-((cyclopropylmethoxy)methyl)-6-(1-ethoxyvinyl)pyrimidine (88 mg, 0.33 mmol), 3-methoxy-4-(4-methyl-1H-imidazol-1-yl)aniline (67 mg, 0.33 mmol), cesium carbonate (213 mg, 0.65 mmol), palladium acetate (11 mg, 0.05 mmol) and 2-(dicyclohexylphosphino)biphenyl (17 mg, 0.05 mmol) in dioxane (2 mL) were heated under argon atmosphere at 120° C. for 90 minutes in microwave reactor. The mixture was filtered through a short silica plug which was washed with 10% MeOH in EtOAc. The solvents were evaporated and the residue was purified by preparative to give the title compound 98 mg (69%).

MS (ES$^+$) m/z 436 (M+H)$^+$.

Intermediate 66

1-(6-(((Cyclopropylmethoxy)methyl)-2-(3-methoxy-4-(4-methyl-1H-imidazol-1-yl)-phenylamino)pyrimidin-4-yl)ethanone

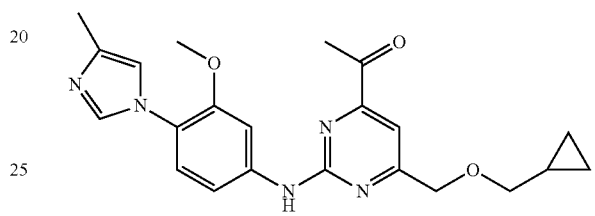

To a solution of 4-((cyclopropylmethoxy)methyl)-6-(1-ethoxyvinyl)-N-(3-methoxy-4-(4-methyl-1H-imidazol-1-yl)phenyl)pyrimidin-2-amine (98 mg, 0.23 mmol) in dioxane (15 mL) were added water (1 mL) and hydrochloric acid (conc., 0.056 mL, 0.68 mmol). The mixture was stirred at 50° C. for 20 min. The solvents were evaporated. Sodium bicarbonate (aq, 50% saturated) was added and the mixture was extracted with DCM. The organic phase was separated on phase separator and the solvents were evaporated to give the title compound 90 mg (98%).

MS (ES$^+$) m/z 408 (M+H)$^+$.

Intermediate 67

4-(1-Ethoxyvinyl)-N-(3-methoxy-4-(2-methyloxazol-5-yl)phenyl)-6-((2,2,2-trifluoroethoxy)methyl)pyrimidin-2-amine

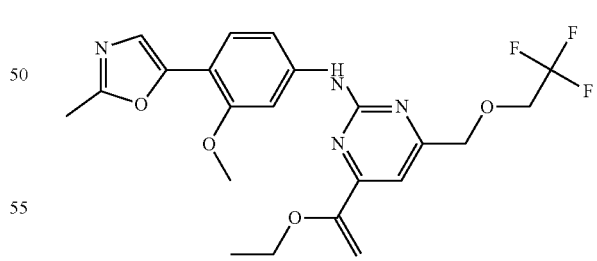

2-Chloro-4-(1-ethoxyvinyl)-6-((2,2,2-trifluoroethoxy)methyl)pyrimidine (0.10 g, 0.34 mmol) was dissolved in dioxane (5 mL). 3-Methoxy-4-(2-methyloxazol-5-yl)aniline (0.069 g, 0.34 mmol), cesium carbonate (0.220 g, 0.67 mmol), palladium(II) acetate (0.011 g, 0.05 mmol) and 2-(dicyclohexylphosphino)biphenyl (0.018 g, 0.05 mmol) were added. The vial was capped, evacuated and flushed with nitrogen. The mixture was heated by microwave irradiation at 120° C. for 1.5 h. The solvents were evaporated.

EtOAc was added and the mixture was filtered through a plug of silica. The solvents were evaporated and the residue was purified by column chromatography on silica eluting with EtAOc to give the title compound as a solid, 138 mg (88%).

MS (ES+) m/z 465 (M+H)+.

Intermediate 68

1-(2-(3-Methoxy-4-(2-methyloxazol-5-yl)phenylamino)-6-((2,2,2-trifluoroethoxy)methyl)-pyrimidin-4-yl)ethanone

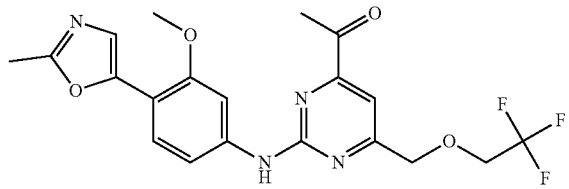 [SMILES: COc1cc(Nc2nc(COCC(F)(F)F)cc(C(C)=O)n2)ccc1-c1cnc(C)o1]

4-(1-Ethoxyvinyl)-N-(3-methoxy-4-(2-methyloxazol-5-yl)phenyl)-6-((2,2,2-trifluoroethoxy)-methyl)pyrimidin-2-amine (70 mg, 0.15 mmol) was dissolved in dioxane (10 mL). Water (0.5 mL) and hydrochloric acid (conc., 0.038 mL, 0.45 mmol) were added. The mixture was heated at 50° C. for 10 min. Sodium bicarbonate (s, 0.5 g) was added and mixture was stirred. Brine (2 mL) was added. The mixture was extracted with EtAOc (×2). The organic phase was dried (sodium sulfate) and evaporated to give the title compound as a dry film 64 mg (97%).

MS (API+) m/z 437 (M+H)+. 1H NMR (500 MHz, CHLOROFORM-d) δ ppm 2.53 (s, 3H) 2.72 (s, 3H) 4.01 (s, 3H) 4.02 (q, 2H) 4.73 (s, 2H) 7.14 (dd, 1H) 7.35 (s, 1H) 7.41 (bs, 1H) 7.47 (s, 1H) 7.69 (s, 1H) 7.70 (d, 1H).

Intermediate 69

1-(2-(3-Methoxy-4-(6-methylpyridazin-4-yl)phenylamino)-6-((2,2,2-trifluoroethoxy)-methyl)pyrimidin-4-yl)ethanone

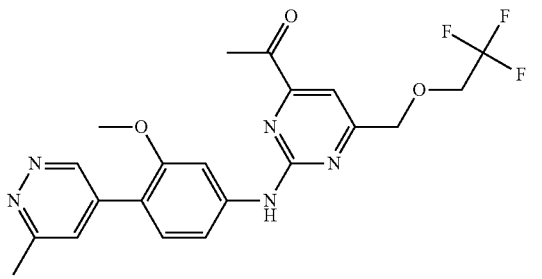 [SMILES: COc1cc(Nc2nc(COCC(F)(F)F)cc(C(C)=O)n2)ccc1-c1cnnc(C)c1]

4-(1-Ethoxyvinyl)-N-(3-methoxy-4-(6-methylpyridazin-4-yl)phenyl)-6-((2,2,2-trifluoroethoxy)-methyl)pyrimidin-2-amine (65 mg, 0.14 mmol) was dissolved in dioxane (10 mL). Water (0.5 mL) and hydrochloric acid (conc., 0.035 mL, 0.41 mmol) were added. The mixture was heated at 40° C. for 20 min. Sodium bicarbonate (s, 0.5 g) and brine (2 mL) were added and mixture was stirred for 10 min. The mixture was extracted with EtOAC (×2). The organic phase was dried (sodium sulfate) and evaporated to give the title compound as a solid 60 mg (98%).

MS (ES+) m/z 448 (M+H)+. 1H NMR (500 MHz, CHLOROFORM-d) δ ppm 2.73 (s, 3H) 2.77 (s, 3H) 3.94 (s, 3H) 4.03 (q, 2H) 4.75 (s, 2H) 7.23 (d, 1H) 7.39 (d, 1H) 7.48 (s, 1H) 7.52 (s, 1H) 7.53 (s, 1H) 7.75 (s, 1H) 9.29 (br. s, 1H).

Intermediate 70

(2Z)-1-(4-Bromo-2-methoxyphenyl)-2-(N-hydroxyimino)ethan-1-one

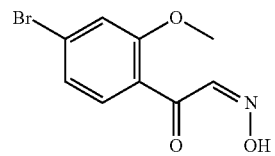

Sodium (138 mg, 6.0 mmol) was added to ethanol (12 mL) at room temperature. The mixture was stirred for 30 minutes. Isoamyl nitrite (0.81 mL, 6.0 mmol) and 1-(4-bromo-2-methoxy-phenyl)ethan-1-one (1.15 g, 5.0 mmol) were added. The mixture was stirred at room temperature for 3 days. Ethanol was removed under reduced pressure. The residue was dissolved in hydrochloric acid (1 M (aq), 12 mL) and then extracted with dichloromethane (×2). The organic phases were combined and dried over MgSO4, concentrated under reduced pressure to afford a mixture of starting material and (2Z)-1-(4-bromo-2-methoxyphenyl)-2-(N-hydroxyimino)ethan-1-one (1:1). The crude mixture was used directly for the next step.

(ESI) m/z 258 [M+H]+. 1H NMR (300 MHz, CHLOROFORM-d) δ ppm 3.88 (s, 3H), 7.11-7.17 (m, 2H), 7.47 (d, 1H), 8.10 (s, 1H).

Intermediate 71

3-(4-Bromo-2-methoxyphenyl)-3-hydroxy-5-methyl-2-(morpholin-4-yl)-3,4-dihydro-2H-pyrrol-1-ium-1-olate

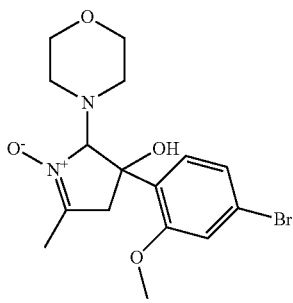 [SMILES: COc1cc(Br)ccc1C1(O)CC(C)=[N+]([O-])C1N1CCOCC1]

A mixture of (2Z)-1-(4-bromo-2-methoxyphenyl)-2-(N-hydroxyimino)ethan-1-one, morpholine (0.24 mL, 2.75 mmol) and acetone (10 mL) were stirred at room temperature for 3 days. The solvent was removed under reduced pressure and the residue was triturated in MTBE to the title compound as a solid (360 mg, 19% for two steps). (ESI) m/z 385 [M+H]+.

Intermediate 72

5-(4-Bromo-2-methoxyphenyl)-3-methylpyridazine

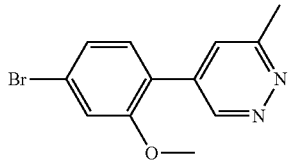

Hydrazine hydrate (4.8 mL, 99.0 mmol) was added to a solution of 3-(4-bromo-2-methoxyphenyl)-3-hydroxy-5-methyl-2-(morpholin-4-yl)-3,4-dihydro-2H-pyrrol-1-ium-1-olate (9.5 g, 24.7 mmol) in a mixture of water (115 mL) and AcOH (4.4 mL). The mixture was heated at 100° C. for 20 minutes and then cooled to room temperature. The precipitate was collected by filtration and dried under vacuum to afford the title compound as a solid, 3.5 g (51%).

(ESI) m/z 279 [M+H]$^+$. $^1$H NMR (300 MHz, DMSO-d$_6$) δ ppm 2.65 (s, 3H), 3.86 (s, 3H), 7.32 (dd, 1H), 7.41 (d, 1H), 7.45 (d, 1H), 7.68 (d, 1H), 9.21 (d, 1H).

Intermediate 73

3-Methoxy-4-(6-methylpyridazin-4-yl)aniline

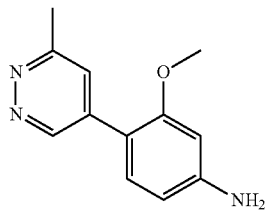 [SMILES: COc1cc(N)ccc1-c1cnnc(C)c1]

5-(4-Bromo-2-methoxyphenyl)-3-methylpyridazine (1.72 g, 6.20 mmol), Pd$_2$(dba)$_3$ (57 mg, 0.062 mmol), BINAP (116 mg, 0.19 mmol), sodium tert-butoxide (833 mg, 8.68 mmol), benzophenone imine (1.25 mL, 7.44 mmol) and toluene (30 mL) were added into a sealed tube. The flask was purged with N$_2$ three times. The reaction was stirred at 80° C. overnight and then cooled down, filtered through a pad of diatomaceous earth and the filter was washed with MTBE. The filtrate was concentrated. The residue was dissolved in MeOH (60 mL). NaOAc (1.22 g, 14.90 mmol) and ammonium hyxroxide hydrochloride (776 mg, 11.2 mmol) was added. The mixture was stirred at room temperature for 1 hour. Sodium carbonate (1.23 g, 11.60 mmol) was added, and the mixture was stirred at room temperature for 10 minutes and then concentrated under reduced pressure. The residue was taken up in dichloromethane. The organic phase was washed with water, brine, dried over sodium sulfate and the solvent was removed under reduced pressure. The residue was purified by flash chromatography on silica gel, eluting with 0% to 1% methanol in ethyl acetate to afford the title compound 1.24 g (93%) as a solid.

MS (ES$^+$) m/z 216 [M+H]$^+$. $^1$H NMR (300 MHz, CHLOROFORM-d) δ ppm 2.71 (s, 3H), 3.82 (s, 3H), 3.95 (br s, 2H), 6.31 (d, 1H), 6.38 (dd, 1H), 7.20 (d, 1H), 7.45 (d, 1H), 9.23 (d, 1H).

Intermediate 74

Ethyl 4-(cyclopropylmethoxy)-3-oxobutanoate

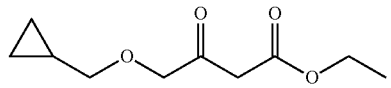

Cyclopropanemethanol (7.1 mL, 88 mmol, 1.0 eq) was added to a cold (0° C.) suspension of NaH (60% in oil, 7.2 g, 180 mmol) in MTBE (176 mL). The mixture was stirred at rt until the reached 25° C. and cooled back to 0° C. Ethyl 4-chloroacetoacetate (12 mL, 88.1 mmol) was added and the mixture was stirred at rt for 16 h. Hydrochloric acid (aq, 1M) was added. The layers were separated and the aqueous layer was extracted MTBE (×2). The combined organic layers were dried (sodium sulfate) and concentrated in vacuo. The residue was purified by column chromatography on silica eluting with a gradient of EtOAc in heptanes to afford the title compound as a liquid 15.7 g (89%).

$^1$H NMR (300 MHz, CHLOROFORM-d) δ ppm 0.23 (dd, 2H), 0.57 (dd, 2H), 1.00-1.10 (m, 1H), 1.28 (t, 3H), 3.35 (d, 2H), 3.53 (s, 2H), 3.95 (s, 2H), 4.20 (q, 2H).

Intermediate 75

6-[(Cyclopropylmethoxy)methyl]-2-sulfanylidene-1,2,3,4-tetrahydropyrimidin-4-one

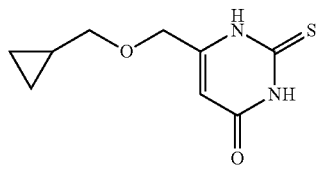 [SMILES: O=c1cc(COCC2CC2)[nH]c(=S)[nH]1]

Sodium (4.0 g, 172 mmol) was added to EtOH (80 mL) and stirred until all dissolved at 60° C. The solution was cooled down to rt and a solution of ethyl 4-(cyclopropylmethoxy)-3-oxobutanoate (15.7 g, 78.4 mmol) in EtOH (80 mL) was added, followed by thiourea (7.2 g, 94 mmol). The mixture was stirred under reflux conditions for 24 h. Hydrochloric acid (aq, 1 M) was added until pH~4 and the mixture was concentrated in vacuo. The residue was purified by column chromatography on silica eluting with a gradient of EtOAc and DCM to give the title compound as a solid, 15.7 g (95%).

$^1$H NMR (300 MHz, DMSO-d$_6$) δ ppm 0.18 (dd, 2H), 0.48 (dd, 2H), 0.95-1.08 (m, 1H), 3.30 (d, 2H), 4.20 (s, 2H). 5.76 (s, 1H), 12.2 (br s, 2H).

Intermediate 76

6-[(Cyclopropylmethoxy)methyl]-1,2,3,4-tetrahydro-pyrimidine-2,4-dione

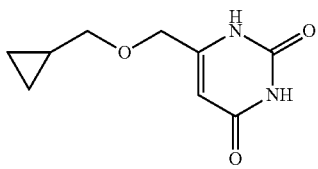 [SMILES: O=c1cc(COCC2CC2)[nH]c(=O)[nH]1]

6-[(Cyclopropylmethoxy)methyl]-2-sulfanylidene-1,2,3,4-tetrahydropyrimidin-4-one (10.3 g, 48.5 mmol) was added to bromoacetic acid (21.5 g, 155 mmol, 3.2 eq) in EtOH (108 mL) and $H_2O$ (441 mL). The reaction mixture was refluxed for 16 h then cooled down to rt and basified to pH~10 with sodium hydroxide (3 M, aq). The mixture was concentrated in vacuo and hydrochloric acid (aq, 10%) was added. The mixture was cooled to 0° C. The precipitate was isolated by filtration and dried to give the title compound as a solid (3.5 g, 37%).

$^1$H NMR (300 MHz, DMSO-$d_6$) δ ppm 0.19 (dd, 2H), 0.48 (dd, 2H), 0.95-1.08 (m, 1H), 3.29 (d, 2H), 4.15 (s, 2H), 5.44 (s, 1H), 10.85 (s, 1H), 10.97 (s, 1H).

Intermediate 77

2,4-Dichloro-6-[(cyclopropylmethoxy)methyl]pyrimidine

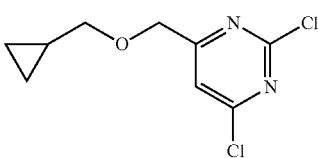 [SMILES: Clc1cc(COCC2CC2)nc(Cl)n1]

6-[(Cyclopropylmethoxy)methyl]-1,2,3,4-tetrahydropyrimidine-2,4-dione (2.6 g, 13.3 mmol) was added to a solution of phosphorus oxychloride (18 mL) and dimethylaniline (2.8 mL, 22.6 mmol). The mixture was heated at 120° C. for 10 min. The reaction mixture was poured into ice/DCM slurry and stirred for 16 h. The layers were separated and the aqueous layer was extracted twice with dichloromethane. The combined organic layers were dried (sodium sulfate) and concentrated in vacuo. The residue was purified by column chromatography on silica eluting with a gradient of EtOAc in heptanes to afford the title compound as an oil 2.29 g (74%).

(ES$^+$) m/z 233 [M+H]$^+$. $^1$H NMR (300 MHz, CHLOROFORM-d) δ ppm 0.26 (dd, 2H), 0.60 (dd, 2H), 1.04-1.17 (m, 1H), 3.43 (d, 2H), 4.60 (s, 2H), 7.54 (s, 1H).

Intermediate 78

Ethyl 2-{2-chloro-6-[(2,2,2-trifluoroethoxy)methyl]pyrimidin-4-yl}acetate

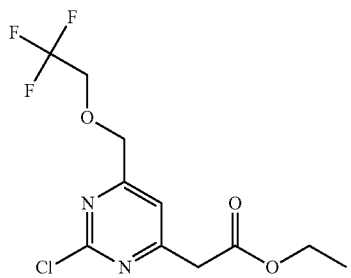 [SMILES: CCOC(=O)Cc1cc(COCC(F)(F)F)nc(Cl)n1]

To a cold (0° C.) suspension of NaH (400 mg, 9.96 mmol, 60% in oil) in THF (8 mL) was slowly added ethylacetoacetate (1.45 mL, 11.5 mmol). The solution was allowed to stir at rt for 10 min then concentrated in vacuo. The residue was rapidly put under $N_2$. A solution of 2,4-dichloro-6-[(2,2,2-trifluoroethoxy)methyl]pyrimidine (2.0 g, 7.66 mmol) in toluene (38 mL) was added to the residue. The reaction mixture was stirred under reflux for 16 h. Ammonium chloride (aq, 1 mL) was added and stirred vigorously for 10 min. Silica was added and the mixture was concentrated. The residue was purified on a silica gel cartridge eluting with 0% to 40% EtOAc/heptanes to give ethyl the title compound, 600 mg (28%).

$^1$H NMR (300 MHz, CHLOROFORM-d) δ ppm 1.28 (t, 3H), 3.84 (s, 2H), 4.00 (q, 2H), 4.21 (q, 2H), 4.76 (s, 2H), 7.48 (s, 1H).

Intermediate 79

Ethyl 2-(2-{[3-methoxy-4-(4-methyl-1H-imidazol-1-yl)phenyl]amino}-6-[(2,2,2-trifluoroethoxy)methyl]pyrimidin-4-yl)acetate

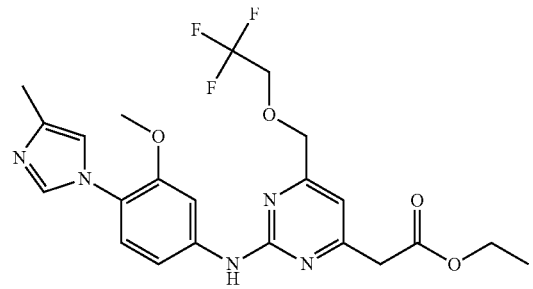 [SMILES: CCOC(=O)Cc1cc(COCC(F)(F)F)nc(Nc2ccc(-n3cnc(C)c3)c(OC)c2)n1]

Palladium acetate (21 mg, 0.095 mmol) was added to a degassed solution of 3-methoxy-4-(4-methyl-1H-imidazol-1-yl)aniline (155 mg, 0.76 mmol), ethyl 2-{2-chloro-6-[(2,2,2-trifluoro-ethoxy)methyl]pyrimidin-4-yl}acetate (180 mg, 0.63 mmol), $Cs_2CO_3$ (411 mg, 1.26 mmol), (2-biphenyl)dicyclohexylphosphine (33 mg, 0.95 mmol) in 1,4-dioxane (4 mL). The microwave tube was capped and the heterogeneous solution was immersed in a sonic bath for 2 min prior to heating it in a microwave reactor at 120° C. for 1.5 h. The reaction was cooled down to rt and concentrated in vacuo with diatomaceous earth. The resulting mixture was purified on silica gel eluting with 0% to 5% MeOH/DCM (1% ammonium hydroxide). The residue obtained was purified on a C18 reverse phase cartridge eluting with 0% to 40% MeOH/H$_2$O (containing 0.05% TFA) to give the title compound as a gum, 110 mg (38%).

$^1$H NMR (300 MHz, CHLOROFORM-d) δ ppm 1.28 (t, 3H), 2.30 (s, 3H), 3.72 (s, 2H), 3.86 (s, 3H), 3.99 (q, 2H), 4.21 (q, 2H), 4.66 (s, 2H), 6.87 (s, 1H), 6.93 (s, 1H), 7.04 (dd, 1H), 7.16 (d, J=8.5 Hz, 1H), 7.29 (s, 1H), 7.63 (s, 1H), 7.73 (d, 1H).

Intermediate 80

2-(2-{[3-Methoxy-4-(4-methyl-1H-imidazol-1-yl)phenyl]amino}-6-[(2,2,2-trifluoroethoxy)-methyl]pyrimidin-4-yl)acetamide

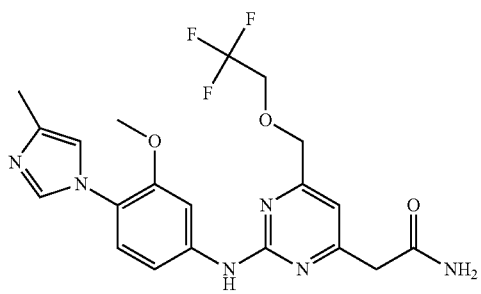 [SMILES: COc1cc(Nc2nc(COCC(F)(F)F)cc(CC(N)=O)n2)ccc1-n1cnc(C)c1]

Ethyl 2-(2-{[3-methoxy-4-(4-methyl-1H-imidazol-1-yl)phenyl]amino}-6-[(2,2,2-trifluoro-ethoxy)methyl]pyrimidin-4-yl)acetate (140 mg, 0.30 mmol, 1.0 eq) was suspended in ammonium hydroxide (3 mL) with few crystals of potassium cyanide in a sealed tube. The mixture was stirred 4 days at 65° C. The reaction mixture was cooled down to rt, water was added and the aqueous layer was extracted with DCM (5×). The combined organic layers were dried over sodium sulfate and concentrated. The residue was purified on a silica gel cartridge eluting with 0% to 10% MeOH/DCM (1% ammonium hydroxide) to give the title compound as a solid, 68 mg (50%).

$^1$H NMR (300 MHz, CHLOROFORM-d) δ ppm 2.09 (s, 2H), 2.29 (s, 3H), 3.65 (s, 2H), 3.84 (s, 3H), 3.98 (q, 2H), 4.65 (s, 2H), 5.99 (br s, 1H), 6.70 (br s, 1H), 6.86 (s, 1H), 6.92 (s, 1H), 7.11-7.17 (m, 2H), 7.64 (s, 1H), 7.71 (s, 1H), 7.95 (s, 1H).

Intermediate 81

2,4-dichloro-6-(1-ethoxyvinyl)-5-methylpyrimidine

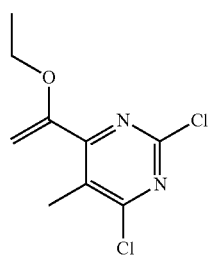

2,4,6-Trichloro-5-methylpyrimidine (2.0 g, 10.13 mmol) and bis(triphenylphosphine)palladium chloride (0.142 g, 0.20 mmol) in DMF (40 mL) was degased. Tributyl(1-ethoxyvinyl)stannane (3.59 mL, 10.64 mmol) was added. The mixture was heated at 100° C. for 1.5 h under nitrogen atmosphere. The mixture was poured into a solution of KF (6 g) in water (100 mL). MTBE (100 mL) was added mixture was for stirred 10 min. The solid was removed by filtration and was washed with MTBE (60 mL). The organic phase was washed with water, dried over sodium sulfate and evaporated. The mixture was purified by column chromatography eluting with DCM to give the title compound as a solid, 1.15 g (49%).

MS (APCI$^+$) m/z 333 (M+H)$^+$. $^1$H NMR (400 MHz, CHLOROFORM-d): δ ppm 1.40 (t, 3H), 2.41 (s, 3H), 3.94 (q, 2H), 4.58 (d, 1H), 4.79 (d, 1H).

Intermediate 82

Ethyl 3-oxo-4-(2,2,2-trifluoroethoxy)pentanoate

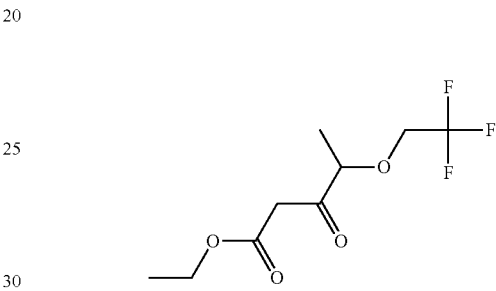

Di(1H-imidazol-1-yl)methanone (3.58 g, 22.05 mmol) was added portion wise to a stirred solution of 2-(2,2,2-trifluoroethoxy)propanoic acid (3.3 g, 19.17 mmol) in acetonitrile (12 mL). The mixture was stirred at rt for 1 h to give solution 1. Potassium 3-ethoxy-3-oxopropanoate (2.53 g, 19.17 mmol) was stirred in acetonitrile (12 mL) for 5 min. Triethylamine (8.02 mL, 57.52 mmol) and magnesium chloride (4.38 g, 46.02 mmol) were added and the mixture was stirred at rt for 2 h. Solution 1 was added and the mixture was stirred for 3 h. Hydrochloric acid (13%, aq, 70 mL) was added and the mixture was stirred for 10 min. The phases was separated and water phase was extracted three times with EtOAc. The organic phase was washed with brine containing sodium bicarbonate, dried over magnesium sulfate, filtrated through a pad of silica and the solvents were evaporated to give a liquid, 4.29 g (92%).

MS (APCI$^+$) m/z 243 (M+H)$^+$.

Intermediate 83

2-Chloro-4-(cyclopropylmethoxy)-6-[(2,2,2-trifluoroethoxy)methyl]pyrimidine

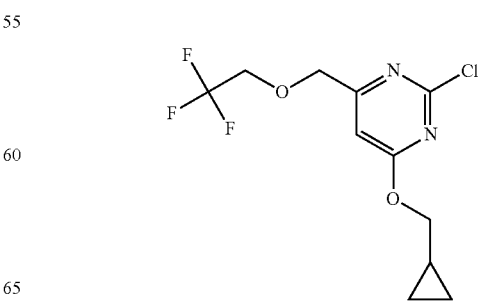

67

Sodium hydride (19.0 mg, 0.46 mmol) was added to a solution of cyclopropylmethanol (0.037 mL, 0.46 mmol) in dry THF (1 mL) at room temperature. The mixture was stirred for 5 minutes and then a solution of 2,4-dichloro-6-[(2,2,2-trifluoroethoxy)methyl]pyrimidine (120 mg, 0.46 mmol) in dry THF (1 mL) was added. The reaction was stirred at room temperature for 2.5 hours. Water was added and the mixture was extracted with ethylacetate. The organic phase was washed with water, brine, dried over magnesium sulfate and the solvent was removed under reduced pressure. The residue was purified by flash chromatography on silica gel, eluting with mixtures of 0% to 10% ethyl acetate in heptanes to afford the title compound as a solid, 40 mg, (29%) as yellow solid.

MS (ESI$^+$) m/z 297 [M+H]$^+$. $^1$H NMR (300 MHz, CDCl$_3$) δ ppm 0.34-0.37 (m, 2H), 0.64-0.70 (m, 2H), 0.80-0.90 (m, 1H), 3.97 (q, 2H), 4.22 (d, 2H), 4.66 (s, 2H), 6.83 (s, 1H).

Intermediate 84

2-(2-Chloro-6-(1-ethoxy-2,2-difluorocyclopropyl)pyrimidin-4-yl)propan-2-ol

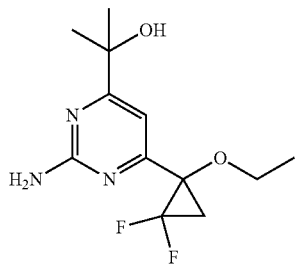 [SMILES: CCOC1(c2cc(C(C)(C)O)nc(N)n2)CC1(F)F]

2-(2-Chloro-6-(1-ethoxyvinyl)pyrimidin-4-yl)propan-2-ol (130 mg, 0.54 mmol) was co-evaporated with dry acetonitrile and was then dissolved in acetonitrile (3 mL) and copper(I) iodide (20 mg, 0.11 mmol) was added. The vessel was evacuated and filled with argon. The mixture was heated to 45° C. and 2,2-difluoro-2-(fluorosulfonyl)acetic acid (0.072 mL, 0.70 mmol) was added in 3 portions every 10 minute. The reaction was stirred at 45° C. for 50 minutes after last addition. More 2-(fluorosulfonyl)difluoroacetic acid (0.022 mL, 0.21 mmol) was added and the mixture was stirred at 45° C. for 20 min. More 2-(fluorosulfonyl)difluoroacetic acid (0.011 mL, 0.11 mmol) was added and the mixture was stirred at 45° C. for 20 minutes. The solvent was evaporated and the residue was dissolved in EtOAc. The organic phase was washed twice with brine, dried over magnesium sulfate, and the solvents were evaporated. The residue was purified by preparative HPLC to give the title compound as a dry film 11 mg (7%).

MS (ESI$^+$) m/z 293 [M+H]$^+$. $^1$H NMR (500 MHz, CDCl$_3$) δ ppm 1.30 (t, 3H) 1.59 (d, 6H) 1.84-1.92 (m, 1H) 2.71-2.82 (m, 1H) 3.33 (s, 1H) 3.48-3.60 (m, 2H) 7.78 (s, 1H).

68

Example 1

4-(Azetidin-1-yl)-6-((cyclopropylmethoxy)methyl)-N-(3-methoxy-4-(4-methyl-1H-imidazol-1-yl)phenyl)pyrimidin-2-amine

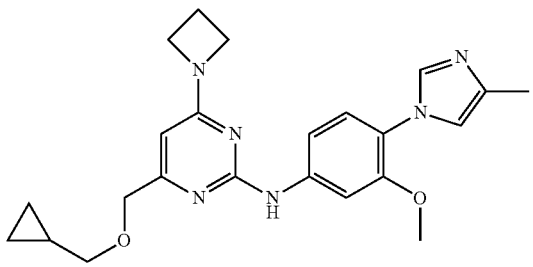 [SMILES: COc1cc(Nc2nc(COCC3CC3)cc(N3CCC3)n2)ccc1-n1cnc(C)c1]

A mixture of 4-(azetidin-1-yl)-2-chloro-6-((cyclopropylmethoxy)methyl)pyrimidine (44 mg, 0.17 mmol), 3-methoxy-4-(4-methyl-1H-imidazol-1-yl)aniline (42 mg, 0.21 mmol), cesium carbonate (113 mg, 0.35 mmol), palladium acetate (5.84 mg, 0.03 mmol) and 2-(dicyclohexylphosphino)biphenyl (9 mg, 0.03 mmol) in dioxane (2 mL) was stirred under argon at 120° C. for 90 minutes in microwave reactor. The mixture was filtered through a short silica plug which was washed with 10% MeOH in EtOAc (75 mL). The solvent was removed in vacuum and the residue was purified by preparative HPLC to give the title compound as a solid 56 mg (77%).

MS (APCI$^+$) m/z 421 (M+H)$^+$. $^1$H NMR (500 MHz, CDCl$_3$) δ 0.22-0.26 (m, 2H), 0.54-0.60 (m, 2H), 1.08-1.17 (m, 1H), 2.29 (s, 3H), 2.43 (quin, 2H), 3.40 (d, 2H), 3.84 (s, 3H), 4.13 (t, 4H), 4.38 (s, 2H), 5.92 (s, 1H), 6.85 (s, 1H), 6.88 (dd, 1H), 7.09 (d, 1H), 7.23 (s, 1H), 7.60 (s, 1H), 7.95 (d, 1H).

Example 2

N$^4$-Methyl-N$^2$-(4-(4-methyl-1H-imidazol-1-yl)phenyl)-6-((2,2,2-trifluoroethoxy)methyl)-pyrimidine-2,4-diamine

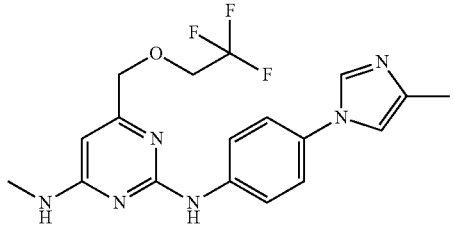

A mixture of 2-chloro-N-methyl-6-((2,2,2-trifluoroethoxy)methyl)pyrimidin-4-amine (85 mg, 0.33 mmol), 4-(4-methyl-1H-imidazol-1-yl)aniline (100 mg, 0.58 mmol), cesium carbonate (217 mg, 0.67 mmol), palladium(II) acetate (11 mg, 0.05 mmol) and 2-(dicyclohexylphosphino)biphenyl (17 mg, 0.05 mmol) in dioxane (3 mL) was heated in a microwave reactor under notrogen atmosphere at 120° C. for 90 min. The reaction mixture was filtered through a pad of diatomeous earth which was eluted with MeOH. The mixture was partitioned between EtOAc and sodium hydroxide (aq, 1 M). The organic phase was separated, dried over sodium sulfate and concentrated in vacuum. The residue was purified by preparative HPLC to give the title compound as a solid 52 mg, (40%).

MS (ES⁺) m/z 393 (M+H)⁺. ¹H NMR (500 MHz, DMSO-d₆) ▫ ppm 2.15 (s, 3H) 2.86 (br. s, 3H) 4.20 (q, 2H) 4.45 (s, 2H) 6.01 (br. s, 1H) 7.29 (br. s, 1H) 7.32 (s, 1H) 7.42 (d, 2H) 7.91 (d, 2H) 7.98 (s, 1H) 9.21 (s, 1H).

Example 3

2-[2-[3-Methoxy-4-(4-methylimidazol-1-yl)anilino]-6-(2,2,2-trifluoroethoxymethyl)pyrimidin-4-yl]acetonitrile

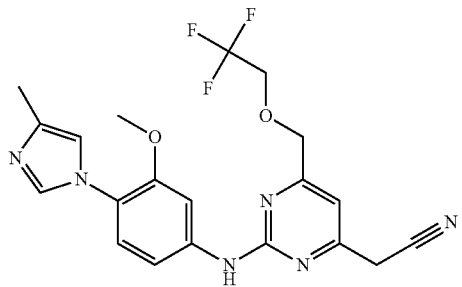 [SMILES: COc1cc(Nc2nc(CC#N)cc(COCC(F)(F)F)n2)ccc1-n1cnc(C)c1]

2-(2-{[3-Methoxy-4-(4-methyl-1H-imidazol-1-yl)phenyl]amino}-6-[(2,2,2-trifluoroethoxy)-methyl]pyrimidin-4-yl)acetamide (68 mg, 0.15 mmol, 1.0 eq) was added to a solution of Phosphorus oxychloride (4 mL) and dimethylaniline (0.033 mL, 0.26 mmol, 1.75 eq). The reaction mixture was immersed in a pre-heated oil bath at 120° C. for 10 min. The reaction mixture, still hot, was rapidly poured into ice/DCM slurry and stirred for 16 h. The layers were separated and the aqueous layer was extracted twice with dichloromethane. The combined organic layers were dried over sodium sulfate and concentrated. The residue was purified on a silica gel cartridge eluting with a gradient of methanol, DCM and EtOAc. The residue was further purified on a C18 reverse phase cartridge eluting with 30% to 70% MeOH/H₂O containing 0.05% TFA to give the title compound, 8 mg (12%).

MS (ES⁺) m/z 433 (M+H)⁺. ¹H NMR (300 MHz, CD₃OD): ppm 2.42 (s, 3H), 3.96 (s, 3H), 4.11 (s, 2H), 4.14 (q, 2H), 4.71 (s, 2H), 7.02 (s, 2H), 7.35-7.43 (m, 2H), 7.51 (s, 1H), 8.16 (s, 1H), 9.05 (s, 1H).

Example 4

N²-(3-Methoxy-4-(4-methyl-1H-imidazol-1-yl)phenyl)-N⁴,5-dimethyl-6-((2,2,2-trifluoroethoxy)methyl)pyrimidine-2,4-diamine

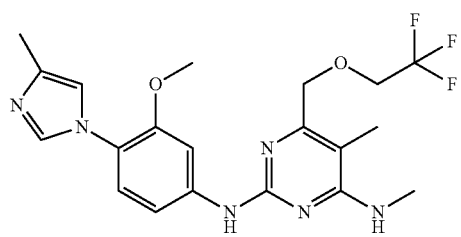 [SMILES: CNc1nc(Nc2ccc(-n3cnc(C)c3)c(OC)c2)nc(COCC(F)(F)F)c1C]

A mixture of N-(3-methoxy-4-(4-methyl-1H-imidazol-1-yl)phenyl)-5-methyl-4-(2,2,2-trifluoroethoxy)-6-((2,2,2-trifluoroethoxy)methyl)pyrimidin-2-amine (0.135 g, 0.27 mmol) and methyl amine (1.35 mL, 10.7 mmol) in butanol (5 mL) was heated in MW at 160-180° C. for 3 h. The volatiles were removed in vacuum, the residue was extracted from water (5 mL) with dichloromethane (2×10 mL). The organic phase was dried over sodium sulfate and concentrated in vacuum. The residue was purified by preparative HPLC to yield the title compound as a solid, 69 mg (59%).

MS (APCI⁺) m/z 437 (M+H)⁺. ¹H NMR (500 MHz, CHLOROFORM-d): ▫ ppm 2.03 (s, 3H), 2.30 (s, 3H), 3.10 (d, 3H), 3.85 (s, 3H), 3.91 (q, 2H), 4.61 (s, 2H), 4.86 (q, 1H), 6.87 (s, 1H), 6.99 (dd, 1H), 7.08 (s, 1H), 7.13 (d, 1H), 7.62 (d, 1H), 7.89 (d, 1H).

Example 5

2-(2-(3-Methoxy-4-(4-methyl-1H-imidazol-1-yl)phenylamino)-5-methyl-6-((2,2,2-trifluoroethoxy)methyl)pyrimidin-4-yl)propan-2-ol

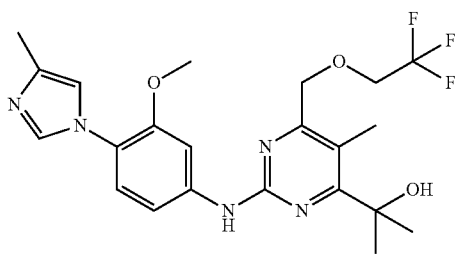 [SMILES: COc1cc(Nc2nc(COCC(F)(F)F)c(C)c(C(C)(C)O)n2)ccc1-n1cnc(C)c1]

Methylmagnesium bromide (0.199 mL of 3M solution, 0.28 mmol) was added slowly to a solution of 1-(2-(3-methoxy-4-(4-methyl-1H-imidazol-1-yl)phenylamino)-5-methyl-6-((2,2,2-trifluoroethoxy)methyl)pyrimidin-4-yl)ethanone (25 mg, 0.06 mmol) in THF (3 mL). The mixture was stirred at RT for 1 h. The mixture was quenched with saturated solution of ammonium chloride in water (1.5 mL) and diluted with brine (10 mL). The mixture was extracted with EtOAc (2×20 mL). The organic phase was dried over sodium sulfate and concentrated in vacuum. The residue was purified by preparative HPLC to give title compound as a dry film, 13 mg (45%).

MS (APCI⁺) m/z 466 (M+H)⁺. ¹H NMR (500 MHz, CHLOROFORM-d): ▫ ppm 1.63 (s, 6H), 2.30 (s, 3H), 2.37 (s, 3H), 3.87 (s, 3H), 3.98 (q, 2H), 4.76 (s, 2H), 5.50 (br. s, 1H), 6.88 (s, 1H), 7.06 (dd, 1H), 7.19 (d, 1H), 7.39 (s, 1H), 7.61 (d, 1H), 7.64 (s, 1H).

Example 6

1-(2-(3-Methoxy-4-(4-methyl-1H-imidazol-1-yl)phenylamino)-5-methyl-6-((2,2,2-trifluoroethoxy)methyl)pyrimidin-4-yl)ethanol

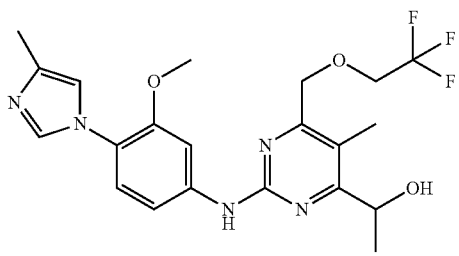 [SMILES: COc1cc(Nc2nc(COCC(F)(F)F)c(C)c(C(C)O)n2)ccc1-n1cnc(C)c1]

1-(2-(3-Methoxy-4-(4-methyl-1H-imidazol-1-yl)phenylamino)-5-methyl-6-((2,2,2-trifluoroethoxy)methyl)pyrimidin-4-yl)ethanone (25 mg, 0.06 mmol) in dioxane (3 mL) and water (3 mL) was treated with sodium borohydride (8 mg, 0.22 mmol). The mixture was stirred at rt for 30 min. Acetic acid (0.5 mL) was added and the mixture was stirred for 25 min. The mixture was concentrated and the residue was purified by preparative HPLC to give the title compound as a dry film, 13 mg (48%).

MS (APCI+) m/z 452 (M+H)+. $^1$H NMR (500 MHz, CHLOROFORM-d): ⍵ ppm 1.43 (d, 3H), 2.20 (s, 3H), 2.31 (s, 3H), 3.87 (s, 3H), 3.97 (q, 2H), 4.24 (d, 1H), 4.74 (s, 2H), 4.99 (m, 1H), 6.89 (s, 1H), 7.06 (dd, 1H), 7.19 (d, 1H), 7.32 (s, 1H), 7.65 (s, 1H), 7.67 (d, 1H).

Example 7

1-(2-(3-Methoxy-4-(4-methyl-1H-imidazol-1-yl)phenylamino)-6-(1-(2,2,2-trifluoroethoxy)-ethyl)pyrimidin-4-yl)ethanol

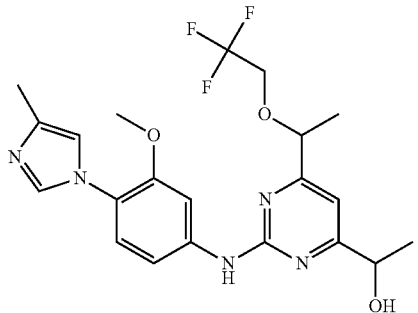 [SMILES: COc1cc(Nc2nc(C(C)O)cc(C(C)OCC(F)(F)F)n2)ccc1-n1cnc(C)c1]

1-(2-(3-Methoxy-4-(4-methyl-1H-imidazol-1-yl)phenylamino)-6-(1-(2,2,2-trifluoroethoxy)-ethyl)pyrimidin-4-yl)ethanone (90 mg, 0.20 mmol) was dissolved in ethanol (5 mL). Sodium borohydride (30.3 mg, 0.80 mmol) was added in portions. The mixture was stirred at rt for 10 min. Acetone (2 mL) was added and the mixture was stirred for 20 min. The mixture was filtered, the volatiles were removed in vacuum, and the residue was purified by preparative HPLC to yield the title compound consisting of four stereoisomers, 64 mg (71%).

MS (APCI+) m/z 452 (M+H)$^+$. $^1$H NMR (500 MHz, CHLOROFORM-d) ⍵ ppm 1.49-1.62 (m, 6H) 2.30 (s, 3H) 3.87 (s, 1H) 3.77-3.95 (m, 2H) 4.17 (br. s, 1H) 4.54 (m, 1H) 4.82 (q, 1H) 6.88 (s, 1H) 6.97 (d, 1H) 7.05 (dd, 1H) 7.18 (d, 1H) 7.45 (s, 1H) 7.64 (d, 1H) 7.77 (d, 1H).

1-(2-(3-Methoxy-4-(4-methyl-1H-imidazol-1-yl)phenylamino)-6-(1-(2,2,2-trifluoroethoxy)-ethyl)pyrimidin-4-yl)ethanol, isomer 4

The mixture described above (62 mg) was submitted to chiral separation by SFC that yielded four individual stereoisomers. Described below is enantiomerically pure isomer 4, which is the last eluted enantiomer from the chiral column. The solvents were evaporated to give the title compound as a dry film 7.7 mg (12%).

MS (APCI$^+$) m/z 452 (M+H)$^+$. $^1$H NMR (500 MHz, ACETONITRILE-d$_3$) ⍵ ppm 1.45 (d, 3H), 1.50 (d, 3H), 2.19 (s, 4H), 3.85 (s, 3H), 3.92-4.03 (m, 2H), 4.57 (q, 1H), 4.70 (q, 1H), 6.94 (s, 1H), 7.05 (s, 1H), 7.16-7.25 (m, 2H), 7.56 (d, 1H), 7.91 (d, 1H), 8.07 (s, 1H).

Analytical SFC: Column Chiralcel AD-H; 4.6*250 mm; 5 μm, Mobile phase: 20% EtOH+0.1% diethylamine; 80% CO$_2$, flow 3 mL/min, t$_R$=8.69 min.

Example 8

N$^4$-Isopropyl-N$^2$-(3-methoxy-4-(4-methyl-1H-imidazol-1-yl)phenyl)-6-((2,2,2-trifluoroethoxy)methyl)pyrimidine-2,4-diamine

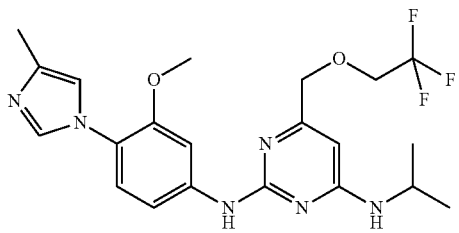 [SMILES: COc1cc(Nc2nc(COCC(F)(F)F)cc(NC(C)C)n2)ccc1-n1cnc(C)c1]

3-Methoxy-4-(4-methyl-1H-imidazol-1-yl)aniline (90 mg, 0.44 mmol), 2-chloro-N-isopropyl-6-((2,2,2-trifluoroethoxy)methyl)pyrimidin-4-amine (63 mg, 0.22 mmol), cesium carbonate (145 mg, 0.44 mmol), palladium acetate (7.48 mg, 0.03 mmol) and 2-(dicyclohexylphosphino)-biphenyl (11.68 mg, 0.03 mmol) in dioxane (1.5 mL) were mixed in a vial under N$_2$ atmosphere. The mixture was heated at 120° C. in a microwave reactor for 90 minutes. The mixture was filtered through diatomeous earth and the filter plug was washed with methanol. The solvents were evaporated and the residue was purified by preparative HPLC to give the title compound as a solid 60 mg (60%).

MS (APCI$^+$) m/z 451 (M+H)$^+$. $^1$H NMR (500 MHz, ACETONITRILE-d$_3$) ⍵ 1.21 ppm (d, 6H), 2.18-2.21 (m, 3H), 3.83 (s, 3H), 4.06 (q, 2H), 4.12-4.31 (m, 1H), 4.45 (s, 2H), 5.66 (d, 1H), 6.01 (s, 1H), 6.92 (s, 1H), 7.15 (d, 1H), 7.21 (d, 1H), 7.54 (d, 1H), 7.57 (s, 1H), 7.85 (br. s, 1H).

Example 9

N$^2$-(3-Methoxy-4-(4-methyl-1H-imidazol-1-yl)phenyl)-N4-methyl-6-((2,2,2-trifluoroethoxy)methyl)pyrimidine-2,4-diamine

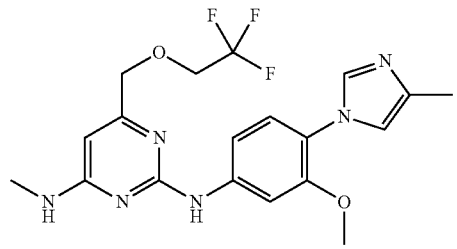

2-Chloro-N-methyl-6-((2,2,2-trifluoroethoxy)methyl)pyrimidin-4-amine (161 mg, 0.63 mmol), 3-methoxy-4-(4-methyl-1H-imidazol-1-yl)aniline (256 mg, 1.26 mmol), cesium carbonate (410 mg, 1.26 mmol), palladium(II) acetate (21 mg, 0.09 mmol) and 2-(dicyclohexylphosphino)biphenyl (33 mg, 0.09 mmol) were mixed in dioxane (10 mL) under an atmosphere of nitrogen. The vial was heated in microwave reactor at 120° C. for 90 min. The mixture was filtered through a plug of diatomeous earth which was eluted with MeOH. The mixture was partitioned between EtOAc and sodium hydroxide (1 M, aq). The organic layer was dried over sodium sulfate and concentrated in vacuum. The residue was purified by preparative HPLC to give the title compound as a solid 136 mg (51%).

MS (ES$^+$) m/z 423 (M+H)$^+$. $^1$H NMR (500 MHz, DMSO-d$_6$) ◊ ppm 2.13 (s, 3H) 2.88 (br. s, 3H) 3.78 (s, 3H) 4.20 (q, 2H) 4.46 (s, 2H) 6.03 (br. s, 1H) 7.01 (s, 1H) 7.15 (d, 1H) 7.26 (d, 1H) 7.34 (br. s, 1H) 7.63 (s, 1H) 8.08 (br. s, 1H) 9.26 (s, 1H).

Example 10

(2-(3-Methoxy-4-(4-methyl-1H-imidazol-1-yl)phenylamino)-6-((2,2,2-trifluoroethoxy)methyl)pyrimidin-4-yl)methanol

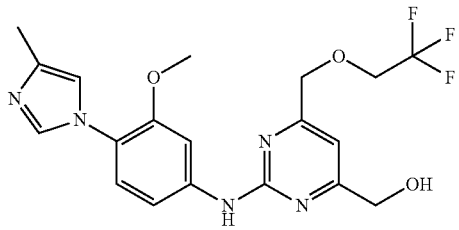 [SMILES: COc1cc(Nc2nc(CO)cc(COCC(F)(F)F)n2)ccc1-n1cnc(C)c1]

A solution of ethyl 2-(3-methoxy-4-(4-methyl-1H-imidazol-1-yl)phenylamino)-6-((2,2,2-trifluoroethoxy)methyl)pyrimidine-4-carboxylate (0.38 g, 0.82 mmol) in ethanol (20 mL), was heated to 45°. Citric acid (1.255 g, 6.53 mmol) and sodium borohydride (0.309 g, 8.16 mmol) were added in portions (of 5-10 mg each) keeping pH within a range of 5-7 over 3 h. Acetone (2 mL) was added and reaction mixture was stirred for 15 min. Chloroform (40 mL) was added. The mixture was filtered and concentrated. The residue was purified by column chromatography on silica column eluting with a gradient of MeOH and DCM to give the title compound as a solid, 0.24 g (69%).

MS (APCI$^+$) m/z 424 (M+H)$^+$. $^1$H NMR (500 MHz, CHLOROFORM-d) ◊ ppm 2.29 (s, 3H) 3.85 (s, 3H) 3.99 (q, 2H) 4.68 (s, 2H) 4.72 (s, 2H) 6.88 (s, 1H) 6.99 (s, 1H) 7.09 (dd, 1H) 7.17 (d, 1H) 7.41 (s, 1H) 7.63 (s, 1H) 7.67 (d, 1H).

Example 11

2-(2-(3-Methoxy-4-(4-methyl-1H-imidazol-1-yl)phenylamino)-6-(1-(2,2,2-trifluoroethoxy)ethyl)pyrimidin-4-yl)propan-2-ol

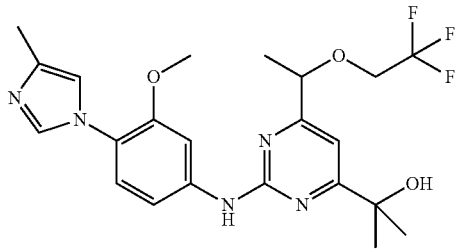 [SMILES: COc1cc(Nc2nc(C(C)OCC(F)(F)F)cc(C(C)(C)O)n2)ccc1-n1cnc(C)c1]

1-(2-(3-Methoxy-4-(4-methyl-1H-imidazol-1-yl)phenylamino)-6-(1-(2,2,2-trifluoroethoxy)-ethyl)pyrimidin-4-yl)ethanone (120 mg, 0.27 mmol) was coevaporated with dioxane and dissolved in THF (5 mL). The mixture was added slowly to a vigorously stirred solution of methylmagnesium bromide (0.712 mL of 3M solution, 2.14 mmol). The mixture was stirred for 10 minutes. The mixture was cooled in an ice bath and slowly quenched with a saturated solution of ammonium chloride in water (10 mL). The mixture was extracted with ethyl acetate (2×20 mL). The organic phase was separated, dried over sodium sulfate and concentrated. The residue was purified by preparative HPLC to give the title compound as a solid 81 mg (64%).

MS (APCI$^+$) m/z 466 (M+H)$^+$. $^1$H NMR (500 MHz, CHLOROFORM-d) ◊ ppm 1.56-1.58 (m, 9H) 2.31 (s, 3H) 3.84-3.90 (m, 2H) 3.88 (s, 3H) 4.55 (q, 1H) 6.89 (s, 1H) 7.03 (s, 1H) 7.05 (dd, 1H) 7.20 (d, 1H) 7.38 (s, 1H) 7.66 (s, 1H) 7.75 (d, 1H).

Example 12

2,2,2-Trifluoro-1-(2-(3-methoxy-4-(4-methyl-1H-imidazol-1-yl)phenylamino)-6-((2,2,2-trifluoroethoxy)methyl)pyrimidin-4-yl)ethanol

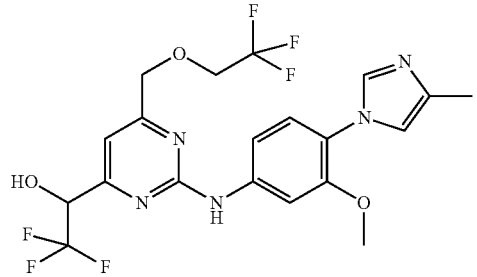 [SMILES: COc1cc(Nc2nc(COCC(F)(F)F)cc(C(O)C(F)(F)F)n2)ccc1-n1cnc(C)c1]

Molecular sieves were added to a solution of 2-(3-methoxy-4-(4-methyl-1H-imidazol-1-yl)phenylamino)-6-((2,2,2-trifluoroethoxy)methyl)pyrimidine-4-carbaldehyde (60 mg, 0.14 mmol) in dry DMF (1 mL) under argon atmosphere. The mixture was stirred for 30 minutes. Potassium carbonate (2 mg, 0.01 mmol) and (trifluoromethyl)trimethylsilane (0.427 mL, 0.21 mmol) were added. The mixture was stirred at ambient temperature for 2 days. The mixture was filtered and purified by preparative HPLC to yield the title compound (7 mg, 10%).

MS (APCI$^+$) m/z 492 (M+H)$^+$. $^1$H NMR (500 MHz, CHLOROFORM-d) ◊ ppm 2.31 (s, 3H) 3.86 (s, 3H) 4.02 (q, 2H) 4.73 (s, 2H) 4.98 (q, 1H) 6.89 (s, 1H) 7.06 (d, 1H) 7.11 (s, 1H) 7.21 (d, 1H) 7.49 (s, 1H) 7.59 (s, 1H) 7.70 (s, 1H).

Example 13

2-Cyclopropyl-1-(2-(3-methoxy-4-(4-methyl-1H-imidazol-1-yl)phenylamino)-6-((2,2,2-trifluoroethoxy)methyl)pyrimidin-4-yl)ethanol

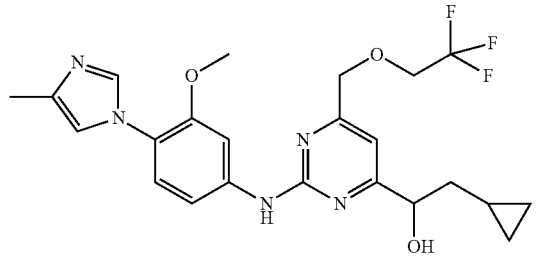 [SMILES: COc1cc(Nc2nc(COCC(F)(F)F)cc(C(O)CC3CC3)n2)ccc1-n1cnc(C)c1]

2-(3-Methoxy-4-(4-methyl-1H-imidazol-1-yl)phenylamino)-6-((2,2,2-trifluoroethoxy)methyl)-pyrimidine-4-carbaldehyde (92 mg, 0.22 mmol) was coevaporated with dioxane and dissolved in THF (5 mL). The solution was cooled on an ice bath and (cyclopropylmethyl)magnesium bromide was added over 30 min. The mixture was quenched by addition of an ammonium chloride (aq, sat). The organic phase was separated and aquous phase was extracted with ethyl acetate (2×5 mL). The combined organic phase was dried over sodium sulfate and filtered through a short pad of silica. The solvents were removed and the residue was purified by preparative HPLC to give the title compound as a dry film 17 mg (16%).

MS (APCI+) m/z 478 (M+H)+. 1H NMR (500 MHz, CHLOROFORM-d) ppm 1.81 (m, 1H) 1.97 (m, 1H) 2.28 (m, 2H) 2.30 (s, 3H) 3.86 (s, 3H) 4.00 (q, 2H) 4.68 (s, 2H) 4.79 (m, 1H) 5.01 (d, 1H) 5.08 (d, 1H) 5.86 (m, 1H) 6.88 (s, 1H) 6.97 (s, 1H) 7.06 (dd, 1H) 7.18 (d, 1H) 7.39 (s, 1H) 7.64 (s, 1H) 7.68 (d, 1H).

Example 14

1-(2-(3-Methoxy-4-(4-methyl-1H-imidazol-1-yl) phenylamino)-6-((2,2,2-trifluoroethoxy)methyl)pyrimidin-4-yl)-2-methylpropan-1-ol

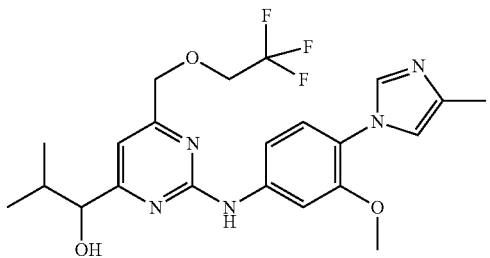 [SMILES: COc1cc(Nc2nc(COCC(F)(F)F)cc(C(O)C(C)C)n2)ccc1-n1cnc(C)c1]

1-(2-Chloro-6-((2,2,2-trifluoroethoxy)methyl)pyrimidin-4-yl)-2-methylpropan-1-ol (20 mg, 0.07 mmol), 3-methoxy-4-(4-methyl-1H-imidazol-1-yl)aniline (13.61 mg, 0.07 mmol), palladium(II) acetate (2.255 mg, 10.04 μmol),2-(dicyclohexylphosphino)biphenyl (3.52 mg, 10.04 μmol), and cesium carbonate (43.6 mg, 0.13 mmol) were mixed in dioxane (3 mL). The vial was flushed with nitrogen, capped and heated by microwave irradiation at 130° C. for 2.5 h. The mixture was filtered through a pad of silica gel, the pad was eluted with DCM and 5% MeOH in DCM. The solvents were evaporated. The residue was purified by preparative HPLC to give the title compound as a dry film, 9 mg (27%).

MS (APCI+) m/z 466 (M+H)+. 1H NMR (400 MHz, CHLOROFORM-d) δ ppm 0.83 (d, 3H) 1.09 (d, 3H) 2.11 (m, 1H) 2.30 (d, 3H) 3.29 (bs, 1H) 3.86 (s, 3H) 4.00 (q, 2H) 4.51 (d, 1H) 4.69 (s, 2H) 6.88 (s, 1H) 6.92 (s, 1H) 7.06 (dd, 1H) 7.18 (d, 1H) 7.42 (s, 1H) 7.66 (d, 1H) 7.67 (d, 1H).

Example 15

2-(2-(3-Methoxy-4-(4-methyl-1H-imidazol-1-yl) phenylamino)-6-((2,2,2-trifluoroethoxy)-methyl) pyrimidin-4-yl)propan-2-ol

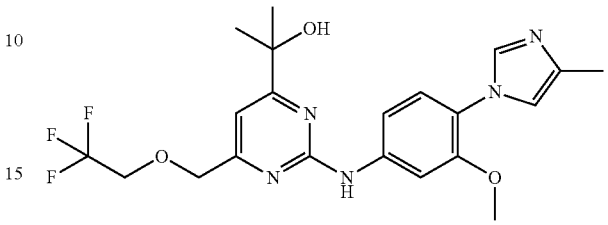

1-(2-(3-Methoxy-4-(4-methyl-1H-imidazol-1-yl)phenylamino)-6-((2,2,2-trifluoroethoxy)-methyl)pyrimidin-4-yl)ethanone (178 mg, 0.41 mmol) was dissolved in THF (5 mL). The mixture was added to methylmagnesium bromide (3 M in THF, 1.090 mL, 3.27 mmol) in THF (5 mL). The mixture was stirred at rt for 5 min. The mixture was cooled at 0° C. and ammonium chloride (aq) was added. The mixture was extracted by EtOAc, the organic phase was dried over sodium sulfate and concentrated. The residue was purified by column chromatography on silica eluting with a gradient of methanol in DCM to give the title compound as a solid 107 mg (58%).

MS (APCI+) m/z 452 (M+H)+. 1H NMR (400 MHz, DMSO-d6) δ ppm 1.47 (s, 6H) 2.14 (d, 3H) 3.80 (s, 3H) 4.28 (q, 2H) 4.69 (s, 2H) 5.40 (s, 1H) 7.03 (t, 1H) 7.22 (m, 2H) 7.29 (m, 1H) 7.66 (d, 1H) 8.01 (d, 1H) 9.82 (s, 1H).

Example 16

4-((Cyclopropylmethoxy)methyl)-N-(3-methoxy-4-(4-methyl-1H-imidazol-1-yl)phenyl)-6-((2,2,2-trifluoroethoxy)methyl)pyrimidin-2-amine

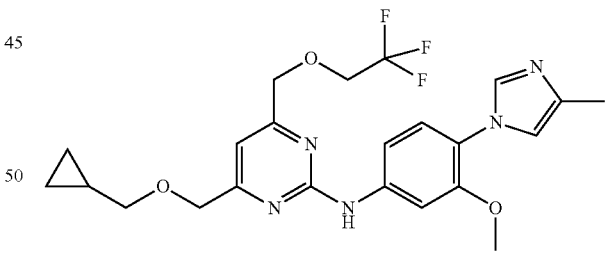

2-Chloro-4-((cyclopropylmethoxy)methyl)-6-((2,2,2-trifluoroethoxy)methyl)pyrimidine (approximately 50% pure, 33 mg, 0.11 mmol), 3-methoxy-4-(4-methyl-1H-imidazol-1-yl)aniline (26 mg, 0.13 mmol), palladium (II) acetate (4 mg, 0.02 mmol), 2-(dicyclohexylphosphino)-biphenyl (6 mg, 0.02 mmol) cesium carbonate (69 mg, 0.21 mmol) and dioxane (2 mL) were mixed in a vial. The vial was capped, evacuated and flushed with nitrogen. The mixture was heated by microwave irradiation at 120° C. for 1.5 h. The mixture was filtered through a pad of silica, the pad was washed with 10% methanol in ethyl acetate. The solvents were evaporated and the residue was purified by preparative HPLC to give the title compound as a dry film, 15 mg (28%).

MS (APCI⁺) m/z 478 (M+H)⁺. ¹H NMR (400 MHz, CHLOROFORM-d) δ ppm 0.23-0.32 (m, 2H) 0.55-0.65 (m, 2H) 1.09-1.21 (m, 1H) 2.31 (d, 3H) 3.44 (d, 2H) 3.86 (s, 3H) 4.00 (q, 2H) 4.55 (s, 2H) 4.68 (s, 2H) 6.88 (t, 1H) 7.08 (dd, 1H) 7.12 (s, 1H) 7.17 (d, 1H) 7.32 (s, 1H) 7.66 (d, 1H) 7.74 (d, 1H).

Example 17

2-(6-(((3,3-Difluorocyclobutyl)methoxy)methyl)-2-(3-methoxy-4-(4-methyl-1H-imidazol-1-yl)phenylamino)pyrimidin-4-yl)propan-2-ol

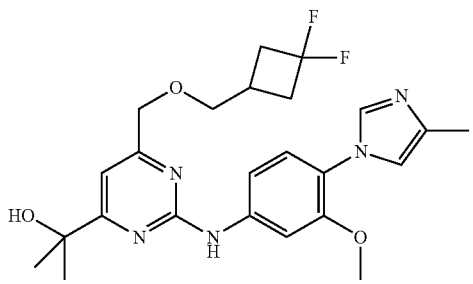 [SMILES: COc1cc(Nc2nc(COCC3CC(F)(F)C3)cc(C(C)(C)O)n2)ccc1-n1cnc(C)c1]

Methylmagnesium bromide (0.105 mL, 0.31 mmol) was added to an ice-cold solution of 1-(6-(((3,3-difluorocyclobutyl)methoxy)methyl)-2-(3-methoxy-4-(4-methyl-1H-imidazol-1-yl)-phenylamino)pyrimidin-4-yl)ethanone (16 mg, 0.03 mmol) in tetrahydrofuran (5 mL) under argon atmosphere. The mixture was stirred for 10 min. Methylmagnesium bromide (0.058 mL, 0.17 mmol) was added and the mixture was stirred for 10 minutes. The reaction was quenched with of ammonium chloride (aq, sat). The mixture was concentrated. The residue was extracted with dichloromethane. The organic phase was dried over sodium sulfate and concentrated. The residue was purified by preparative HPLC to give the title compound as a dry film (4 mg, 24%).

MS (APCI⁺) m/z 474 (M+H)⁺. ¹H NMR (500 MHz, CHLOROFORM-d) δ ppm 1.57 (s, 6H) 2.38-2.57 (m, 6H) 2.66-2.77 (m, 2H) 3.65 (d, 2H) 3.90 (s, 3H) 4.55 (s, 2H) 6.95 (s, 1H) 7.07 (s, 1H) 7.11 (d, 1H) 7.22 (d, 1H) 7.33 (s, 1H) 7.79 (s, 1H) 8.08 (br. s, 1H).

Example 18

2-(2-(3-Methoxy-4-(4-methyl-1H-imidazol-1-yl)phenylamino)-6-((3,3,3-trifluoropropoxy)-methyl)pyrimidin-4-yl)propan-2-ol

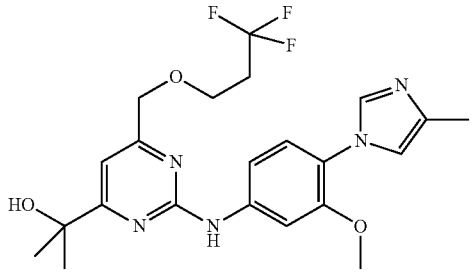 [SMILES: COc1cc(Nc2nc(COCCC(F)(F)F)cc(C(C)(C)O)n2)ccc1-n1cnc(C)c1]

To an ice-cold solution of methylmagnesium bromide (0.950 mL, 2.85 mmol) in tetrahydrofuran (10 mL) a solution of ice-cold 1-(2-(3-methoxy-4-(4-methyl-1H-imidazol-1-yl)phenylamino)-6-((3,3,3-trifluoropropoxy)methyl)pyrimidin-4-yl)ethanone (85 mg, 0.19 mmol) in tetrahydrofuran (6 mL) was added over 5 min. The mixture was stirred on ice-bath for 30 minutes before it was quenched ammonium chloride (aq, sat). The solvent volume was reduced by evaporation. The mixture was extracted with dichloromethane and the organic phase was passed through a phase separator. The residue was purified by preparative HPLC to give the title compound as a solid 53 mg (60%).

MS (APCI⁺) m/z 466 (M+H)⁺. ¹H NMR (500 MHz, CHLOROFORM-d) δ ppm 1.56 (s, 6H) 2.31 (s, 3H) 2.52 (qt, 2H) 3.83 (t, 2H) 3.87 (s, 3H) 4.25 (br. s, 1H) 4.55 (s, 2H) 6.89 (s, 1H) 7.03 (s, 1H) 7.07 (dd, 1H) 7.19 (d, 1H) 7.38 (s, 1H) 7.69 (d, 1H) 7.66 (d, 1H).

Example 19

2-(6-(((3,3-Difluorocyclobutyl)methoxy)methyl)-2-(3-methoxy-4-(6-methylpyridazin-4-yl)phenylamino)pyrimidin-4-yl)propan-2-ol

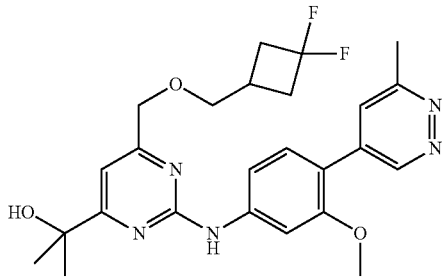 [SMILES: COc1cc(Nc2nc(COCC3CC(F)(F)C3)cc(C(C)(C)O)n2)ccc1-c1cnnc(C)c1]

To an ice-cold solution of methylmagnesium bromide (1.430 mL, 2.00 mmol) in THF (6 mL) a solution of 1-(6-(((3,3-difluorocyclobutyl)methoxy)methyl)-2-(3-methoxy-4-(6-methylpyridazin-4-yl)phenylamino)pyrimidin-4-yl)ethanone (94 mg, 0.20 mmol) in THF (3 mL) was added over 5 min. The mixture was stirred on ice-bath for 30 minutes before it was quenched with ammonium chloride (aq, sat). The solvent volume was reduced by evaporation. The mixture was extracted with dichloromethane and the organic phase was passed through a phase separator. The residue was purified by preparative HPLC to give the title compound as a dry film 38 mg (39%).

MS (APCI⁺) m/z 486 (M+H)⁺. ¹H NMR (500 MHz, CHLOROFORM-d) δ ppm 1.57 (s, 6H) 2.38-2.56 (m, 3H) 2.65-2.74 (m, 2H) 2.76 (s, 3H) 3.65 (d, 2H) 3.91 (s, 3H) 4.13 (br. s, 1H) 4.56 (s, 2H) 7.04 (s, 1H) 7.16 (dd, 1H) 7.36 (d, 1H) 7.44 (s, 1H) 7.50-7.54 (m, 1H) 7.72 (d, 1H) 9.28 (s, 1H).

Example 20

4-(Azetidin-1-yl)-N-(3-methoxy-4-(4-methyl-1H-imidazol-1-yl)phenyl)-6-((2,2,2-trifluoroethoxy)methyl)pyrimidin-2-amine

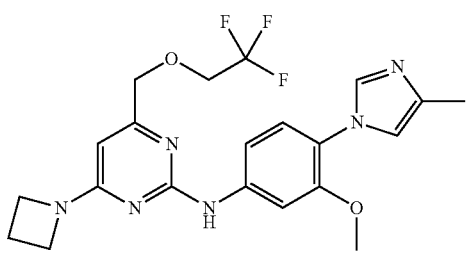 [SMILES: COc1cc(Nc2nc(COCC(F)(F)F)cc(N3CCC3)n2)ccc1-n1cnc(C)c1]

A mixture of 4-(azetidin-1-yl)-2-chloro-6-((2,2,2-trifluoroethoxy)methyl)pyrimidine (31 mg, 0.11 mmol), 3-methoxy-4-(4-methyl-1H-imidazol-1-yl)aniline (22.37 mg, 0.11 mmol), cesium carbonate (71.7 mg, 0.22 mmol), palladium(II) acetate (3.71 mg, 0.02 mmol) and 2-(dicyclohexylphosphino)biphenyl (5.79 mg, 0.02 mmol) in dioxane (2 mL) was heated under argon at 120° C. for 90 minutes in microwave reactor. The mixture was filtered through a short silica plug which was washed with 10% methanol in ethyl acetate and the mixture was concentrated in vacuum. The residue was purified by preparative HPLC give the title compound as a dry film (41 mg, 83%).

MS (APCI$^+$) m/z 449(M+H)$^+$. $^1$H NMR (400 MHz, CHLOROFORM-d) ◊ ppm 2.30 (d, 3H) 2.41-2.52 (m, 2H) 3.85 (s, 3H) 3.96 (q, 2H) 4.11-4.19 (m, 4H) 4.51 (s, 2H) 5.88 (s, 1H) 6.86 (s, 1H) 6.91 (dd, 1H) 7.05 (s, 1H) 7.12 (d, 1H) 7.62 (d, 1H) 7.92 (d, 1H).

Example 21

4-(Azetidin-1-yl)-N-(3-methoxy-4-(6-methylpyridazin-4-yl)phenyl)-6-((2,2,2-trifluoroethoxy)methyl)pyrimidin-2-amine

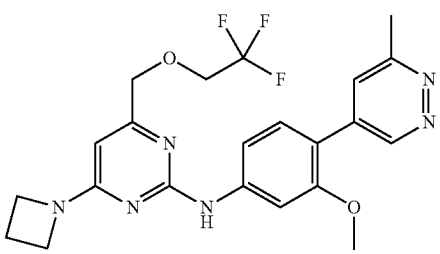 [SMILES: COc1cc(Nc2nc(COCC(F)(F)F)cc(N3CCC3)n2)ccc1-c1cnnc(C)c1]

A mixture of 4-(azetidin-1-yl)-2-chloro-6-((2,2,2-trifluoroethoxy)methyl)pyrimidine (30 mg, 0.11 mmol), 3-methoxy-4-(6-methylpyridazin-4-yl)aniline (23 mg, 0.11 mmol), cesium carbonate (69 mg, 0.21 mmol), palladium(II) acetate (4 mg, 0.02 mmol) and 2-(dicyclohexyl-phosphino) biphenyl (6 mg, 0.02 mmol) in dioxane (2 mL) was heated under argon at 120° C. for 90 minutes in a microwave reactor. The mixture was filtered through a short silica plug which was washed with 10% solution of methanol in EtOAc (75 mL). The eluate was concentrated and the residue was purified by preparative HPLC to give the title compound as a solid 14 mg (29%).

MS (APCI$^+$) m/z 461(M+H)$^+$. $^1$H NMR (500 MHz, CHLOROFORM-d) ◊ ppm 2.42-2.50 (m, 2H) 2.73 (s, 3H) 3.88 (s, 3H) 3.96 (q, 2H) 4.10-4.20 (m, 4H) 4.51 (s, 2H) 5.88 (s, 1H) 7.00 (dd, 1H) 7.23 (s, 1H) 7.28 (d, 1H) 7.48 (d, 1H) 7.93 (d, 1H) 9.26 (d, 1H).

Example 22

4-(4,4-Difluoropiperidin-1-yl)-N-(3-methoxy-4-(6-methylpyridazin-4-yl)phenyl)-6-((2,2,2-trifluoroethoxy)methyl)pyrimidin-2-amine

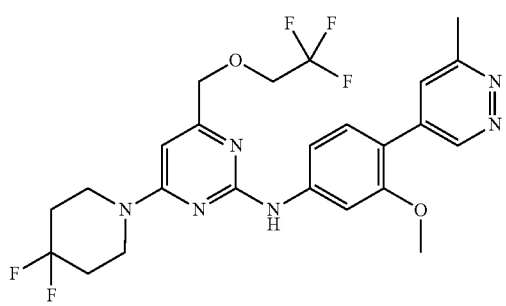 [SMILES: COc1cc(Nc2nc(COCC(F)(F)F)cc(N3CCC(F)(F)CC3)n2)ccc1-c1cnnc(C)c1]

A mixture of 2-chloro-4-(4,4-difluoropiperidin-1-yl)-6-((2,2,2-trifluoroethoxy)methyl)pyrimidine (40 mg, 0.12 mmol), 3-methoxy-4-(6-methylpyridazin-4-yl)aniline (25 mg, 0.12 mmol), cesium carbonate (75 mg, 0.23 mmol), palladium(II) acetate (4 mg, 0.02 mmol) and 2-(dicyclohexylphosphino)biphenyl (6 mg, 0.02 mmol) in dioxane (2 mL) was heated under argon at 120° C. for 90 minutes in a microwave reactor. The mixture was filtered through a short silica gel plug which was washed with 10% solution of methanol in ethyl acetate (75 mL) and the eluate was concentrated in vacuum. The residue was purified by preparative HPLC to give the title compound as a solid, 35 mg (58%).

MS (APCI$^+$) m/z 525(M+H)$^+$. $^1$H NMR (500 MHz, CHLOROFORM-d) ◊ ppm 1.98-2.10 (m, 4H) 2.73 (s, 3H) 3.81-3.85 (m, 4H) 3.87 (s, 3H) 3.98 (q, 2H) 4.56 (s, 2H) 6.32 (s, 1H) 7.12 (dd, 1H) 7.23 (s, 1H) 7.31 (d, 1H) 7.49 (d, 1H) 7.64 (d, 1H) 9.27 (d, 1H).

Example 23

$N^4$-Isopropyl-$N^2$-(3-methoxy-4-(6-methylpyridazin-4-yl)phenyl)-6-((2,2,2-trifluoroethoxy)-methyl)pyrimidine-2,4-diamine

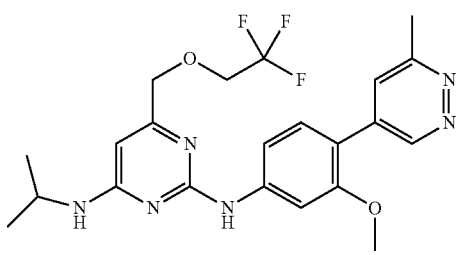 [SMILES: COc1cc(Nc2nc(COCC(F)(F)F)cc(NC(C)C)n2)ccc1-c1cnnc(C)c1]

A mixture of 2-chloro-N-isopropyl-6-((2,2,2-trifluoroethoxy)methyl)pyrimidin-4-amine (41 mg, 0.14 mmol), 3-methoxy-4-(6-methylpyridazin-4-yl)aniline (31 mg, 0.14 mmol), cesium carbonate (94 mg, 0.29 mmol), palladium(II) acetate (5 mg, 0.02 mmol) and 2-(dicyclohexyl-phosphino) biphenyl (8 mg, 0.02 mmol) in dioxane (2 mL) was heated under argon at 120° C. for 90 minutes in a microwave reactor. The mixture was filtered through a short silica gel plug which was washed with 10% solution of methanol in ethyl acetate. The eluate was concentrated in vacuum and the residue was purified by preparative HPLC to give the title compound 32 mg (48%).

MS (APCI$^+$) m/z 463 (M+H)$^+$. $^1$H NMR (500 MHz, METHANOL-d$_4$) ▯ ppm 1.23 (d, 6H) 2.66 (s, 3H) 3.88 (s, 3H) 4.05 (q, 2H) 4.17-4.34 (m., 1H) 4.44 (s, 2H) 6.06 (s, 1H) 7.27 (d, 1H) 7.36 (d, 1H) 7.68-7.73 (m, 1H) 7.82 (br. s, 1H) 9.22 (br. s, 1H).

Example 24

N$^2$-(3-Methoxy-4-(6-methylpyridazin-4-yl)phenyl)-N$^4$-methyl-6-((2,2,2-trifluoroethoxy)-methyl)pyrimidine-2,4-diamine

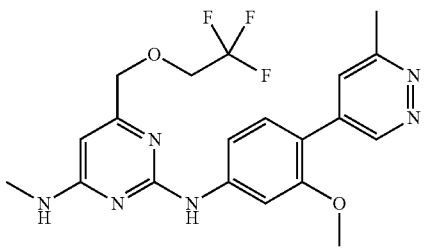 [SMILES: CNc1cc(COCC(F)(F)F)nc(Nc2ccc(-c3cnnc(C)c3)c(OC)c2)n1]

A mixture of 2-chloro-N-methyl-6-((2,2,2-trifluoroethoxy)methyl)pyrimidin-4-amine (50 mg, 0.20 mmol), 3-methoxy-4-(6-methylpyridazin-4-yl)aniline (42 mg, 0.20 mmol), cesium rbonate (127 mg, 0.39 mmol), palladium (II) acetate (7 mg, 0.03 mmol) and 2-(dicyclohexylphosphino)-biphenyl (10 mg, 0.03 mmol) in dioxane (2 mL) was heated under argon at 120° C. for 90 minutes in a microwave reactor. 2-Chloro-N-methyl-6-((2,2,2-trifluoroethoxy) methyl)pyrimidin-4-amine (72 mg, 0.28 mmol, 1.4 eq), palladium(II) acetate (7 mg) and 2-(dicyclohexylphosphino) biphenyl (10 mg) was added and the mixture was heated at 120° C. for 90 minutes in a microwave reactor. The mixture was filtered through a short silica gel plug which was washed with 10% solution of methanol in ethyl acetate (75 mL). The eluate was concentrated in vacuum and the residue was purified by preparative to give the title compound as a solid, 22 mg (26%).

MS (APCI$^+$) m/z 435 (M+H)$^+$. $^1$H NMR (500 MHz, CHLOROFORM-d) ▯ ppm 2.73 (s, 3H) 3.03 (br. s, 3H) 3.88 (s, 3H) 3.97 (q, 2H) 4.53 (s, 2H) 5.22 (br. s, 1H) 6.10 (s, 1H) 7.10-7.15 (m, 1H) 7.28-7.37 (m, 2H) 7.50 (d, 1H) 7.77 (br. s, 1H) 9.26 (d, 1H).

Example 25

N$^4$-Benzyl-N$^2$-(3-methoxy-4-(4-methyl-1H-imidazol-1-yl)phenyl)-N$^4$-methyl-6-((2,2,2-trifluoroethoxy)methyl)pyrimidine-2,4-diamine

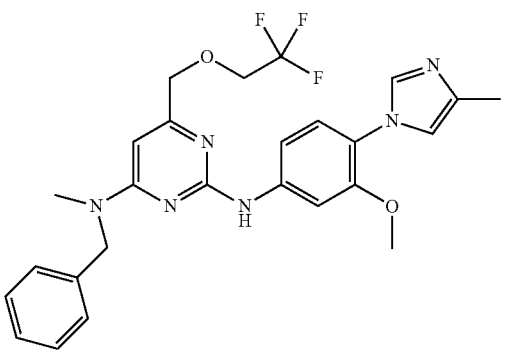 [SMILES: COc1cc(Nc2nc(COCC(F)(F)F)cc(N(C)Cc3ccccc3)n2)ccc1-n1cnc(C)c1]

A mixture of N-benzyl-2-chloro-N-methyl-6-((2,2,2-trifluoroethoxy)methyl)pyrimidin-4-amine (197 mg, 0.57 mmol), 3-methoxy-4-(4-methyl-1H-imidazol-1-yl)aniline (116 mg, 0.57 mmol), cesium carbonate (371 mg, 1.14 mmol), palladium (II) acetate (19 mg, 0.09 mmol) and 2-(dicyclohexylphosphino)biphenyl (30 mg, 0.09 mmol) in dioxane (4 mL) was heated under argon at 120° C. for 90 minutes in a microwave reactor. The mixture was filtered through a short silica gel plug which was washed with 10% solution of methanol in ethyl acetate (75 mL). The eluate was concentrated in vacuum and the residue was purified by preparative HPLC to give the title compound as a solid 194 mg (66%).

MS (APCI$^+$) m/z 513 (M+H)$^+$. $^1$H NMR (400 MHz, MeOH) ▯ ppm 2.21 (d, 3H) 3.10 (br. s, 3H) 3.62 (br. s, 3H) 4.06 (q, 2H) 4.53 (s, 2H) 6.28 (s, 1H) 6.93 (s, 1H) 7.12 (s, 2H) 7.22-7.28 (m, 3H) 7.30-7.36 (m, 2H) 7.62-7.65 (m, 1H) 7.80 (s, 1H).

Example 26

4-(4,4-Difluoropiperidin-1-yl)-N-(3-methoxy-4-(4-methyl-1H-imidazol-1-yl)phenyl)-6-((2,2,2-trifluoroethoxy)methyl)pyrimidin-2-amine

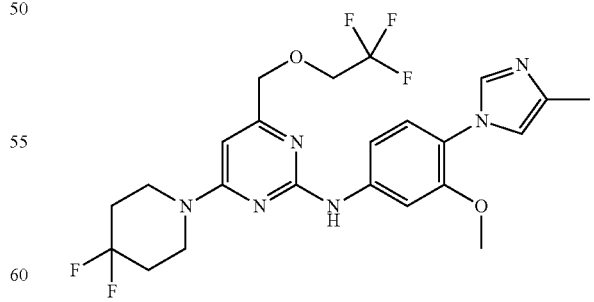

A mixture of 2-chloro-4-(4,4-difluoropiperidin-1-yl)-6-((2,2,2-trifluoroethoxy)methyl)pyrimidine (97 mg, 0.28 mmol), 3-methoxy-4-(4-methyl-1H-imidazol-1-yl)aniline (57 mg, 0.28 mmol), cesium carbonate (183 mg, 0.56 mmol), palladium acetate (9 mg, 0.04 mmol) and 2-(dicyclohexylphosphino)biphenyl (15 mg, 0.04 mmol) was stirred under argon at 120° C. for 90 minutes in a microwave reactor. The mixture was filtered through a short silica gel plug which was washed with 10% solution of methanol in ethyl acetate (75 mL). The eluate was concentrated in vacuum and the residue was purified by preparative HPLC to give the title compound as a gum, 103 mg (72%).

MS (APCI$^+$) m/z 513 (M+H)$^+$. $^1$H NMR (500 MHz, CDCl$_3$) ⊠ 2.00-2.09 (m, 4H), 2.29-2.32 (m, 3H), 3.81-3.87 (m, 7H), 3.98 (q, 2H), 4.55 (s, 2H), 6.31 (s, 1H), 6.87 (s, 1H), 7.00-7.05 (m, 2H), 7.15 (d, 1H), 7.60-7.65 (m, 2H).

Example 27

2-(2-(3-Methoxy-4-(4-methyl-1H-imidazol-1-yl) phenylamino)-6-(methoxymethyl)pyrimidin-4-yl) propan-2-ol

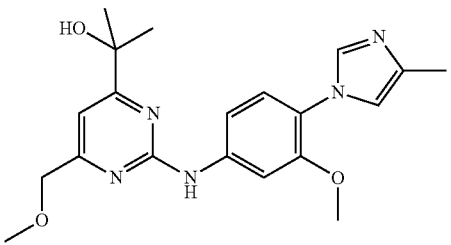

1-(2-(3-Methoxy-4-(4-methyl-1H-imidazol-1-yl)phe-nylamino)-6-(methoxymethyl)pyrimidin-4-yl)ethanone (160 mg, 0.44 mmol) in tetrahydrofuran (20 mL) was added dropwise to an ice-cold solution of methylmagnesium bromide (3.11 mL, 4.35 mmol) in tetrahydrofuran (10 mL). The mixture was stirred on ice-bath for 30 minutes and quenched with ammonium chloride (sat, aq). The mixture was extracted with dichloromethane, the organic phase was passed through a phase separator containing 1 cm layer of magnesium sulfate and the eluate was concentrated in vacuum. The residue was purified preparative HPLC to give the title compound as a solid, 124 mg (74%).

MS (APCI$^+$) m/z 384 (M+H)$^+$. $^1$H NMR (400 MHz, CDCl$_3$) ⊠ 1.56 (s, 6H), 2.35-2.38 (m, 3H), 3.54 (s, 3H), 3.89 (s, 3H), 4.10 (s, 1H), 4.49 (s, 2H), 6.90-6.93 (m, 1H), 7.01-7.06 (m, 2H), 7.20 (d, 1H), 7.77 (d, 1H), 7.80 (br. s, 1H).

Example 28

Cyclopropyl(2-(3-methoxy-4-(4-methyl-1H-imida-zol-1-yl)phenylamino)-6-((2,2,2-trifluoroethoxy) methyl)pyrimidin-4-yl)methanol

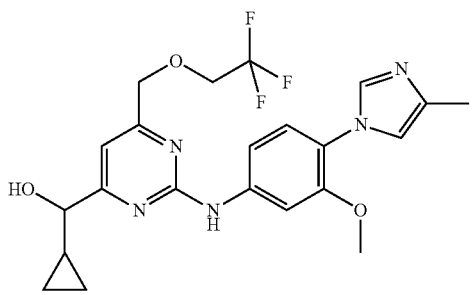 [SMILES: COc1cc(Nc2nc(COCC(F)(F)F)cc(C(O)C3CC3)n2)ccc1-n1cnc(C)c1]

To an ice-cold solution of cyclopropylmagnesium bromide (1.90 mL, 0.95 mmol) in THF (10 mL), a solution of 2-(3-methoxy-4-(4-methyl-1H-imidazol-1-yl)phe-nylamino)-6-((2,2,2-trifluoroethoxy)methyl)pyrimidine-4-carbaldehyde (40 mg, 0.09 mmol) in THF (6 mL) was added over 5 min. The mixture was stirred on ice-bath for 30 minutes before it was quenched with ammonium chloride (aq, sat). The solvent volume was reduced by evaporation. The mixture was extracted with dichloromethane, the organic phase was passed through a phase separator and concentrated in vacuum. The residue was purified by preparative HPLC to give the title compound as a dry film, 7 mg (16%).

MS (APCI$^+$) m/z 464 (M+H)$^+$. $^1$H NMR (500 MHz, CHLOROFORM-d) ⊠ ppm 0.54-0.69 (m, 4H) 1.10-1.18 (m, 1H) 2.29-2.32 (m, 3H) 3.87 (s, 3H) 3.97-4.09 (m, 3H) 4.70 (s, 2H) 6.89 (s, 1H) 7.05 (s, 1H) 7.10 (dd, 1H) 7.19 (d, 1H) 7.35 (s, 1H) 7.65 (dd, 2H).

Example 29

2-(6-((Cyclopropylmethoxy)methyl)-2-(3-methoxy-4-(4-methyl-1H-imidazol-1-yl)phenylamino)pyrimi-din-4-yl)propan-2-ol

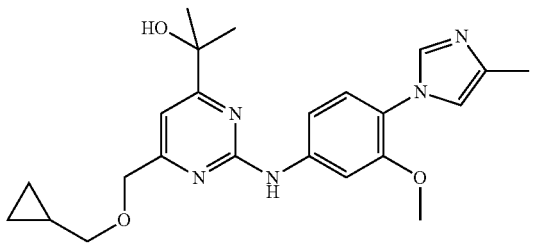 [SMILES: COc1cc(Nc2nc(COCC3CC3)cc(C(C)(C)O)n2)ccc1-n1cnc(C)c1]

To an ice-cold solution of methylmagnesium bromide (1.58 mL, 2.21 mmol) in THF (5 mL) 1-(6-((cyclopropyl-methoxy)methyl)-2-(3-methoxy-4-(4-methyl-1H-imidazol-1-yl)phenylamino)-pyrimidin-4-yl)ethanone (90 mg, 0.22 mmol) in THF (20 mL) was added dropwise and the mixture was stirred on ice-bath for 30 minutes. The reaction was quenched with ammonium chloride (aq, sat) and brine was added. The mixture was extracted with dichloromethane, the organic phase was passed through a phase separator containing 1 cm layer of magnesium sulfate and the solvents were removed in vacuum. The residue was purified by preparative HPLC to give the title compound as a solid, 50 mg (54%).

MS (APCI$^+$) m/z 424 (M+H)$^+$. $^1$H NMR (500 MHz, CDCl$_3$) ⊠ ppm 0.23-0.27 (m, 2H), 0.56-0.61 (m, 2H), 1.09-1.18 (m, 1H), 1.56 (s, 6H), 2.27-2.31 (m, 3H), 3.44 (d, 2H), 3.86 (s, 3H), 4.45 (br. s, 1H), 4.55 (s, 2H), 6.87 (s, 1H), 7.05 (dd, 1H), 7.07 (s, 1H), 7.17 (d, 1H), 7.54 (s, 1H), 7.64 (s, 1H), 7.73 (d, 1H).

Example 30

6-((Cyclopropylmethoxy)methyl)-N2-(3-methoxy-4-(4-methyl-1H-imidazol-1-yl)phenyl)-N4-methylpyrimidine-2,4-diamine

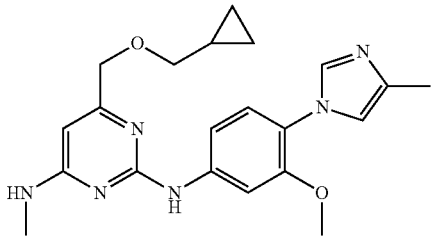 [SMILES: CNc1cc(COCC2CC2)nc(Nc2ccc(-n3cnc(C)c3)c(OC)c2)n1]

A mixture of 2-chloro-6-((cyclopropylmethoxy)methyl)-N-methylpyrimidin-4-amine (41 mg, 0.18 mmol), 3-methoxy-4-(4-methyl-1H-imidazol-1-yl)aniline (73 mg, 0.36 mmol), cesium carbonate (117 mg, 0.36 mmol), palladium acetate (6 mg, 0.03 mmol) and 2-(dicyclohexyl-phosphino)biphenyl (9 mg, 0.03 mmol) was stirred under argon at 120° C. for 90 minutes in microwave oven. The mixture was filtered through a short silica gel plug which was washed with 10% solution of methanol in ethyl acetate (75 mL). The eluate was concentrated and the residue was purified by preparative HPLC to give the title compound as a dry film (30 mg, 42%).

MS (APCI$^+$) m/z 395 (M+H)$^+$. $^1$H NMR (500 MHz, CDCl$_3$) ▫ ppm 0.23-0.27 (m, 2H), 0.55-0.60 (m, 2H), 1.08-1.17 (m, 1H), 2.29 (s, 3H), 3.00 (d, 3H), 3.41 (d, 2H), 3.83 (s, 3H), 4.39 (s, 2H), 5.08 (br. s, 1H), 6.11 (s, 1H), 6.85 (s, 1H), 7.00 (dd, 1H), 7.11 (d, 1H), 7.17 (br. s, 1H), 7.59-7.63 (m, 1H), 7.77 (br. s, 1H).

Example 31

1-(2-(3-Methoxy-4-(4-methoxy-1H-imidazol-1-yl)phenylamino)-6-((2,2,2-trifluoroethoxy)-methyl)pyrimidin-4-yl)ethanol

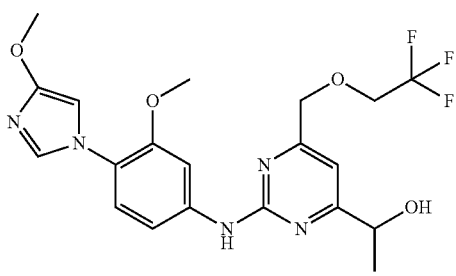 [SMILES: COc1cn(-c2ccc(Nc3nc(COCC(F)(F)F)cc(C(C)O)n3)cc2OC)cn1]

To a stirred solution of 1-(2-(3-methoxy-4-(4-methoxy-1H-imidazol-1-yl)phenylamino)-6-((2,2,2-trifluoroethoxy)methyl)pyrimidin-4-yl)ethanone (0.1 g, 0.22 mmol) in ethanol (5 mL) sodium borohydride (0.034 g, 0.89 mmol) was added. The mixture was stirred at rt for 10 min. Acetone (2 mL) was added and mixture was stirred for 20 min. The mixture was filtered, the filtrate was concentrated in vacuum and the residue was purified by preparative HPLC to give the title compound as a dry film, 50 mg (50%).

MS (APCI$^+$) m/z 454 (M+H)$^+$. $^1$H NMR (500 MHz, CHLOROFORM-d): ▫ ppm: 1.54 (d, 3H), 3.86 (s, 3H), 3.87 (s, 3H), 4.00 (q, 2H), 4.68 (s, 2H), 4.81 (q, 1H), 6.49 (d, 1H), 6.97 (s, 1H), 7.10 (dd, 1H), 7.20 (d, 1H), 7.41 (d, 1H), 7.49 (s, 1H), 7.68 (d, 1H).

Example 32

2-(2-(3-Methoxy-4-(4-methoxy-1H-imidazol-1-yl)phenylamino)-6-((2,2,2-trifluoroethoxy)-methyl)pyrimidin-4-yl)propan-2-ol

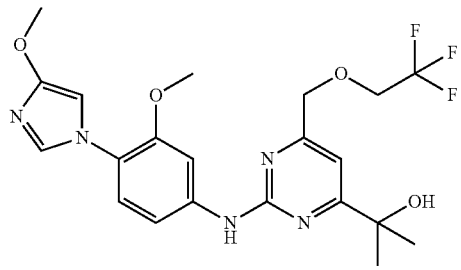 [SMILES: COc1cn(-c2ccc(Nc3nc(COCC(F)(F)F)cc(C(C)(C)O)n3)cc2OC)cn1]

1-(2-(3-Methoxy-4-(4-methoxy-1H-imidazol-1-yl)phenylamino)-6-((2,2,2-trifluoroethoxy)-methyl)pyrimidin-4-yl)ethanone (145 mg, 0.32 mmol) was coevaporated with dioxane and dissolved in THF (10 mL). The mixture was added slowly to a well stirred solution of methylmagnesium bromide (0.857 mL, 3 M solution, 2.57 mmol) in THF (5 mL). The mixture was stirred at rt for 5 min. The mixture was cooled on ice bath and ammonium chloride (aq, 5 mL) was added. The mixture was extracted with ethyl acetate (2×10 mL), the organic phase was filtered and concentrated in vacuum. The residue was separated purified by preparative HPLC to give the title compound as a dry film, 68 mg (46%).

MS (APCI$^+$) m/z 468 (M+H)$^+$. $^1$H NMR (500 MHz, ACETONITRILE-d$_3$) ▫ ▫ ppm: 1.50 (s, 6H), 3.76 (s, 3H), 3.85 (s, 3H), 3.97 (br. s, 1H), 4.11 (q, 2H), 4.66 (s, 2H), 6.57 (s, 1H), 7.15 (s, 1H), 7.22 (s, 2H), 7.37 (s, 1H), 7.85 (s, 1H), 8.12 (br. s, 1H).

Example 33

N$^4$-(Cyclopropylmethyl)-N$^2$-(3-methoxy-4-(4-methyl-1H-imidazol-1-yl)phenyl)-6-((2,2,2-trifluoroethoxy)methyl)pyrimidine-2,4-diamine

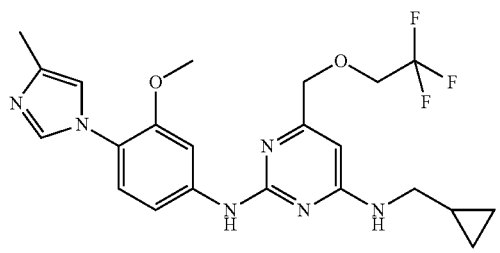 [SMILES: COc1cc(Nc2nc(COCC(F)(F)F)cc(NCC3CC3)n2)ccc1-n1cnc(C)c1]

A mixture of 3-methoxy-4-(4-methyl-1H-imidazol-1-yl)aniline (99 mg, 0.49 mmol), 2-chloro-N-(cyclopropylmethyl)-6-((2,2,2-trifluoroethoxy)methyl)pyrimidin-4-amine (72 mg, 0.24 mmol), cesium carbonate (159 mg, 0.49 mmol), palladium(II) acetate (8.20 mg, 0.04 mmol) and 2-(dicyclohexylphosphino)biphenyl (12.80 mg, 0.04 mmol) in dioxane (1.5 mL) was heated at 120° C. by microwave irradiation under nitrogen atmosphere for 90 minutes. The mixture was filtered through diatomeous earth, the pad was eluted with methanol. The eluate was concentrated and the residue was purified by preparative chromatography to give the title compound as a dry film, 65 mg (58%).

MS (APCI$^+$) m/z 463 (M+H)$^+$. $^1$H NMR (500 MHz, ACETONITRILE-d$_3$) ☒ 0.21-0.26 (m, 2H), 0.46-0.52 (m, 2H), 1.04-1.15 (m, 1H), 2.19 (s, 3H), 3.27 (br. s, 2H), 3.84 (s, 3H), 4.07 (q, 2H), 4.45 (s, 2H), 5.94 (br. s, 1H), 6.06 (s, 1H), 6.92 (s, 1H), 7.15 (br. s, 2H), 7.54 (d, 1H), 7.59 (br. s, 1H), 7.93 (br. s, 1H).

Example 34

N$^4$-Cyclopropyl-N$^2$-(3-methoxy-4-(4-methyl-1H-imidazol-1-yl)phenyl)-6-((2,2,2-trifluoroethoxy)methyl)pyrimidine-2,4-diamine

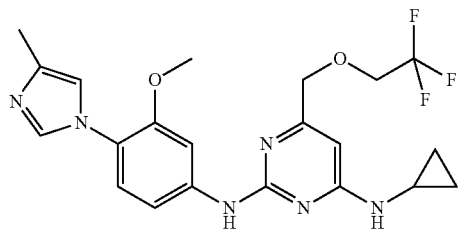 [SMILES: COc1cc(Nc2nc(COCC(F)(F)F)cc(NC3CC3)n2)ccc1-n1cnc(C)c1]

A mixture of 3-methoxy-4-(4-methyl-1H-imidazol-1-yl)aniline (91 mg, 0.45 mmol), 2-chloro-N-cyclopropyl-6-((2,2,2-trifluoroethoxy)methyl)pyrimidin-4-amine (63 mg, 0.22 mmol), cesium carbonate (146 mg, 0.45 mmol), palladium (II) acetate (8 mg, 0.03 mmol) and 2-(dicyclohexyl-phosphino)biphenyl (12 mg, 0.03 mmol) in dioxane (1.5 mL) was heated at 120° C. in a microwave reactor for 90 minutes. The mixture was filtered through diatomeous earth, the filter pad was eluted with methanol. The eluate was concentrated in vacuum and the residue purified by preparative chromatography to give the title compound as a solid, 45 mg (45%).

MS (APCI$^+$) m/z 449 (M+H)$^+$. $^1$H NMR (500 MHz, ACETONITRILE-d$_3$) ☒ 0.51-0.58 (m, 2H), 0.76-0.81 (m, 2H), 2.18-2.19 (m, 3H), 2.63 (br. s, 1H), 3.82 (s, 3H), 4.08 (q, 2H), 4.50 (s, 2H), 6.00 (br. s, 1H), 6.92 (s, 1H), 7.15 (d, 1H), 7.25-7.37 (m, 1H), 7.54 (d, 1H), 7.57 (br. s, 1H), 7.78 (d, 1H).

Example 35

N$^2$-(3-Methoxy-4-(4-methyl-1H-imidazol-1-yl)phenyl)-N$^4$-(oxetan-3-yl)-6-((2,2,2-trifluoroethoxy)methyl)pyrimidine-2,4-diamine

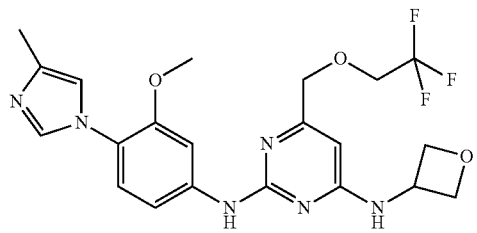 [SMILES: COc1cc(Nc2nc(COCC(F)(F)F)cc(NC3COC3)n2)ccc1-n1cnc(C)c1]

A mixture of 3-methoxy-4-(4-methyl-1H-imidazol-1-yl)aniline (78 mg, 0.38 mmol), 2-chloro-N-(oxetan-3-yl)-6-((2,2,2-trifluoroethoxy)methyl)pyrimidin-4-amine (57 mg, 0.19 mmol), cesium carbonate (125 mg, 0.38 mmol), palladium (II) acetate (6.45 mg, 0.03 mmol) and 2-(dicyclohexylphosphino)biphenyl (10.07 mg, 0.03 mmol) in dioxane (1 mL) was heated at 120° C. by microwave irradiation under nitrogen atmosphere for 90 minutes. The mixture was filtered through diatomeous earth and the filter pad was washed with methanol. The eluate was concentrated in vacuum and purified by preparative chromatography yielding the title compound as a solid 45 mg (51%).

MS (APCI$^+$) m/z 465 (M+H)$^+$. $^1$H NMR (500 MHz, DMSO-d$_6$) ☒ 2.14 (s, 3H), 3.81 (s, 3H), 4.21 (q, 2H), 4.43-4.52 (m, 4H), 4.82 (t, 2H), 5.07 (br. s, 1H), 6.08 (br. s, 1H), 7.02 (s, 1H), 7.19 (d, 1H), 7.37 (d, 1H), 7.64 (d, 1H), 7.79 (s, 1H), 8.09 (br. s, 1H), 9.26 (s, 1H).

Example 36

1-(2-(3-Methoxy-4-(4-methyl-1H-imidazol-1-yl)phenylamino)-6-((2,2,2-trifluoroethoxy)-methyl)pyrimidin-4-ylamino)-2-methylpropan-2-ol

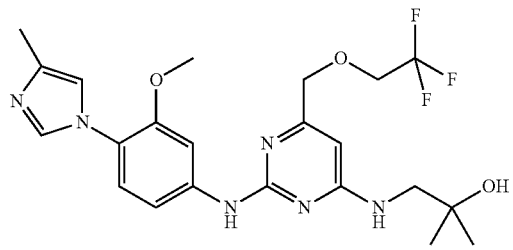 [SMILES: COc1cc(Nc2nc(COCC(F)(F)F)cc(NCC(C)(C)O)n2)ccc1-n1cnc(C)c1]

A mixture of 3-methoxy-4-(4-methyl-1H-imidazol-1-yl)aniline (45 mg, 0.22 mmol), 1-(2-chloro-6-((2,2,2-trifluoroethoxy)methyl)pyrimidin-4-ylamino)-2-methylpropan-2-ol (35 mg, 0.11 mmol), cesium carbonate (73 mg, 0.22 mmol), palladium(II) acetate (4 mg, 0.02 mmol) and 2-(dicyclohexylphosphino)biphenyl (6 mg, 0.02 mmol) in dioxane (1 mL) was heated at 120° C. by microwave irradiation under nitrogen atmosphere for 90 minutes. An additional equivalent of each: 3-methoxy-4-(4-methyl-1H-imidazol-1-yl)aniline, cesium carbonate, palladium(II) acetate and 2-(dicyclohexylphosphino)biphenyl was added and the reaction mixture was heated by microwave irradiation at 120° C. for additional 90 minutes. The mixture was filtered and purified by preparative HPLC to give the title compound as a solid 16 mg (29%).

MS (APCI$^+$) m/z 481 (M+H)$^+$. $^1$H NMR (500 MHz, ACETONITRILE-d$_3$) ☒ 1.18 (s, 6H), 2.18 (s, 3H), 3.42 (br. s, 2H), 3.83 (s, 3H), 4.06 (q, 2H), 4.46 (s, 2H), 6.07 (br. s, 1H), 6.15 (s, 1H), 6.92 (s, 1H), 7.12-7.21 (m, 2H), 7.54 (s, 1H), 7.67 (br. s, 1H), 7.85 (br. s, 1H).

Example 37

N2-(3-Methoxy-4-(4-methyl-1H-imidazol-1-yl)phenyl)-N4-(2-methoxyethyl)-6-((2,2,2-trifluoroethoxy)methyl)pyrimidine-2,4-diamine

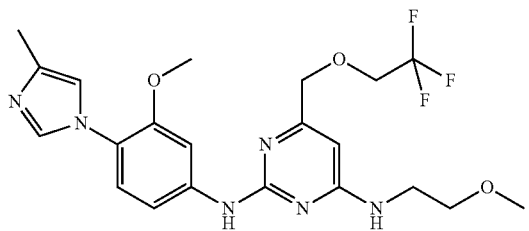 [SMILES: COCCNc1cc(COCC(F)(F)F)nc(Nc2ccc(-n3cnc(C)c3)c(OC)c2)n1]

2-Chloro-N-(2-methoxyethyl)-6-((2,2,2-trifluoroethoxy)methyl)pyrimidin-4-amine (43 mg, 0.14 mmol), 3-methoxy-4-(4-methyl-1H-imidazol-1-yl)aniline (58 mg, 0.29 mmol), cesium carbonate (94 mg, 0.29 mmol), palladium(II) acetate (5 mg, 0.02 mmol), 2-(dicyclohexylphosphino)-biphenyl (8 mg, 0.02 mmol) and dioxane (2 mL) were mixed in a vial and kept under an atmosphere of nitrogen. The mixture was heated in a microwave reactor at 120° C. for 90 min. The reaction mixture was filtered through at pad of diatomeous earth. The filter plug was rinsed with MeOH. The solvents were removed in vacuo and the residue was purified by preparative HPLC to give the title compound as a solid, 34 mg (51%).

MS (ES$^+$) m/z 467 (M+H)$^+$. $^1$H NMR (500 MHz, CHLOROFORM-d) δ ppm 2.34 (s, 3H) 3.41 (s, 3H) 3.56-3.68 (m, 4H) 3.86 (s, 3H) 3.97 (q, 2H) 4.53 (s, 2H) 5.22 (br. s, 1H) 6.09 (s, 1H) 6.89 (s, 1H) 7.01-7.19 (m, 3H) 7.65-7.79 (m, 2H).

Example 38

3-(2-(3-Methoxy-4-(4-methyl-1H-imidazol-1-yl)phenylamino)-6-((2,2,2-trifluoroethoxy)-methyl)pyrimidin-4-ylamino)propanenitrile

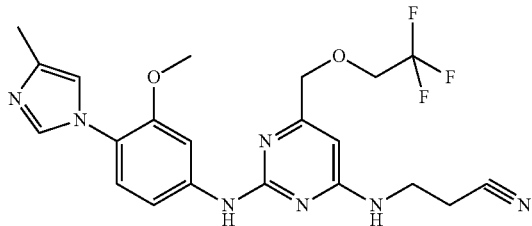 [SMILES: COc1cc(Nc2nc(COCC(F)(F)F)cc(NCCC#N)n2)ccc1-n1cnc(C)c1]

3-(2-Chloro-6-((2,2,2-trifluoroethoxy)methyl)pyrimidin-4-ylamino)propanenitrile (29 mg, 0.10 mmol), 3-methoxy-4-(4-methyl-1H-imidazol-1-yl)aniline (40 mg, 0.20 mmol), cesium carbonate (64 mg, 0.20 mmol), palladium(II) acetate (3 mg, 0.01 mmol), 2-(dicyclohexylphosphino)-biphenyl (5 mg, 0.01 mmol) and dioxane (1.5 mL) were mixed in a vial and kept under an atmosphere of nitrogen. The mixture was heated in a microwave reactor at 120° C. for 90 min. The mixture was filtered through at pad of diatomeous earth. The filter plug was rinsed with MeOH. The solvents were evaporated and the residue was purified by preparative HPLC to give the title compound as a solid, 22 mg (48%).

MS (ES$^+$) m/z 462 (M+H)$^+$. $^1$H NMR (500 MHz, CHLOROFORM-d) δ ppm 2.40 (br. s, 3H) 2.76 (t, 2H) 3.78 (q, 2H) 3.87 (s, 3H) 3.98 (q, 2H) 4.55 (s, 2H) 5.15 (br. s, 1H) 6.15 (s, 1H) 6.92 (s, 1H) 6.97-7.07 (m, 1H) 7.12-7.21 (m, 2H) 7.62 (br. s, 1H) 7.91 (br. s, 1H).

Example 39

4-((Benzylamino)methyl)-N-(3-methoxy-4-(6-methylpyridazin-4-yl)phenyl)-6-((2,2,2-trifluoroethoxy)methyl)pyrimidin-2-amine

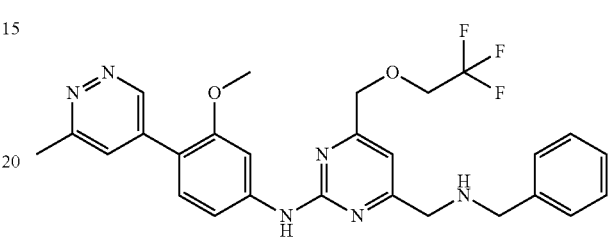

2-(3-Methoxy-4-(6-methylpyridazin-4-yl)phenylamino)-6-((2,2,2-trifluoroethoxy)methyl)-pyrimidine-4-carbaldehyde (100 mg, 0.23 mmol) was dissolved in DCE (4 mL), THF (1 mL) and DMF (0.1 mL). Benzylamine (0.030 mL, 0.28 mmol) and acetic acid (0.013 mL, 0.23 mmol) were added followed by sodium triacetoxyborohydride (69 mg, 0.32 mmol). The mixture was stirred at rt under nitrogen atmosphere for 1 hour. The reaction was quenched with water. The water phase was extracted by DCM (×2). The combined organic layer was dried over anhydrous sodium sulfate and evaporated onto silica. The silica was loaded on a pre-packed silica column. The column was eluted with a gradient of methanol in DCM to give the title compound as a solid, 58 mg (48%).

MS (ES$^+$) m/z 525 [M+H]$^+$. $^1$H NMR (500 MHz, CHLOROFORM-d) δ ppm 2.75 (s, 3H) 3.83 (s, 3H) 3.91 (s, 2H) 3.92-3.94 (s, 2H) 3.99 (q, 2H) 4.67 (s, 2H) 6.97 (s, 1H) 7.16 (dd, 1H) 7.28-7.34 (m, 2H) 7.34-7.38 (m, 2H) 7.38-7.41 (m, 3H) 7.49 (d, 1H) 7.73 (d, 1H) 9.27 (d, 1H).

Example 40

4-((3-Fluoroazetidin-1-yl)methyl)-N-(3-methoxy-4-(4-methyl-1H-imidazol-1-yl)phenyl)-6-((2,2,2-trifluoroethoxy)methyl)pyrimidin-2-amine

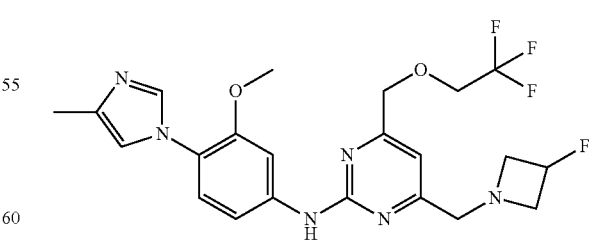

3-Fluoroazetidine hydrochloride (25 mg, 0.23 mmol) was mixed with methanol (5 mL). Sodium methoxide (30 w % in methanol, 0.042 mL, 0.23 mmol) was added followed by 2-(3-methoxy-4-(4-methyl-1H-imidazol-1-yl)phenylamino)-6-((2,2,2-trifluoroethoxy)methyl)pyrimidine-4- carbaldehyde (80 mg, 0.19 mmol). The mixture was stirred for 2 min. Acetic acid (0.035 mL, 0.61 mmol) was added and the mixture was stirred for 5 min. Sodium cyanoborohydride (17 mg, 0.27 mmol) was added and the mixture was stirred at rt under nitrogen atmosphere for 1 h. Water was added and the mixture was stirred for 5 min. The solvents were evaporated and the residue was purified by preparative HPLC to give the title compound as a dry film 44 mg (48%).

MS (ES$^+$) m/z 480 [M+H]$^+$. $^1$H NMR (500 MHz, CHLOROFORM-d) δ ppm 2.30 (s, 3H) 3.28-3.33 (m, 1H) 3.33-3.38 (m, 1H) 3.73 (s, 2H) 3.77-3.85 (m, 2H) 3.86 (s, 3H) 3.99 (q, 2H) 4.66 (s, 2H) 5.11-5.29 (m, 1H) 6.88 (s, 1H) 6.94 (s, 1H) 7.08 (dd, 1H) 7.17 (d, 1H) 7.34 (s, 1H) 7.64 (s, 1H) 7.71 (d, 1H).

Example 41

4-((Dimethylamino)methyl)-N-(3-methoxy-4-(4-methyl-1H-imidazol-1-yl)phenyl)-6-((2,2,2-trifluoroethoxy)methyl)pyrimidin-2-amine

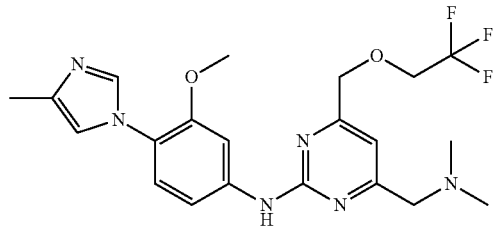

2-(3-Methoxy-4-(4-methyl-1H-imidazol-1-yl)phenylamino)-6-((2,2,2-trifluoroethoxy)methyl)-pyrimidine-4-carbaldehyde (100 mg, 0.24 mmol) was dissolved in DCE (4 mL). Dimethylamine (2 M in THF, 0.142 mL, 0.28 mmol) and acetic acid (0.014 mL, 0.24 mmol) were added followed by sodium triacetoxyborohydride (80 mg, 0.38 mmol). The mixture was stirred at rt under nitrogen atmosphere for 1 hour 45 min. Water was added and the mixture was stirred for 3 minutes then the phases were separated. The water phase was extracted by DCM. The combined organic layer was dried over anhydrous sodium sulfate, filtered and concentrated on silica then subjected to column chromatography eluting with a gradient of methanol in DCM. The solvents were evaporated and the residue was purified by preparative HPLC to give the title compound as a dry film, 22 mg (21%).

MS (ES$^-$) m/z 449 [M−H]$^-$. $^1$H NMR (400 MHz, CHLOROFORM-d) δ ppm 2.30 (d, 3H) 2.31-2.36 (m, 6H) 3.49 (s, 2H) 3.86 (s, 3H) 3.99 (q, 2H) 4.68 (s, 2H) 6.87 (s, 1H) 7.02 (s, 1H) 7.04 (dd, 1H) 7.16 (d, 1H) 7.41 (s, 1H) 7.63 (d, 1H) 7.79 (d, 1H).

Example 42

4-((3-Fluoroazetidin-1-yl)methyl)-N-(3-methoxy-4-(6-methylpyridazin-4-yl)phenyl)-6-((2,2,2-trifluoroethoxy)methyl)pyrimidin-2-amine

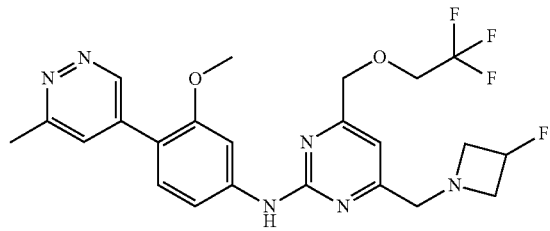 [SMILES: COc1cc(Nc2nc(COCC(F)(F)F)cc(CN3CC(F)C3)n2)ccc1-c1cnnc(C)c1]

3-Fluoroazetidine hydrochloride (31 mg, 0.28 mmol) was mixed with methanol (5 mL). Sodium methoxide (0.051 mL, 0.28 mmol) was added followed by 2-(3-methoxy-4-(6-methylpyridazin-4-yl)phenylamino)-6-((2,2,2-trifluoroethoxy)methyl)pyrimidine-4-carbaldehyde (100 mg, 0.23 mmol). The mixture was stirred for 2 min. Acetic acid (0.042 mL, 0.74 mmol) was added. The mixture was stirred for 5 min. Sodium cyanoborohydride (20 mg, 0.32 mmol) was added and the mixture was stirred at rt under nitrogen atmosphere for 1 h. Water was added and the mixture was stirred for 5 min. The solvents were evaporated and the residue was purified by preparative HPLC to give the title compound as a solid, 48 mg (42%).

MS (ES$^+$) m/z 493 [M+H]$^+$. $^1$H NMR (500 MHz, CHLOROFORM-d) δ ppm 2.76 (s, 3H) 3.32-3.46 (m, 2H) 3.79 (s, 2H) 3.85-3.90 (m, 2H) 3.91 (s, 3H) 4.01 (q, 2H) 4.69 (s, 2H) 5.12-5.33 (m, 1H) 6.97 (s, 1H) 7.18 (dd, 1H) 7.34 (d, 2H) 7.51 (d, 1H) 7.73 (s, 1H) 9.28 (d, 1H).

Example 43

4-(1-(3-Fluoroazetidin-1-yl)ethyl)-N-(3-methoxy-4-(4-methyl-1H-imidazol-1-yl)phenyl)-6-((2,2,2-trifluoroethoxy)methyl)pyrimidin-2-amine

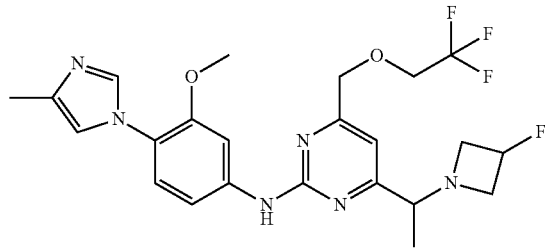 [SMILES: COc1cc(Nc2nc(COCC(F)(F)F)cc(C(C)N3CC(F)C3)n2)ccc1-n1cnc(C)c1]

3-Fluoroazetidine hydrochloride (28 mg, 0.25 mmol) was mixed with methanol (5 mL). Sodium methoxide (0.046 mL, 0.25 mmol) was added followed by 1-(2-(3-methoxy-4-(4-methyl-1H-imidazol-1-yl)phenylamino)-6-((2,2,2-trifluoroethoxy)methyl)pyrimidin-4-yl)ethanone (90 mg, 0.21 mmol). The mixture was stirred for 2 min. Acetic acid (0.044 mL, 0.76 mmol) was added. The mixture was stirred for 5 min. Sodium cyanoborohydride (18 mg, 0.29 mmol) was added and the mixture was stirred at rt under nitrogen atmosphere for 16 hours. Water was added and the mixture was stirred for 5 min then diluted with DCM and sodium bicarbonate (sat, aq). The phases were separated and the aqueous layer was extracted with DCM. The combined organic layer was dried over anhydrous sodium sulfate and concentrated. The residue was purified by column chromatography on silica eluting with a gradient of MeOH and DCM. The residue was purified by preparative HPLC to give the title compound as a dry film, 33 mg (32%).

MS (ES$^+$) m/z 495 [M+H]$^+$. $^1$H NMR (400 MHz, CHLOROFORM-d) δ ppm 1.29 (d, 3H) 2.30 (d, 3H) 3.08-3.20 (m, 1H) 3.20-3.32 (m, 1H) 3.41 (q, 1H) 3.56-3.67 (m, 1H) 3.72-3.83 (m, 1H) 3.86 (s, 3H) 3.99 (q, 2H) 4.67 (s, 2H) 5.05-5.27 (m, 1H) 6.87 (s, 1H) 6.94 (s, 1H) 7.05 (dd, 1H) 7.16 (d, 1H) 7.40 (s, 1H) 7.64 (d, 1H) 7.77 (d, 1H).

Example 44

1-(2-(3-Methoxy-4-(4-methyl-1H-imidazol-1-yl)phenylamino)-6-((2,2,2-trifluoroethoxy)-methyl)pyrimidin-4-yl)ethanol

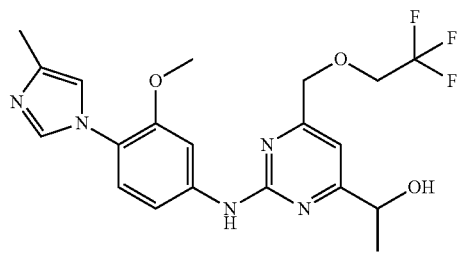

1-(2-(3-Methoxy-4-(4-methyl-1H-imidazol-1-yl)phenylamino)-6-((2,2,2-trifluoroethoxy)-methyl)pyrimidin-4-yl)ethanone (55 mg, 0.13 mmol) was dissolved in ethanol (5 mL). Sodium borohydride (24 mg, 0.63 mmol) was added and the mixture was stirred at rt for 10 min. Acetone (2 mL) was added and the mixture was stirred for 20 min. The solvent were evaporated. The residue was purified by column chromatography on silica eluting with a gradient of methanol in DCM to give the title compound as a solid, 40 mg (72%).

MS (ES+) m/z 438 [M+H]+. $^1$H NMR (500 MHz, CHLOROFORM-d) δ ppm: 1.54 (d, 1H) 2.29 (d, 3H) 3.85 (s, 3H) 4.00 (q, 2H) 4.68 (s, 2H) 4.81 (q, 1H) 5.86 (bs, 1H) 6.87 (t, 1H) 7.00 (s, 1H) 7.08 (dd, 1H) 7.17 (d, 1H) 7.67 (d, 1H) 7.69 (d, 1H) 7.71 (s, 1H).

Example 45

2-(2-(3-Methoxy-4-(4-methyl-1H-imidazol-1-yl)phenylamino)-6-((2,2,2-trifluoroethoxy)-methyl)pyrimidin-4-yl)butan-2-ol

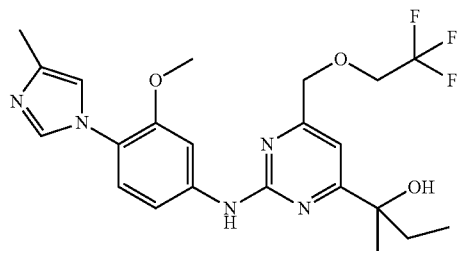 [SMILES: CCC(C)(O)c1cc(COCC(F)(F)F)nc(Nc2ccc(-n3cnc(C)c3)c(OC)c2)n1]

Ethylmagnesium bromide (0.86 mL, 2.57 mmol, 3M in THF) was dissolved in THF (5 mL). 1-(2-(3-Methoxy-4-(4-methyl-1H-imidazol-1-yl)phenylamino)-6-((2,2,2-trifluoroethoxy)methyl)-pyrimidin-4-yl)ethanone (140 mg, 0.32 mmol) was dissolved in THF (5 mL) and was added slowly to the solution of ethylmagnesium bromide. The mixture was cooled on ice, ammonium chloride (sat, aq, 5 mL) was added and the mixture was stirred for 5 min. The mixture was extracted with EtOAc (×2). The solvents were evaporated and the residue was purified by column chromatography on silica eluting with a gradient of MeOH in DCM to give the title compound as an oil, 63 mg (42%).

MS (APCI+) m/z 466 (M+H)+. $^1$H NMR (400 MHz, CHLOROFORM-d) δ ppm 0.82 (t, 3H) 1.52 (s, 3H) 1.86 (q, 2H) 2.30 (d, 3H) 3.87 (s, 3H) 4.00 (q, 2H) 4.40 (br. s, 1H) 4.70 (s, 2H) 6.89 (t, 1H) 6.98 (s, 1H) 7.08 (dd, 1H) 7.19 (d, 1H) 7.57 (s, 1H) 7.65 (d, 1H) 7.68 (d, 1H).

Example 46

2-(2-(3-Methoxy-4-(2-methyloxazol-5-yl)phenylamino)-6-((2,2,2-trifluoroethoxy)methyl)-pyrimidin-4-yl)propan-2-ol

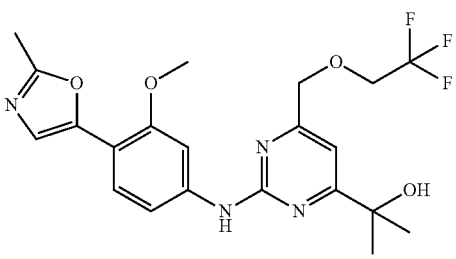 [SMILES: COc1cc(Nc2nc(COCC(F)(F)F)cc(C(C)(C)O)n2)ccc1-c1cnc(C)o1]

1-(2-(3-Methoxy-4-(2-methyloxazol-5-yl)phenylamino)-6-((2,2,2-trifluoroethoxy)methyl)-pyrimidin-4-yl)ethanone (64 mg, 0.15 mmol) was dissolved in THF (5 mL) and was added slowly to a solution of methylmagnesium bromide (3 M in THF, 0.391 mL, 1.17 mmol) in THF (5 mL). The mixture was stirred for 5 min. The mixture was cooled on ice bath and ammonium chloride (sat, aq, 5 mL) was added. The mixture was stirred for 5 min. The mixture was extracted with EtOAc (×2). The solvents were evaporated and the residue was purified by column chromatography eluting with a gradient of methanol in DCM to give the title compound as a solid, 46 mg (69%).

MS (APCI+) m/z 453 (M+H)+. $^1$H NMR (400 MHz, CHLOROFORM-d) δ ppm 1.56 (s, 6H) 2.52 (s, 3H) 3.97 (s, 3H) 4.00 (q, 2H) 4.23 (bs, 1H) 4.69 (s, 2H) 7.01 (s, 1H) 7.06 (dd, 1H) 7.33 (s, 1H) 7.43 (bs, 1H) 7.65 (d, 1H) 7.67 (d, 1H).

Example 47

2-(2-(3-Methoxy-4-(6-methylpyridazin-4-yl)phenylamino)-6-((2,2,2-trifluoroethoxy)-methyl)pyrimidin-4-yl)propan-2-ol

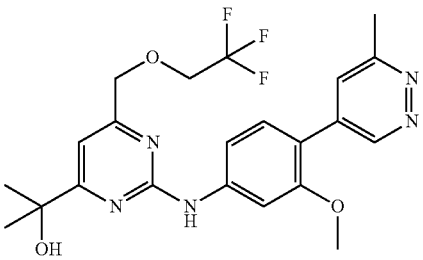 [SMILES: COc1cc(Nc2nc(COCC(F)(F)F)cc(C(C)(C)O)n2)ccc1-c1cnnc(C)c1]

1-(2-(3-Methoxy-4-(6-methylpyridazin-4-yl)phenylamino)-6-((2,2,2-trifluoroethoxy)methyl)-pyrimidin-4-yl)ethanone (60 mg, 0.13 mmol) was dissolved in THF (5 mL) and was added slowly to a solution of methylmagnesium bromide (3 M in THF, 0.358 mL, 1.07 mmol) in THF (5 mL). The mixture was stirred for 5 min. The mixture was cooled on an ice bath and ammonium chloride (sat, aq, 5 mL) was added. The mixture was stirred for 5 min. The mixture was extracted with EtOAc (×2). The solvents were evaporated and the residue was purified by column chromatography on silica eluting with a gradient of MeOH in DCM to give the title compound as a solid, 42 mg (68%).

MS (APCI$^+$) m/z 464 (M+H)$^+$. $^1$H NMR (400 MHz, CHLOROFORM-d) δ ppm 1.57 (s, 6H) 2.76 (s, 3H) 3.91 (s, 3H) 4.02 (q, 2H) 4.13 (bs, 1H) 4.71 (s, 2H) 7.06 (s, 1H) 7.17 (dd, 1H) 7.36 (d, 1H) 7.49 (bs, 1H) 7.52 (d, 1H) 7.71 (d, 1H) 9.28 (d, 1H).

Example 48

2-(2-(3-Methoxy-4-(2-methyloxazol-5-yl)phenylamino)-6-((2,2,2-trifluoroethoxy)methyl)-pyrimidin-4-yl)-3-methylbutan-2-ol

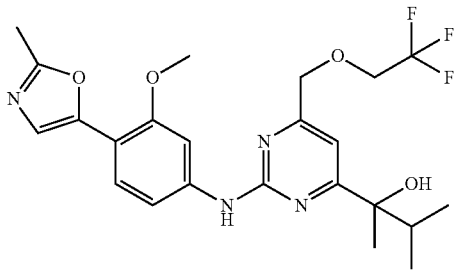 [SMILES: COc1cc(Nc2nc(COCC(F)(F)F)cc(C(C)(O)C(C)C)n2)ccc1-c1cnc(C)o1]

1-(2-(3-Methoxy-4-(2-methyloxazol-5-yl)phenylamino)-6-((2,2,2-trifluoroethoxy)methyl)-pyrimidin-4-yl)ethanone (60 mg, 0.14 mmol) was dissolved in THF (5 mL) and was added slowly to a solution of isopropyl magnesium chloride (2 M in THF, 0.206 mL, 0.41 mmol) in THF (5 mL). The mixture was stirred for 5 min. The mixture was cooled on an ice bath, ammonium chloride (sat, aq, 5 mL) was added. The mixture was stirred for 5 min. The mixture was extracted with EtOAc (×2). The solvents were evaporated and the residue was purified by column chromatography on silica eluting with a gradient of MeOH in DCM to give the title compound as a solid, 40 mg (61%).

MS (APCI$^+$) m/z 481 (M+H)$^+$. $^1$H NMR (500 MHz, CHLOROFORM-d) δ ppm 0.74 (d, 3H) 1.04 (d, 3H) 1.49 (s, 3H) 1.84 (br. s, 1H) 2.03 (m, 1H) 2.52 (s, 3H) 3.98 (s, 3H) 4.00 (q, 2H) 4.25 (br. s, 1H) 4.69 (s, 2H) 6.93 (s, 1H) 7.07 (dd, 1H) 7.33 (s, 1H) 7.37 (s, 1H) 7.63 (d, 1H) 7.67 (d, 1H).

Example 49

(2-(3-Methoxy-4-(4-methyl-1H-imidazol-1-yl)phenylamino)-6-((2,2,2-trifluoroethoxy)-methyl)pyrimidin-4-yl)(phenyl)methanol

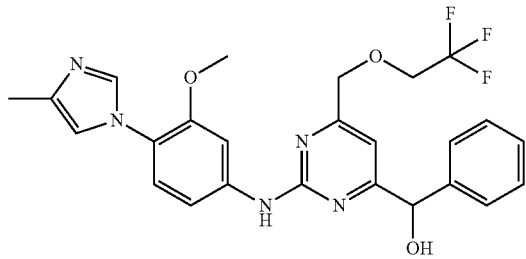 [SMILES: COc1cc(Nc2nc(COCC(F)(F)F)cc(C(O)c3ccccc3)n2)ccc1-n1cnc(C)c1]

2-(3-Methoxy-4-(4-methyl-1H-imidazol-1-yl)phenylamino)-6-((2,2,2-trifluoroethoxy)methyl)-pyrimidine-4-carbaldehyde (0.10 g, 0.24 mmol) was dissolved in THF (5 mL). The mixture was cooled on an ice bath and phenylmagnesium bromide (3 M, 0.79 mL, 2.37 mmol) was added over 30 min. MeOH and ammonium chloride (aq, sat) were added. The mixture was extracted with EtOAc (×2). The organic phase was filtered through a pad of silica and sodium sulfate. The solvents were evaporated and the residue was purified by preparative HPLC to give the title compound as a dry film, 50 mg (22%).

MS (APCI$^+$) m/z 500 (M+H)$^+$. $^1$H NMR (500 MHz, CHLOROFORM-d) δ ppm 2.29 (s, 3H) 3.81 (s, 3H) 3.94 (q, 2H) 4.64 (d, 2H) 4.84 (bs, 1H) 5.69 (s, 1H) 6.88 (s, 1H) 6.92 (s, 1H) 7.06 (dd, 1H) 7.17 (d, 1H) 7.30-7.41 (m, 3H) 7.41-7.50 (m, 3H) 7.61 (s, 1H) 7.62 (d, 1H).

Example 50

2-(6-((1,3-Difluoropropan-2-yloxy)methyl)-2-(3-methoxy-4-(4-methyl-1H-imidazol-1-yl)phenylamino)pyrimidin-4-yl)propan-2-ol

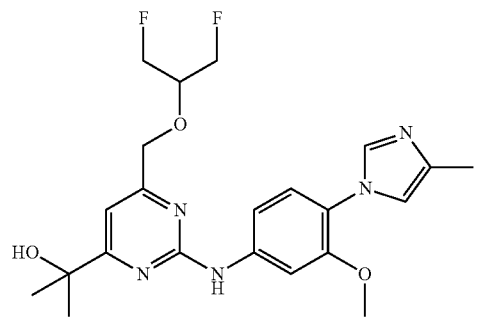 [SMILES: COc1cc(Nc2nc(COC(CF)CF)cc(C(C)(C)O)n2)ccc1-n1cnc(C)c1]

To an ice-cold solution of methylmagnesium bromide (0.71 mL, 1.0 mmol) in THF (6 mL) was added over 5 min a solution of 1-(6-((1,3-difluoropropan-2-yloxy)methyl)-2-(3-methoxy-4-(4-methyl-1H-imidazol-1-yl)phenylamino)pyrimidin-4-yl)ethanone (43 mg, 0.1 mmol) of in THF (3 mL). The reaction was stirred at 0° C. for 30 minutes. Ammonium chloride (sat, aq) was added. The solvent volume was reduced by evaporation. DCM was added and the phases were separated. The organic phase was concentrated and the residue was purified by preparative HPLC to give the title compound as a dry film (34 mg, 76%).

MS (APCI$^+$) m/z 448 (M+H)$^+$. $^1$H NMR (400 MHz, CHLOROFORM-d) δ ppm 1.56 (s, 6H) 2.31 (d, 3H) 3.87 (s, 3H) 3.91-4.07 (m, 1H) 4.20 (br. s, 1H) 4.54-4.60 (m, 2H) 4.66-4.70 (m, 2H) 4.73 (s, 2H) 6.87-6.91 (m, 1H) 7.07 (dd, 1H) 7.10 (s, 1H) 7.19 (d, 1H) 7.32 (s, 1H) 7.66 (dd, 2H).

Example 51

4-(Cyclopropylmethoxy)-N-[3-methoxy-4-(4-methyl-1H-imidazol-1-yl)phenyl]-6-[(2,2,2-trifluoroethoxy)methyl]pyrimidin-2-amine

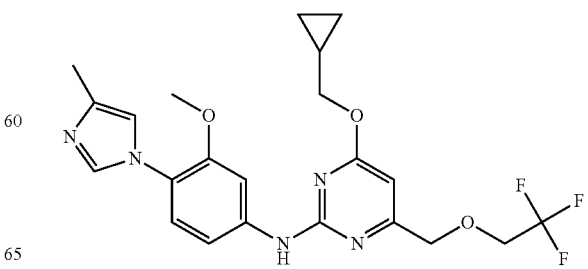

2-Chloro-4-(cyclopropylmethoxy)-6-[(2,2,2-trifluoroethoxy)methyl]pyrimidine (55 mg, 0.19 mmol), 3-methoxy-4-(4-methyl-1H-imidazol-1-yl)aniline (45 mg, 0.22 mmol, cesium carbonate (124 mg, 0.38 mmol) and 2-(dicyclohexylphosphino)biphenyl (10 mg, 0.029 mmol) were added to dioxane (3 mL) in a microwave tube. Palladium (II) acetate (6.4 mg, 0.029 mmol) was added. The tube was vacuum-backfilled with nitrogen and sealed. The mixture was heated in a microwave reactor at 100° C. for 2 hours and then diluted with ethylacetate, washed with water, brine, dried over $Mg_2SO_4$ and the solvent was removed under reduced pressure. The residue was purified by chromatography on silica gel, eluting with mixtures of 0% to 5% methanol in ethyl acetate. The product was further purified by chromatography on a reverse phase column, eluting with mixtures of 0% to 100% methanol in water containing 5% trifluoroacetic acid to afford the title compound as a solid, 40 mg (45%). MS (ESI$^+$) m/z 464 [M+H]$^+$. $^1$H NMR (300 MHz, CDCl$_3$) δ ppm 0.34-0.37 (m, 2H), 0.64-0.70 (m, 2H), 1.20-1.40 (m, 1H), 2.30 (s, 3H), 3.86 (s, 3H), 3.97 (q, 2H), 4.20 (d, 2H), 4.59 (s, 2H), 6.41 (s, 1H), 6.87 (s, 1H), 7.00 (d, 1H), 7.08 (s, 1H), 7.16 (d, 1H), 7.64 (s, 1H), 7.74 (s, 1H).

Example 52

2-(6-(1-Ethoxy-2,2-difluorocyclopropyl)-2-(3-methoxy-4-(4-methyl-1H-imidazol-1-yl)phenylamino)pyrimidin-4-yl)propan-2-ol

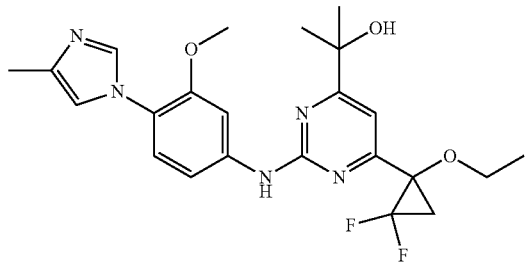 [SMILES: CCOC1(c2cc(C(C)(C)O)nc(Nc3ccc(-n4cnc(C)c4)c(OC)c3)n2)CC1(F)F]

A mixture of 2-(2-chloro-6-(1-ethoxy-2,2-difluorocyclopropyl)pyrimidin-4-yl)propan-2-ol (8 mg, 0.03 mmol), 3-methoxy-4-(4-methyl-1H-imidazol-1-yl)aniline (6 mg, 0.03 mmol), cesium carbonate (17.81 mg, 0.05 mmol), palladium acetate (1 mg, 4 µmol) and 2-(dicyclohexylphosphino)biphenyl (1.5 mg, 4 µmol) in dioxane (1.5 mL) was heated under argon atmosphere at 120° C. for 90 minutes in microwave reactor. The crude mixture was filtered through a short silica plug which was washed with 10% MeOH in EtOAc (35 mL). The residue was purified by preparative HPLC to give the title compound as a dry film, 6 mg (48%).

MS (APCI$^+$) m/z 460 [M+H]$^+$. $^1$H NMR (400 MHz, CHLOROFORM-d) δ ppm 1.32 (t, 3H) 1.57 (s, 6H) 1.80-1.91 (m, 1H) 2.31 (s, 3H) 2.64-2.74 (m, 1H) 3.57 (q, 2H) 3.87 (s, 3H) 6.90 (br. s, 1H) 6.95 (dd, 1H) 7.19 (d, 1H) 7.25 (s, 1H) 7.29 (s, 1H) 7.63 (d, 1H) 7.67 (br. s, 1H).

BIOLOGICAL ASSAYS

The level of activity of the compounds on AP formation was tested using the following methods:
HEK Assay
Compounds were diluted in 100% DMSO and stored at 20° C. prior to use. Human Embryonic Kidney (HEK) cell line stably expressing APP with the Swedish mutation (APPswe) was cultured using Dulbecco's Modified Eagles medium (DMEM) supplied with 4500 g/L glucose, Na-pyruvate and GlutaMAX, 10% Foetal bovine serum, 100 U/mL penicillin-streptomycin (PEST), 1× non-essential amino acids (NEAA), 10 µM Hepes, 100 µg/mL Zeocine. Cells at about 80% confluence were washed with PBS, detached from culture flasks using 1× Trypsin/EDTA diluted in PBS, re-suspended in cell media and plated in 384-well poly-d-lysine coated cell culture plates at about 10000-15000 cells/well, in 25 µL cell media. Optionally, cryo-preserved cells (frozen and stored at −140° C. in 90% cell media and 10% DMSO) were thawed, washed and plated as above. Next the cells were incubated for 15-24 h at 37° C. and 5% $CO_2$, after which cell medium was changed. Fresh medium containing test compound diluted ×200 from prepared compound plate was added to the cells before further incubation for 4-6 hours at 37° C. and 5% $CO_2$. After incubation with test compound the amount of Aβ peptides, including Aβ42, Aβ40, Aβ39, Aβ38 and Aβ37, secreted to cell medium was analyzed using the electrochemiluminescence assay technology from Meso Scale Discovery Technology, in combination with specific antibodies raised against the different Aβ peptides. Potential cytotoxic effects of the compounds were assayed by measuring the ATP content (ViaLight) from cell lysate.
PCN Assay
Compounds were diluted in 100% DMSO and stored at 20° C. prior to use. Primary cortical neuronal cells (PCN) were isolated from 16-day mouse embryos and cultured in Ham's F12 media containing 10% Foetal bovine serum, 10 mM Hepes, 2 mM L-glutamine and 100 U/mL Penicillin-Streptomycin. 150000-250000 cells/well, in 200 µL cell media were seeded onto 96-well poly-D-Lysine coated plates. After incubation at 37° C., 5% $CO_2$ for five days, the media was exchanged for fresh medium containing test compound diluted ×100, before further incubation for 16-20 hours at 37° C. and 5% $CO_2$. After incubation with test compound the amount of 442 peptides secreted to cell medium was analyzed using the solid phase sandwich Enzyme-Linked-Immuno-Sorbent Assay (ELISA)-kit from Invitrogen for detection of mouse βAmyloid 1-42. Potential cytotoxic effects of the compounds were assayed by measuring the ATP content (Via Light) from cell lysate.
Results
Biological data on exemplified compounds are given below in Table 1.

TABLE 1

| pIC$_{50}$ values in the HEK and PCN assays for the examples of the present invention. | | |
|---|---|---|
| Example number | pIC50 Aβ42 HEK assay | pIC50 Aβ42 PCN assay |
| 1 | 7.7 | 7.3 |
| 2 | 7.5 | 7.2 |
| 3 | 7.6 | 7.4 |
| 4 | 7.6 | 8.0 |
| 5 | 7.7 | 7.7 |
| 6 | 7.5 | 7.5 |
| 7 | 7.5 | 7.5 |
| 8 | 7.5 | 7.7 |
| 9 | 7.6 | 7.5 |
| 10 | 7.2 | 7.5 |
| 11 | 7.6 | 7.3 |
| 12 | 7.1 | 7.4 |
| 13 | 7.7 | 7.3 |
| 14 | ND | 7.4 |

TABLE 1-continued pIC$_{50}$ values in the HEK and PCN assays for the examples of the present invention.

| Example number | pIC50 Aβ42 HEK assay | pIC50 Aβ42 PCN assay |
|---|---|---|
| 15 | 7.5 | 7.3 |
| 16 | 7.3 | 7.1 |
| 17 | 6.7 | 6.7 |
| 18 | 7.2 | 7.0 |
| 19 | 6.7 | ND |
| 20 | 7.4 | 7.0 |
| 21 | 6.9 | 7.3 |
| 22 | 7.1 | 7.2 |
| 23 | 7.1 | 7.1 |
| 24 | 7.0 | 7.1 |
| 25 | 7.6 | 7.3 |
| 26 | 7.3 | 7.7 |
| 27 | 6.8 | 6.9 |
| 28 | 7.4 | 7.0 |
| 29 | 7.4 | 7.2 |
| 30 | 7.4 | 7.2 |
| 31 | 6.6 | 6.5 |
| 32 | 7.0 | 6.5 |
| 33 | 7.4 | 7.3 |
| 34 | 7.3 | 7.0 |
| 35 | 7.3 | 7.6 |
| 36 | 7.2 | 7.4 |
| 37 | 7.4 | 7.2 |
| 38 | 7.3 | 7.4 |
| 39 | 6.9 | 6.7 |
| 40 | 6.9 | 7.0 |
| 41 | 6.8 | ND |
| 42 | 7.1 | 6.6 |
| 43 | 7.5 | 6.8 |
| 44 | 7.3 | 7.0 |
| 45 | 7.3 | 7.2 |
| 46 | 7.4 | 7.1 |
| 47 | 7.3 | 7.0 |
| 48 | 7.6 | 7.3 |
| 49 | 7.1 | 7.1 |
| 50 | 7.1 | 7.2 |
| 51 | 7.2 | 6.9 |
| 52 | 6.7 | 6.7 |

ND = not determined

The pIC50 of the new compounds is improved compared to known compounds, such as for example compound 105 from WO2009103652, which has a pIC50 of 6.35-6.36.

The invention claimed is:

1. A compound, or a pharmaceutically acceptable salt thereof, having formula (Ia)

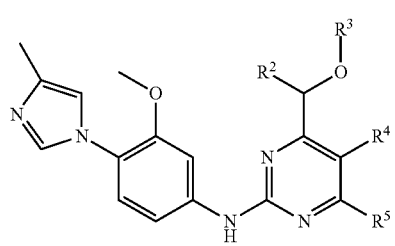

(Ia)

wherein:
$R^2$ is hydrogen or $C_{1-3}$-alkyl;
$R^3$ is fluoro-$C_{1-3}$-alkyl or $C_{3-6}$-cycloalkyl-$C_{1-3}$-alkyl, wherein $C_{3-6}$-cycloalkyl is optionally substituted with one or more fluoro substituents;
$R^4$ is hydrogen or $C_{1-3}$-alkyl;
$R^5$ is —$NR^{6A}R^{6B}$, —$OR^7$, —$CH_2OR^7$, —$C(R^{8A})(R^{8B})$OH, —$C(R^{9A})(R^{9B})$—$NR^{6A}R^{6B}$, or cyano-$C_{1-6}$-alkyl;

$R^{6A}$ is hydrogen, $C_{1-6}$-alkyl, fluoro-$C_{1-6}$-alkyl, hydroxy-$C_{1-6}$-alkyl; $C_{1-6}$-alkoxy-$C_{1-6}$-alkyl, cyano-$C_{1-6}$-alkyl, $C_{3-7}$-cycloalkyl, $C_{3-7}$-cycloalkyl-$C_{1-6}$-alkyl, heterocyclyl, heterocyclyl-$C_{1-6}$-alkyl, phenyl, or phenyl-$C_{1-6}$-alkyl;
or when $R^5$ is —$NR^{6A}R^{6B}$, $R^{6A}$ together with $R^4$ is —$CH_2$—, —$CH_2$—$CH_2$— or —$CH_2$—$CH_2$—$CH_2$—, thereby forming a 4- to 6-membered ring containing one nitrogen atom;
$R^{6B}$ is hydrogen or $C_{1-6}$-alkyl;
or $R^{6A}$ and $R^{6B}$, together with the nitrogen atom to which they are attached, form a 4- to 6-membered saturated heterocyclic ring, which is optionally substituted with one or more substituents independently selected from the group consisting of fluoro and $C_{1-3}$-alkyl;
$R^7$ is $C_{1-6}$-alkyl, fluoro-$C_{1-6}$-alkyl or $C_{3-7}$-cycloalkyl-$C_{1-6}$-alkyl;
or when $R^5$ is $OR^7$, $R^7$ together with $R^4$ is —$CH_2$—, —$CH_2$—$CH_2$— or —$CH_2$—$CH_2$—$CH_2$—, thereby forming a 4- to 6-membered ring containing one oxygen atom;
$R^{8A}$ is hydrogen, $C_{1-6}$-alkyl, fluoro-$C_{1-6}$-alkyl, $C_{3-7}$-cycloalkyl, $C_{3-7}$-cycloalkyl-$C_{1-6}$-alkyl, phenyl or phenyl-$C_{1-6}$-alkyl; and
$R^{8B}$, $R^{9A}$ and $R^{9B}$ are each independently selected from the group consisting of hydrogen and $C_{1-3}$-alkyl.

2. The compound according to claim 1, or a pharmaceutically acceptable salt thereof, wherein $R^2$ is hydrogen or methyl.

3. The compound according to claim 1, or a pharmaceutically acceptable salt thereof, wherein $R^3$ is 2,2,2-trifluoroethyl or cyclopropylmethyl.

4. The compound according to claim 1, or a pharmaceutically acceptable salt thereof, wherein $R^4$ is hydrogen or methyl.

5. The compound according to claim 1, or a pharmaceutically acceptable salt thereof, wherein $R^5$ is —$NR^{6A}R^{6B}$ wherein $R^{6A}$ is methyl or 2-propyl and $R^{6B}$ is hydrogen, or wherein $R^{6A}$ and $R^{6B}$, together with the nitrogen atom to which they are attached, form an azetidine ring; or
$R^5$ is —$OR^7$ wherein $R^7$ is methyl; or
$R^5$ is —$C(R^{8A})(R^{8B})$OH wherein $R^{8A}$ is hydrogen, methyl, trifluoromethyl or cyclopropylmethyl and $R^{8B}$ is hydrogen or methyl; or
$R^5$ is cyanomethyl.

6. The compound according to claim 1, selected from the group consisting of:
4-(Azetidin-1-yl)-6-((cyclopropylmethoxy)methyl)-N-(3-methoxy-4-(4-methyl-1H-imidazol-1-yl)phenyl)pyrimidin-2-amine;
N$^4$-Methyl-N$^2$-(4-(4-methyl-1H-imidazol-1-yl)phenyl)-6-((2,2,2-trifluoroethoxy)methyl)-pyrimidine-2,4-diamine;
2-[2-[3-Methoxy-4-(4-methylimidazol-1-yl)anilino]-6-(2,2,2-trifluoroethoxymethyl)-pyrimidin-4-yl]acetonitrile;
N$^2$-(3-Methoxy-4-(4-methyl-1H-imidazol-1-yl)phenyl)-N$^4$,5-dimethyl-6-((2,2,2-trifluoroethoxy)methyl)pyrimidine-2,4-diamine;
2-(2-(3-Methoxy-4-(4-methyl-1H-imidazol-1-yl)phenylamino)-5-methyl-6-((2,2,2-trifluoroethoxy)methyl) pyrimidin-4-yl)propan-2-ol;
1-(2-(3-Methoxy-4-(4-methyl-1H-imidazol-1-yl)phenylamino)-5-methyl-6-((2,2,2-trifluoroethoxy)methyl) pyrimidin-4-yl)ethanol;

1-(2-(3-Methoxy-4-(4-methyl-1H-imidazol-1-yl)phenylamino)-6-(1-(2,2,2-trifluoroethoxy)-ethyl)pyrimidin-4-yl)ethanol;

$N^4$-Isopropyl-$N^2$-(3-methoxy-4-(4-methyl-1H-imidazol-1-yl)phenyl)-6-((2,2,2-trifluoroethoxy)methyl)pyrimidine-2,4-diamine;

$N^2$-(3-Methoxy-4-(4-methyl-1H-imidazol-1-yl)phenyl)-N4-methyl-6-((2,2,2-trifluoroethoxy)methyl)pyrimidine-2,4-diamine;

(2-(3-Methoxy-4-(4-methyl-1H-imidazol-1-yl)phenylamino)-6-((2,2,2-trifluoroethoxy)methyl)pyrimidin-4-yl)methanol;

2-(2-(3-Methoxy-4-(4-methyl-1H-imidazol-1-yl)phenylamino)-6-(1-(2,2,2-trifluoroethoxy)ethyl)pyrimidin-4-yl)propan-2-ol;

2,2,2-Trifluoro-1-(2-(3-methoxy-4-(4-methyl-1H-imidazol-1-yl)phenylamino)-6-((2,2,2-trifluoroethoxy)methyl)pyrimidin-4-yl)ethanol;

2-Cyclopropyl-1-(2-(3-methoxy-4-(4-methyl-1H-imidazol-1-yl)phenylamino)-6-((2,2,2-trifluoroethoxy)methyl)pyrimidin-4-yl)ethanol;

1-(2-(3-Methoxy-4-(4-methyl-1H-imidazol-1-yl)phenylamino)-6-((2,2,2-trifluoroethoxy)methyl)pyrimidin-4-yl)-2-methylpropan-1-ol;

2-(2-(3-Methoxy-4-(4-methyl-1H-imidazol-1-yl)phenylamino)-6-((2,2,2-trifluoroethoxy)-methyl)pyrimidin-4-yl)propan-2-ol;

4-((Cyclopropylmethoxy)methyl)-N-(3-methoxy-4-(4-methyl-1H-imidazol-1-yl)phenyl)-6-((2,2,2-trifluoroethoxy)methyl)pyrimidin-2-amine;

2-(6-(((3,3-Difluorocyclobutyl)methoxy)methyl)-2-(3-methoxy-4-(4-methyl-1H-imidazol-1-yl)phenylamino)pyrimidin-4-yl)propan-2-ol;

2-(2-(3-Methoxy-4-(4-methyl-1H-imidazol-1-yl)phenylamino)-6-((3,3,3-trifluoropropoxy)-methyl)pyrimidin-4-yl)propan-2-ol;

4-(Azetidin-1-yl)-N-(3-methoxy-4-(4-methyl-1H-imidazol-1-yl)phenyl)-6-((2,2,2-trifluoroethoxy)methyl)pyrimidin-2-amine;

$N^4$-Benzyl-$N^2$-(3-methoxy-4-(4-methyl-1H-imidazol-1-yl)phenyl)-$N^4$-methyl-6-((2,2,2-trifluoroethoxy)methyl)pyrimidine-2,4-diamine;

4-(4,4-Difluoropiperidin-1-yl)-N-(3-methoxy-4-(4-methyl-1H-imidazol-1-yl)phenyl)-6-((2,2,2-trifluoroethoxy)methyl)pyrimidin-2-amine;

2-(2-(3-Methoxy-4-(4-methyl-1H-imidazol-1-yl)phenylamino)-6-(methoxymethyl)pyrimidin-4-yl)propan-2-ol;

Cyclopropyl(2-(3-methoxy-4-(4-methyl-1H-imidazol-1-yl)phenylamino)-6-((2,2,2-trifluoroethoxy)methyl)pyrimidin-4-yl)methanol;

2-(6-(((Cyclopropylmethoxy)methyl)-2-(3-methoxy-4-(4-methyl-1H-imidazol-1-yl)phenylamino)pyrimidin-4-yl)propan-2-ol;

6-(((Cyclopropylmethoxy)methyl)-N2-(3-methoxy-4-(4-methyl-1H-imidazol-1-yl)phenyl)-N4-methylpyrimidine-2,4-diamine;

1-(2-(3-Methoxy-4-(4-methoxy-1H-imidazol-1-yl)phenylamino)-6-((2,2,2-trifluoroethoxy)-methyl)pyrimidin-4-yl)ethanol;

2-(2-(3-Methoxy-4-(4-methoxy-1H-imidazol-1-yl)phenylamino)-6-((2,2,2-trifluoroethoxy)-methyl)pyrimidin-4-yl)propan-2-ol;

$N^4$-(Cyclopropylmethyl)-$N^2$-(3-methoxy-4-(4-methyl-1H-imidazol-1-yl)phenyl)-6-((2,2,2-trifluoroethoxy)methyl)pyrimidine-2,4-diamine;

$N^4$-Cyclopropyl-$N^2$-(3-methoxy-4-(4-methyl-1H-imidazol-1-yl)phenyl)-6-((2,2,2-trifluoroethoxy)methyl)pyrimidine-2,4-diamine;

$N^2$-(3-Methoxy-4-(4-methyl-1H-imidazol-1-yl)phenyl)-$N^4$-(oxetan-3-yl)-6-((2,2,2-trifluoroethoxy)methyl)pyrimidine-2,4-diamine;

1-(2-(3-Methoxy-4-(4-methyl-1H-imidazol-1-yl)phenylamino)-6-((2,2,2-trifluoroethoxy)-methyl)pyrimidin-4-ylamino)-2-methylpropan-2-ol;

N2-(3-Methoxy-4-(4-methyl-1H-imidazol-1-yl)phenyl)-N4-(2-methoxyethyl)-6-((2,2,2-trifluoroethoxy)methyl)pyrimidine-2,4-diamine;

3-(2-(3-Methoxy-4-(4-methyl-1H-imidazol-1-yl)phenylamino)-6-((2,2,2-trifluoroethoxy)-methyl)pyrimidin-4-ylamino)propanenitrile;

4-((3-Fluoroazetidin-1-yl)methyl)-N-(3-methoxy-4-(4-methyl-1H-imidazol-1-yl)phenyl)-6-((2,2,2-trifluoroethoxy)methyl)pyrimidin-2-amine;

4-((Dimethylamino)methyl)-N-(3-methoxy-4-(4-methyl-1H-imidazol-1-yl)phenyl)-6-((2,2,2-trifluoroethoxy)methyl)pyrimidin-2-amine;

4-(1-(3-Fluoroazetidin-1-yl)ethyl)-N-(3-methoxy-4-(4-methyl-1H-imidazol-1-yl)phenyl)-6-((2,2,2-trifluoroethoxy)methyl)pyrimidin-2-amine;

1-(2-(3-Methoxy-4-(4-methyl-1H-imidazol-1-yl)phenylamino)-6-((2,2,2-trifluoroethoxy)-methyl)pyrimidin-4-yl)ethanol;

2-(2-(3-Methoxy-4-(4-methyl-1H-imidazol-1-yl)phenylamino)-6-((2,2,2-trifluoroethoxy)-methyl)pyrimidin-4-yl)butan-2-ol;

(2-(3-Methoxy-4-(4-methyl-1H-imidazol-1-yl)phenylamino)-6-((2,2,2-trifluoroethoxy)-methyl)pyrimidin-4-yl)(phenyl)methanol;

2-(6-(((1,3-Difluoropropan-2-yloxy)methyl)-2-(3-methoxy-4-(4-methyl-1H-imidazol-1-yl)phenylamino)pyrimidin-4-yl)propan-2-ol;

4-(Cyclopropylmethoxy)-N-[3-methoxy-4-(4-methyl-1H-imidazol-1-yl)phenyl]-6-[(2,2,2-trifluoroethoxy)methyl]pyrimidin-2-amine; and 2-(6-(1-Ethoxy-2,2-difluorocyclopropyl)-2-(3-methoxy-4-(4-methyl-1H-imidazol-1-yl)phenylamino)pyrimidin-4-yl)propan-2-ol;

or a pharmaceutically acceptable salt of any foregoing compound.

7. A pharmaceutical composition comprising as active ingredient a therapeutically effective amount of a compound according to claim 1, or a pharmaceutically acceptable salt thereof, in association with a pharmaceutically acceptable excipient, carrier or diluent.

8. A pharmaceutical composition comprising
   (i) a compound of formula (Ia) according to claim 1, or a pharmaceutically acceptable salt thereof,
   (ii) an additional therapeutic agent, or a pharmaceutically acceptable salt thereof, and
   (iii) a pharmaceutically acceptable excipient, carrier or diluent.

9. The pharmaceutical composition according to claim 8, wherein the at least one agent selected from the group consisting of acetyl cholinesterase inhibitors, anti-inflammatory agents, cognitive enhancing agents, memory enhancing agents, and atypical antipsychotic agents.

10. A pharmaceutical composition comprising
   (i) a compound of formula (Ia) according to claim 1, or a pharmaceutically acceptable salt thereof,
   (ii) at least one agent selected from the group consisting of onepezil, galantamine, rivastigmine, tacrine and memantine, Olanzapine, Aripiprazole, Risperidone, Quetiapine, Clozapine, Ziprasidone and Olanzapine/Fluoxetine, and (iii) a pharmaceutically acceptable excipient, carrier or diluent.

11. A method of treating an Aβ-related pathology in a patient in need thereof, comprising administering to the patient a therapeutically effective amount of a compound according to claim 1, or a pharmaceutically acceptable salt thereof; wherein the Aβ-related pathology is selected from the group consisting of Down's syndrome, a β-amyloid angiopathy, cerebral amyloid angiopathy, hereditary cerebral hemorrhage, mild cognitive impairment (MCI), Alzheimer's disease, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy and cortical basal degeneration.

12. A method of treating an Aβ-related pathology in a patient in need thereof, comprising administering to the patient a therapeutically effective amount of a compound according to claim 1, or a pharmaceutically acceptable salt thereof, and at least one acetyl cholinesterase inhibitor, anti-inflammatory agent, cognitive enhancing agent, memory enhancing agent, or atypical antipsychotic agent; wherein the Aβ-related pathology is selected from the group consisting of Down's syndrome, a β-amyloid angiopathy, cerebral amyloid angiopathy, hereditary cerebral hemorrhage, mild cognitive impairment (MCI), Alzheimer's disease, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy and cortical basal degeneration.

13. A method of treating an Aβ-related pathology in a patient in need thereof, comprising administering to the patient a therapeutically effective amount of a pharmaceutical composition comprising (i) a compound of formula (Ia) according to claim 1, or a pharmaceutically acceptable salt thereof, (ii) at least one agent selected from the group consisting of onepezil, galantamine, rivastigmine, tacrine and memantine, Olanzapine, Aripiprazole (marketed as ABILIFY), Risperidone (marketed as RISPERDAL), Quetiapine, Clozapine, Ziprasidone and Olanzapine/Fluoxetine, and (iii) a pharmaceutically acceptable excipient, carrier or diluent; wherein the Aβ-related pathology is selected from the group consisting of Down's syndrome, a β-amyloid angiopathy, cerebral amyloid angiopathy, hereditary cerebral hemorrhage, mild cognitive impairment (MCI), Alzheimer's disease, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy and cortical basal degeneration.

* * * * *